United States Patent
Duong et al.

(10) Patent No.: US 12,031,128 B2
(45) Date of Patent: Jul. 9, 2024

(54) RAPID DESIGN, BUILD, TEST, AND LEARN TECHNOLOGIES FOR IDENTIFYING AND USING NON-VIRAL CARRIERS

(71) Applicant: BATTELLE MEMORIAL INSTITUTE, Columbus, OH (US)

(72) Inventors: Anthony D. Duong, Columbus, OH (US); Danielle J. Huk, Hilliard, OH (US); Cherry Gupta, Columbus, OH (US); Kenneth R. Sims, Jr., Delaware, OH (US); Michael S. Koeris, Irvine, CA (US); Zachary R. Shank, London, OH (US); Ashlee J. Colbert, Blacklick, OH (US); Andrea D. McCue, Columbus, OH (US); Emma K. Schmitz, Columbus, OH (US); Caleb T. Hillrich, Columbus, OH (US); Shannon D. Miller, Hilliard, OH (US); Joanna L. Hoy, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 50 days.

(21) Appl. No.: 17/715,784

(22) Filed: Apr. 7, 2022

(65) Prior Publication Data

US 2022/0333097 A1 Oct. 20, 2022

Related U.S. Application Data

(60) Provisional application No. 63/172,069, filed on Apr. 7, 2021.

(51) Int. Cl.
| | | |
|---|---|---|
| *C12N 15/10* | (2006.01) | |
| *A61K 48/00* | (2006.01) | |
| *C12N 15/88* | (2006.01) | |
| C12Q 1/6804 | (2018.01) | |
| C12Q 1/6816 | (2018.01) | |
| C12Q 1/682 | (2018.01) | |
| G01N 33/53 | (2006.01) | |

(52) U.S. Cl.
CPC ...... *C12N 15/1065* (2013.01); *A61K 48/0041* (2013.01); *A61K 48/0091* (2013.01); *C12N 15/88* (2013.01); *C12Q 1/6804* (2013.01); *C12Q 1/6816* (2013.01); *C12Q 1/682* (2013.01); *C12Q 2525/301* (2013.01); *C12Q 2525/313* (2013.01); *G01N 33/5308* (2013.01)

(58) Field of Classification Search
CPC .......... C12N 15/1065; C12N 15/88; A61K 48/0041; A61K 48/0091; C12Q 1/6816
See application file for complete search history.

(56) References Cited

U.S. PATENT DOCUMENTS

| | | |
|---|---|---|
| 3,562,806 A | 2/1971 | Grant et al. |
| 3,678,098 A | 7/1972 | Lewis et al. |
| 3,691,123 A | 9/1972 | Clarke et al. |
| 3,706,564 A | 12/1972 | Hollister et al. |
| 3,706,565 A | 12/1972 | Ericson |
| 3,739,042 A | 6/1973 | Chu et al. |
| 3,744,969 A | 7/1973 | Alps et al. |
| 3,829,564 A | 8/1974 | Merry et al. |
| 3,847,857 A | 11/1974 | Haag et al. |
| 4,036,766 A | 7/1977 | Yamamoto et al. |
| 4,056,559 A | 11/1977 | Lewis et al. |
| 4,219,616 A | 8/1980 | Pope et al. |
| 4,237,253 A | 12/1980 | Jacquet et al. |
| 4,377,481 A | 3/1983 | Jakabhazy |
| 4,434,268 A | 2/1984 | Doroszkowsky et al. |
| 4,544,621 A | 10/1985 | Roth |
| 4,557,997 A | 12/1985 | Iwasaki et al. |
| 4,559,293 A | 12/1985 | Moriya et al. |
| 4,592,816 A | 6/1986 | Emmons et al. |
| 4,595,722 A | 6/1986 | Such |
| 4,656,027 A | 4/1987 | Sjoovist |
| 4,735,887 A | 4/1988 | Foss et al. |
| 4,755,563 A | 7/1988 | West |
| 4,775,721 A | 10/1988 | Horikawa et al. |
| 4,834,799 A | 5/1989 | Song |
| 4,855,207 A | 8/1989 | Tsubuko et al. |
| 4,925,764 A | 5/1990 | Madeleine et al. |
| 4,985,160 A | 1/1991 | Henry et al. |
| 5,085,698 A | 2/1992 | Ma et al. |
| 5,124,381 A | 6/1992 | Ward |
| 5,141,556 A | 8/1992 | Matrick |

(Continued)

FOREIGN PATENT DOCUMENTS

| | | |
|---|---|---|
| CN | 1323840 A | 11/2001 |
| CN | 1328106 A | 12/2001 |

(Continued)

OTHER PUBLICATIONS

Conesa, Ana et al., "A survey of best practices for RNA-seq data analysis." Genome Biology, Jan. 26, 2016, vol. 17, No. 13; doi:10.1186/s13059-016-0881-8.

(Continued)

*Primary Examiner* — Robert S Cabral
(74) *Attorney, Agent, or Firm* — Barnes & Thornburg LLP

(57) ABSTRACT

The disclosure relates to barcoded polymer nanoparticles for in vivo screening and for in vivo therapeutic delivery, and methods therefor. More particularly, the invention relates to polymer nanoparticles, such as reversible addition-fragmentation chain transfer (RAFT) polymer compositions, associated with polynucleotide barcodes, for therapeutic delivery, and for high throughput in vivo screening of drug delivery nanoparticles.

13 Claims, 16 Drawing Sheets

Specification includes a Sequence Listing.

(56) References Cited

U.S. PATENT DOCUMENTS

| | | |
|---|---|---|
| 5,180,425 A | 1/1993 | Matrick et al. |
| 5,205,861 A | 4/1993 | Matrick |
| 5,271,765 A | 12/1993 | Ma |
| 5,310,595 A | 5/1994 | Ali et al. |
| 5,310,778 A | 5/1994 | Shor et al. |
| 5,418,277 A | 5/1995 | Ma et al. |
| 5,428,383 A | 6/1995 | Shields et al. |
| 5,432,035 A | 7/1995 | Katagiri et al. |
| 5,512,418 A | 4/1996 | Ma |
| 5,518,534 A | 5/1996 | Pearlstine et al. |
| 5,519,081 A | 5/1996 | Ashton et al. |
| 5,519,085 A | 5/1996 | Ma et al. |
| 5,525,450 A | 6/1996 | Spiewak et al. |
| 5,620,883 A | 4/1997 | Shao et al. |
| 5,698,016 A | 12/1997 | Adams et al. |
| 5,709,714 A | 1/1998 | Natoli et al. |
| 5,750,594 A | 5/1998 | Page et al. |
| 5,969,046 A | 10/1999 | Schindler et al. |
| 5,985,573 A | 11/1999 | Hennink et al. |
| 6,004,582 A | 12/1999 | Faour et al. |
| 6,004,712 A | 12/1999 | Barbetta et al. |
| 6,022,533 A | 2/2000 | Goto et al. |
| 6,022,908 A | 2/2000 | Ma et al. |
| 6,040,358 A | 3/2000 | Page et al. |
| 6,077,635 A | 6/2000 | Okado et al. |
| 6,132,917 A | 10/2000 | Hoffend et al. |
| 6,139,856 A | 10/2000 | Kaminska et al. |
| 6,197,290 B1 | 3/2001 | Goto et al. |
| 6,207,631 B1 | 3/2001 | Kasturi et al. |
| 6,221,402 B1 | 4/2001 | Itoh et al. |
| 6,245,421 B1 | 6/2001 | Aurenty et al. |
| 6,247,808 B1 | 6/2001 | Ma et al. |
| 6,251,554 B1 | 6/2001 | Hoffend et al. |
| 6,276,273 B1 | 8/2001 | Aurenty et al. |
| 6,309,666 B1 | 10/2001 | Hatano et al. |
| 6,315,854 B1 | 11/2001 | Anhauser et al. |
| 6,372,708 B1 | 4/2002 | Kasturi et al. |
| 6,413,306 B1 | 7/2002 | Kraiter et al. |
| 6,471,349 B1 | 10/2002 | Aurenty et al. |
| 6,532,871 B1 | 3/2003 | Aurenty et al. |
| 6,624,210 B1 | 9/2003 | Petereit et al. |
| 6,692,769 B1 | 2/2004 | Ishibashi et al. |
| 6,720,387 B1 | 4/2004 | Stark et al. |
| 6,794,367 B1 | 9/2004 | Tanida et al. |
| 6,827,795 B1 | 12/2004 | Kasturi et al. |
| 6,903,064 B1 | 6/2005 | Kasturi et al. |
| 7,256,020 B2 | 8/2007 | Lyamichev et al. |
| 7,737,108 B1 | 6/2010 | Hoffman et al. |
| 8,758,860 B1 | 6/2014 | Pyles et al. |
| 9,085,618 B2 | 7/2015 | Ramasubramanyan et al. |
| 9,447,220 B2 | 9/2016 | Cho et al. |
| 9,714,940 B2 | 7/2017 | Lowery, Jr. et al. |
| 9,970,040 B2 | 5/2018 | Elbaz et al. |
| 10,201,503 B1 | 2/2019 | Li et al. |
| 10,695,443 B2 | 6/2020 | Lötvall et al. |
| 2002/0028410 A1 | 3/2002 | Choi |
| 2002/0187311 A1 | 12/2002 | Golub et al. |
| 2003/0049311 A1 | 3/2003 | McAllister et al. |
| 2003/0064036 A1 | 4/2003 | Petereit et al. |
| 2003/0071883 A1 | 4/2003 | Suzuki et al. |
| 2003/0106160 A1 | 6/2003 | Sun et al. |
| 2003/0124074 A1 | 7/2003 | Mougin et al. |
| 2003/0130160 A1 | 7/2003 | Eason et al. |
| 2003/0152856 A1 | 8/2003 | Mizoe et al. |
| 2003/0199419 A1 | 10/2003 | Rodrigues et al. |
| 2004/0091538 A1 | 5/2004 | Pollock-Dove et al. |
| 2004/0096490 A1 | 5/2004 | Bracht et al. |
| 2004/0104501 A1 | 6/2004 | Petereit et al. |
| 2004/0109869 A1 | 6/2004 | Glenn et al. |
| 2004/0198838 A1 | 10/2004 | Alles et al. |
| 2004/0208925 A1 | 10/2004 | Oner et al. |
| 2004/0219211 A1 | 11/2004 | Criere et al. |
| 2004/0249035 A1 | 12/2004 | Petereit et al. |
| 2005/0020779 A1 | 1/2005 | Mougin et al. |
| 2005/0026803 A1 | 2/2005 | Sivik et al. |
| 2005/0048112 A1 | 3/2005 | Breitenbach et al. |
| 2005/0053566 A1 | 3/2005 | Nguyen-Kim et al. |
| 2005/0070486 A1 | 3/2005 | Wieland-Berghausen et al. |
| 2005/0084529 A1 | 4/2005 | Rosenberg et al. |
| 2005/0090599 A1 | 4/2005 | Spinelli |
| 2005/0208133 A1 | 9/2005 | Tsutsumi et al. |
| 2005/0281871 A1 | 12/2005 | Petereit et al. |
| 2006/0051412 A1 | 3/2006 | Petereit et al. |
| 2006/0089425 A1 | 4/2006 | Chopra et al. |
| 2006/0110433 A1 | 5/2006 | Terahara et al. |
| 2006/0257484 A1 | 11/2006 | Hwang et al. |
| 2006/0280798 A1 | 12/2006 | Ensoli |
| 2007/0027213 A1 | 2/2007 | Oberegger et al. |
| 2007/0072996 A1 | 3/2007 | Kedar et al. |
| 2007/0088118 A1 | 4/2007 | Dungworth et al. |
| 2007/0141013 A1 | 6/2007 | Nguyen-Kim et al. |
| 2007/0178059 A1 | 8/2007 | Moser et al. |
| 2007/0203245 A1 | 8/2007 | Koltun et al. |
| 2007/0231397 A1 | 10/2007 | Petereit et al. |
| 2007/0259028 A1 | 11/2007 | Ito |
| 2007/0275060 A1 | 11/2007 | Befumo et al. |
| 2007/0275071 A1 | 11/2007 | Ensoli et al. |
| 2008/0050432 A1 | 2/2008 | Jun et al. |
| 2008/0050450 A1 | 2/2008 | Arnold et al. |
| 2008/0075689 A1 | 3/2008 | Pierobon et al. |
| 2008/0089853 A1 | 4/2008 | Nguyen-Kim et al. |
| 2008/0153982 A1 | 6/2008 | Lai et al. |
| 2008/0181948 A1 | 7/2008 | Berndl et al. |
| 2008/0193405 A1 | 8/2008 | Mukherjee et al. |
| 2008/0193544 A1 | 8/2008 | Bruck-Scheffler et al. |
| 2008/0226731 A1 | 9/2008 | Vasanthavada et al. |
| 2008/0233177 A1 | 9/2008 | Meconi |
| 2008/0280999 A1 | 11/2008 | Lakshman |
| 2008/0286221 A1 | 11/2008 | Kim et al. |
| 2008/0299391 A1 | 12/2008 | White et al. |
| 2008/0306233 A1 | 12/2008 | Muhrer et al. |
| 2009/0023754 A1 | 1/2009 | Lee et al. |
| 2009/0053315 A1 | 2/2009 | Brough et al. |
| 2009/0099075 A1 | 4/2009 | Barg et al. |
| 2009/0108241 A1 | 4/2009 | Ogura et al. |
| 2009/0118399 A1 | 5/2009 | Benbakoura et al. |
| 2009/0148522 A1 | 6/2009 | Kowalski et al. |
| 2009/0161058 A1 | 6/2009 | Sherman |
| 2009/0175952 A1 | 7/2009 | Woo et al. |
| 2009/0220596 A1 | 9/2009 | Rosenberg et al. |
| 2009/0221621 A1 | 9/2009 | Sathyan et al. |
| 2009/0280183 A1 | 11/2009 | Lizio et al. |
| 2009/0285891 A1 | 11/2009 | Jung et al. |
| 2009/0302493 A1 | 12/2009 | Kessler et al. |
| 2009/0311320 A1 | 12/2009 | Oury et al. |
| 2009/0318847 A1 | 12/2009 | Sebree et al. |
| 2009/0321945 A1 | 12/2009 | Besling |
| 2010/0038816 A1 | 2/2010 | Ghogh et al. |
| 2010/0048737 A1 | 2/2010 | Wendel et al. |
| 2010/0074951 A1 | 3/2010 | Kim et al. |
| 2010/0087544 A1 | 4/2010 | Kim et al. |
| 2010/0120970 A1 | 5/2010 | Biggs et al. |
| 2010/0143459 A1 | 6/2010 | Liepold et al. |
| 2010/0143470 A1 | 6/2010 | Kim et al. |
| 2010/0143590 A1 | 6/2010 | Held et al. |
| 2010/0152299 A1 | 6/2010 | Vasanthavada et al. |
| 2010/0160183 A1 | 6/2010 | Xu et al. |
| 2010/0174040 A1 | 7/2010 | Kim et al. |
| 2010/0209480 A1 | 8/2010 | Altenburger et al. |
| 2010/0209520 A1 | 8/2010 | Kubo |
| 2010/0233447 A1 | 9/2010 | Campbell |
| 2010/0247635 A1 | 9/2010 | Rosenberg et al. |
| 2010/0266859 A1 | 10/2010 | Abe et al. |
| 2010/0272797 A1 | 10/2010 | Kim et al. |
| 2010/0278899 A1 | 11/2010 | Sugiura et al. |
| 2010/0286288 A1 | 11/2010 | Langguth et al. |
| 2010/0291311 A1 | 11/2010 | Trouve et al. |
| 2010/0310644 A1 | 12/2010 | Liebmann et al. |
| 2010/0323090 A1 | 12/2010 | Ishizaki et al. |
| 2011/0002988 A1 | 1/2011 | Ishizaki et al. |
| 2011/0005773 A1 | 1/2011 | Dusterhoft et al. |
| 2011/0032303 A1 | 2/2011 | Li |
| 2011/0052683 A1 | 3/2011 | Kim et al. |
| 2011/0052699 A1 | 3/2011 | Funke et al. |

(56) References Cited

U.S. PATENT DOCUMENTS

| | | |
|---|---|---|
| 2011/0091563 A1 | 4/2011 | Kurasawa et al. |
| 2011/0111021 A1 | 5/2011 | Kim et al. |
| 2011/0111022 A1 | 5/2011 | Kim et al. |
| 2011/0117194 A1 | 5/2011 | Kim et al. |
| 2011/0123636 A1 | 5/2011 | Stayton et al. |
| 2011/0144260 A1 | 6/2011 | Tanabe et al. |
| 2011/0201759 A1 | 8/2011 | Takahashi |
| 2011/0242154 A1 | 10/2011 | Roberts et al. |
| 2011/0257289 A1 | 10/2011 | Biggs et al. |
| 2011/0263470 A1 | 10/2011 | Qin et al. |
| 2011/0269913 A1 | 11/2011 | Balk et al. |
| 2011/0274893 A1 | 11/2011 | Adolf et al. |
| 2011/0275775 A1 | 11/2011 | Goto et al. |
| 2011/0287100 A1 | 11/2011 | Desset-Brethes et al. |
| 2011/0305660 A1 | 12/2011 | Stayton et al. |
| 2011/0306632 A1 | 12/2011 | Miller et al. |
| 2011/0312973 A1 | 12/2011 | Liepold et al. |
| 2012/0009223 A1 | 1/2012 | Wenguang et al. |
| 2012/0053248 A1 | 3/2012 | Kolter et al. |
| 2012/0093982 A1 | 4/2012 | Tsukioka et al. |
| 2012/0143039 A1 | 6/2012 | Hartwig et al. |
| 2012/0172574 A1 | 7/2012 | Helou et al. |
| 2012/0183769 A1 | 7/2012 | Nasu et al. |
| 2012/0190724 A1 | 7/2012 | Na et al. |
| 2012/0213827 A1 | 8/2012 | Chatterji et al. |
| 2012/0220550 A1 | 8/2012 | Bae et al. |
| 2012/0232117 A1 | 9/2012 | Bae et al. |
| 2012/0251583 A1 | 10/2012 | Rothemund |
| 2012/0258909 A1 | 10/2012 | Liepold et al. |
| 2012/0282303 A1 | 11/2012 | Ito |
| 2012/0282310 A1 | 11/2012 | Lucet-Levannier et al. |
| 2012/0283670 A1 | 11/2012 | Ito |
| 2012/0323190 A1 | 12/2012 | Ito |
| 2012/0328891 A1 | 12/2012 | Suwa et al. |
| 2013/0005874 A1 | 1/2013 | Nakajima et al. |
| 2013/0011362 A1 | 1/2013 | Monahan et al. |
| 2013/0017245 A1 | 1/2013 | Takano |
| 2013/0034599 A1 | 2/2013 | Thaxton et al. |
| 2013/0040236 A1 | 2/2013 | Fukushima et al. |
| 2013/0085233 A1 | 4/2013 | Niitani et al. |
| 2013/0090480 A1 | 4/2013 | Park Choo et al. |
| 2013/0095168 A1 | 4/2013 | Choi et al. |
| 2013/0129869 A1 | 5/2013 | Hafezi et al. |
| 2013/0171646 A1 | 7/2013 | Park et al. |
| 2013/0172239 A1 | 7/2013 | Gao et al. |
| 2013/0224859 A1 | 8/2013 | Bachelet et al. |
| 2013/0236551 A1 | 9/2013 | Cavazza |
| 2013/0239339 A1 | 9/2013 | Bown et al. |
| 2013/0243873 A1 | 9/2013 | Aversa et al. |
| 2013/0261019 A1 | 10/2013 | Lin et al. |
| 2013/0274297 A1 | 10/2013 | Gatti et al. |
| 2013/0317096 A1 | 11/2013 | Yap et al. |
| 2014/0018404 A1 | 1/2014 | Chen et al. |
| 2014/0080868 A1 | 3/2014 | Ng et al. |
| 2014/0080869 A1 | 3/2014 | Krishnan et al. |
| 2014/0080886 A1 | 3/2014 | Pilot-Matias et al. |
| 2014/0088152 A1 | 3/2014 | Bae et al. |
| 2014/0128418 A1 | 5/2014 | Bae et al. |
| 2014/0128827 A1 | 5/2014 | Song |
| 2014/0155388 A1 | 6/2014 | Brzeczko et al. |
| 2014/0161893 A1 | 6/2014 | Shen et al. |
| 2014/0206742 A1 | 7/2014 | Lomuscio et al. |
| 2014/0235790 A1 | 8/2014 | Stayton et al. |
| 2014/0248350 A1 | 9/2014 | Reyes et al. |
| 2014/0271857 A1 | 9/2014 | Nelson et al. |
| 2014/0303334 A1 | 10/2014 | Goto et al. |
| 2015/0045353 A1 | 2/2015 | Comer et al. |
| 2015/0086624 A1 | 3/2015 | Cho et al. |
| 2015/0104408 A1 | 4/2015 | Wakefield et al. |
| 2015/0118294 A1 | 4/2015 | Song et al. |
| 2015/0132479 A1 | 5/2015 | Arfsten et al. |
| 2015/0164816 A1 | 6/2015 | Jaklenec et al. |
| 2015/0174250 A1 | 6/2015 | Griffiths et al. |
| 2015/0191132 A1 | 7/2015 | Muramoto et al. |
| 2015/0218125 A1 | 8/2015 | Bae et al. |
| 2015/0232729 A1 | 8/2015 | Zhao et al. |
| 2015/0258093 A1 | 9/2015 | Miller et al. |
| 2015/0283254 A1 | 10/2015 | Duvall et al. |
| 2015/0297526 A1 | 10/2015 | Puniya et al. |
| 2015/0374634 A1 | 12/2015 | Koo et al. |
| 2016/0045446 A1 | 2/2016 | Shibata et al. |
| 2016/0187323 A1 | 6/2016 | Farokhzad et al. |
| 2016/0193246 A1 | 7/2016 | Grandfils et al. |
| 2016/0194368 A1 | 7/2016 | Hoge et al. |
| 2016/0194625 A1 | 7/2016 | Hoge et al. |
| 2016/0220472 A1 | 8/2016 | Wang et al. |
| 2016/0243221 A1 | 8/2016 | Hoge et al. |
| 2016/0243274 A1 | 8/2016 | Chisholm et al. |
| 2016/0244501 A1 | 8/2016 | Ellsworth et al. |
| 2016/0244502 A1 | 8/2016 | Bolen et al. |
| 2016/0250170 A1 | 9/2016 | Hsu et al. |
| 2016/0279251 A1 | 9/2016 | Stayton et al. |
| 2016/0279289 A1 | 9/2016 | Chisholm et al. |
| 2016/0313566 A1 | 10/2016 | Le et al. |
| 2016/0317445 A1 | 11/2016 | Saly et al. |
| 2016/0317647 A1 | 11/2016 | Ciaramella et al. |
| 2016/0375017 A1 | 12/2016 | Asmus et al. |
| 2016/0376333 A1 | 12/2016 | Procko et al. |
| 2017/0002060 A1 | 1/2017 | Bolen et al. |
| 2017/0079932 A1 | 3/2017 | Emgenbroich et al. |
| 2017/0087174 A1 | 3/2017 | Beumont et al. |
| 2017/0105945 A1 | 4/2017 | Emgenbroich et al. |
| 2017/0119690 A1 | 5/2017 | Hansen et al. |
| 2017/0128380 A1 | 5/2017 | Wang |
| 2017/0173128 A1 | 6/2017 | Hoge et al. |
| 2017/0211023 A1 | 7/2017 | Zhang |
| 2017/0231989 A1 | 8/2017 | Hayashi et al. |
| 2017/0240765 A1 | 8/2017 | Nabuurs et al. |
| 2017/0247381 A1 | 8/2017 | Mao et al. |
| 2017/0296484 A1 | 10/2017 | Kottayil et al. |
| 2017/0304213 A1 | 10/2017 | Shi et al. |
| 2017/0327463 A1 | 11/2017 | Fung et al. |
| 2018/0031971 A1 | 2/2018 | Hustad et al. |
| 2018/0031972 A1 | 2/2018 | Hustad et al. |
| 2018/0200190 A1 | 7/2018 | Dharmadhikari et al. |
| 2018/0221295 A1 | 8/2018 | Hansen et al. |
| 2018/0221300 A1 | 8/2018 | Emgenbroich et al. |
| 2018/0221402 A1 | 8/2018 | Prieve et al. |
| 2018/0230489 A1 | 8/2018 | Kotin |
| 2018/0237800 A1 | 8/2018 | Murthy et al. |
| 2018/0318365 A1 | 11/2018 | Yeung et al. |
| 2018/0333683 A1 | 11/2018 | Liu et al. |
| 2018/0346797 A1 | 12/2018 | Kalgaonkar et al. |
| 2019/0000765 A1 | 1/2019 | Hattori et al. |
| 2019/0054069 A1 | 2/2019 | Chen et al. |
| 2019/0060425 A1 | 2/2019 | Scheel et al. |
| 2019/0070143 A1 | 3/2019 | Boulas et al. |
| 2019/0070233 A1 | 3/2019 | Yeung et al. |
| 2019/0077923 A1 | 3/2019 | Beaume et al. |
| 2019/0091339 A1 | 3/2019 | Miller et al. |
| 2019/0099381 A1 | 4/2019 | Gong et al. |
| 2019/0125663 A1 | 5/2019 | Herry et al. |
| 2019/0153471 A1 | 5/2019 | Paul et al. |
| 2019/0192691 A1 | 6/2019 | Barrett et al. |
| 2019/0194376 A1 | 6/2019 | Maejima et al. |
| 2019/0203030 A1 | 7/2019 | Cheong et al. |
| 2019/0224339 A1 | 7/2019 | Paul et al. |
| 2019/0231712 A1 | 8/2019 | Matsumoto et al. |
| 2019/0247350 A1 | 8/2019 | Mizugaki et al. |
| 2019/0254966 A1 | 8/2019 | Bellinger et al. |
| 2019/0270991 A1 | 9/2019 | Foot et al. |
| 2019/0274346 A1 | 9/2019 | Gore et al. |
| 2019/0365773 A1 | 12/2019 | Yokoyama et al. |
| 2019/0382837 A1 | 12/2019 | Spurbeck et al. |
| 2020/0016092 A1 | 1/2020 | Bernardo et al. |
| 2020/0038390 A1 | 2/2020 | Park et al. |
| 2020/0051813 A1 | 2/2020 | Osaki et al. |
| 2020/0069696 A1 | 3/2020 | Liu |
| 2020/0078463 A1 | 3/2020 | Park et al. |
| 2020/0086616 A1 | 3/2020 | Meise et al. |
| 2020/0123391 A1 | 4/2020 | Habets et al. |
| 2020/0129440 A1 | 4/2020 | Baek et al. |
| 2020/0138072 A1 | 5/2020 | Yucel et al. |
| 2020/0163962 A1 | 5/2020 | Jahagirdar et al. |

(56) References Cited

U.S. PATENT DOCUMENTS

| | | |
|---|---|---|
| 2020/0165630 A1 | 5/2020 | Paul et al. |
| 2020/0171169 A1 | 6/2020 | Duvall et al. |
| 2020/0188290 A1 | 6/2020 | Herrmann et al. |
| 2020/0197289 A1 | 6/2020 | Wang et al. |
| 2020/0206133 A1 | 7/2020 | Alsenz et al. |
| 2020/0224022 A1 | 7/2020 | Gigmes et al. |
| 2020/0261426 A1 | 8/2020 | Park et al. |
| 2020/0308331 A1 | 10/2020 | Kang et al. |
| 2020/0390752 A1 | 12/2020 | Moon et al. |
| 2021/0069111 A1 | 3/2021 | Reineke et al. |
| 2021/0128479 A1 | 5/2021 | Cheng et al. |
| 2021/0163985 A1 | 6/2021 | Sah et al. |
| 2021/0196682 A1 | 7/2021 | Chen et al. |
| 2021/0213002 A1 | 7/2021 | Natori et al. |
| 2021/0330599 A1 | 10/2021 | Benoit et al. |
| 2021/0347950 A1 | 11/2021 | Kou et al. |
| 2021/0355454 A1 | 11/2021 | Cardinal et al. |
| 2021/0371470 A1 | 12/2021 | Murlidharan et al. |
| 2021/0373002 A1 | 12/2021 | Gopinath et al. |
| 2021/0387156 A1 | 12/2021 | Oschmann et al. |
| 2021/0387946 A1 | 12/2021 | Lindemann et al. |
| 2022/0008346 A1 | 1/2022 | Wilson et al. |
| 2022/0016098 A1 | 1/2022 | Cho et al. |
| 2022/0016271 A1 | 1/2022 | Farokhzad et al. |
| 2022/0031607 A1 | 2/2022 | Cho et al. |
| 2022/0143062 A1 | 5/2022 | Kahvejian et al. |
| 2022/0175812 A1 | 6/2022 | Duong et al. |
| 2022/0233514 A1 | 7/2022 | Choi et al. |
| 2022/0233580 A1 | 7/2022 | Takeshita et al. |
| 2022/0243225 A1 | 8/2022 | Mathur et al. |
| 2022/0291432 A1 | 9/2022 | Donal |
| 2023/0059080 A1 | 2/2023 | Lee et al. |
| 2023/0067461 A1 | 3/2023 | Lee et al. |
| 2023/0092431 A1 | 3/2023 | Isabella et al. |
| 2023/0218536 A1 | 7/2023 | Solomun et al. |
| 2023/0227687 A1 | 7/2023 | Li et al. |
| 2023/0310621 A1 | 10/2023 | Grandfils et al. |

FOREIGN PATENT DOCUMENTS

| | | |
|---|---|---|
| CN | 1806901 A | 7/2006 |
| CN | 1813683 A | 8/2006 |
| CN | 1896112 A | 1/2007 |
| CN | 101444513 A | 6/2009 |
| CN | 101643412 A | 2/2010 |
| CN | 101735383 A | 6/2010 |
| CN | 102030871 A | 4/2011 |
| CN | 102250278 A | 11/2011 |
| CN | 102949342 A | 3/2013 |
| CN | 103113509 A | 5/2013 |
| CN | 103255174 A | 8/2013 |
| CN | 103319668 A | 9/2013 |
| CN | 103333283 A | 10/2013 |
| CN | 103536972 A | 1/2014 |
| CN | 103755870 A | 4/2014 |
| CN | 103976972 A | 8/2014 |
| CN | 104479064 A | 4/2015 |
| CN | 104772051 A | 7/2015 |
| CN | 104784155 A | 7/2015 |
| CN | 104922078 A | 9/2015 |
| CN | 104971073 A | 10/2015 |
| CN | 105504923 A | 4/2016 |
| CN | 105833272 A | 8/2016 |
| CN | 105833287 A | 8/2016 |
| CN | 105949365 A | 9/2016 |
| CN | 106117580 A | 11/2016 |
| CN | 106236785 A | 12/2016 |
| CN | 106478904 A | 3/2017 |
| CN | 106811998 A | 6/2017 |
| CN | 107173546 A | 9/2017 |
| CN | 107596368 A | 1/2018 |
| CN | 115714187 A | 2/2023 |
| DE | 2446449 A1 | 4/1975 |
| EP | 0217137 A2 | 4/1987 |
| EP | 0587333 A2 | 3/1994 |
| EP | 0597577 A1 | 5/1994 |
| EP | 0945148 A1 | 9/1999 |
| EP | 1008634 A1 | 6/2000 |
| GB | 1284489 A | 8/1972 |
| GB | 1314285 A | 4/1973 |
| GB | 1324087 A | 7/1973 |
| IN | 2012MU01581 | 1/2014 |
| IN | 2014KO01127 | 5/2016 |
| IN | 201611026597 A | 3/2018 |
| IN | 201921005566 A | 8/2020 |
| JP | S5156886 A | 5/1976 |
| JP | S51100129 A | 9/1976 |
| JP | H01229014 A | 9/1989 |
| JP | 2003345095 A | 12/2003 |
| JP | 2008274217 A | 11/2008 |
| JP | 2008274218 A | 11/2008 |
| JP | 2008274219 A | 11/2008 |
| JP | 2009016258 A | 1/2009 |
| JP | 2010111781 A | 5/2010 |
| JP | 2011074250 A | 4/2011 |
| JP | 2011207963 A | 10/2011 |
| JP | 2013029832 A | 2/2013 |
| JP | 2013114184 A | 6/2013 |
| JP | 2013237821 A | 11/2013 |
| JP | 2016065115 A | 4/2016 |
| JP | 2016126154 A | 7/2016 |
| JP | 2017058405 A | 3/2017 |
| JP | 2018154752 A | 10/2018 |
| JP | 2018174919 A | 11/2018 |
| JP | 2018203987 A | 12/2018 |
| JP | 2019127444 A | 8/2019 |
| JP | 2020074704 A | 5/2020 |
| JP | 2022057447 A | 4/2022 |
| JP | 2022076360 A | 5/2022 |
| JP | 2022117407 A | 8/2022 |
| KR | 830000972 | 4/1983 |
| KR | 20020016069 A | 3/2002 |
| KR | 20030078118 A | 10/2003 |
| KR | 20050023239 A | 3/2005 |
| KR | 20080002313 A | 1/2008 |
| KR | 20080008769 A | 1/2008 |
| KR | 100867639 B1 | 11/2008 |
| KR | 20080097787 A | 11/2008 |
| KR | 20090114190 A | 11/2009 |
| KR | 100994148 B1 | 11/2010 |
| KR | 20110043347 A | 4/2011 |
| KR | 20110117758 A | 10/2011 |
| KR | 20110119542 A | 11/2011 |
| KR | 20110135018 A | 12/2011 |
| KR | 20120047345 A | 5/2012 |
| KR | 20120134329 A | 12/2012 |
| KR | 20120134605 A | 12/2012 |
| KR | 20130010708 A | 1/2013 |
| KR | 20130013157 A | 2/2013 |
| KR | 20130027822 A | 3/2013 |
| KR | 20130030907 A | 3/2013 |
| KR | 101312286 B1 | 9/2013 |
| KR | 20140095767 A | 8/2014 |
| KR | 20140105941 A | 9/2014 |
| KR | 101458468 B1 | 11/2014 |
| KR | 20140130579 A | 11/2014 |
| KR | 20150105043 A | 9/2015 |
| KR | 20170076494 A | 7/2017 |
| KR | 101827744 B1 | 2/2018 |
| KR | 20180029147 A | 3/2018 |
| KR | 101850629 B1 | 4/2018 |
| KR | 20180099263 A | 9/2018 |
| KR | 101923028 B1 | 11/2018 |
| KR | 101943270 B1 | 1/2019 |
| KR | 20190111448 A | 10/2019 |
| KR | 102107332 B1 | 5/2020 |
| KR | 102157964 B1 | 9/2020 |
| KR | 102207353 B1 | 1/2021 |
| KR | 102207354 B1 | 1/2021 |
| KR | 102212503 B1 | 2/2021 |
| KR | 102212504 B1 | 2/2021 |
| KR | 102212505 B1 | 2/2021 |
| KR | 20210122720 A | 10/2021 |
| PL | 440443 A1 | 8/2023 |

(56) References Cited

FOREIGN PATENT DOCUMENTS

| | | |
|---|---|---|
| RU | 2582704 C1 | 4/2016 |
| TW | 201204713 A | 2/2012 |
| TW | 201404805 A | 2/2014 |
| WO | 1991013145 A1 | 9/1991 |
| WO | 1998051749 A1 | 11/1998 |
| WO | 03/090780 A1 | 6/2003 |
| WO | 2004096422 A1 | 11/2004 |
| WO | 2007060462 A1 | 5/2007 |
| WO | 2008005543 A2 | 1/2008 |
| WO | 2007078765 A3 | 4/2008 |
| WO | 2008050987 A1 | 5/2008 |
| WO | 2009038340 A1 | 3/2009 |
| WO | 2009088220 A2 | 7/2009 |
| WO | 2009103735 A1 | 8/2009 |
| WO | 2009125987 A2 | 10/2009 |
| WO | 2009127922 A2 | 10/2009 |
| WO | 2009134053 A2 | 11/2009 |
| WO | 2009134076 A2 | 11/2009 |
| WO | 2009141159 A1 | 11/2009 |
| WO | 2009142421 A2 | 11/2009 |
| WO | 2009151295 A2 | 12/2009 |
| WO | 2010008203 A1 | 1/2010 |
| WO | 2010008244 A2 | 1/2010 |
| WO | 2011025167 A2 | 3/2011 |
| WO | 2011025267 A2 | 3/2011 |
| WO | 2011025269 A2 | 3/2011 |
| WO | 2011025270 A2 | 3/2011 |
| WO | 2011025271 A2 | 3/2011 |
| WO | 2011/154331 A1 | 12/2011 |
| WO | 2012/101235 A1 | 8/2012 |
| WO | 2012061719 A3 | 8/2012 |
| WO | 2012108631 A2 | 8/2012 |
| WO | 2012119997 A1 | 9/2012 |
| WO | 2012138013 A1 | 10/2012 |
| WO | 2012140415 A1 | 10/2012 |
| WO | 2012156058 A1 | 11/2012 |
| WO | 2012156059 A1 | 11/2012 |
| WO | 2012158610 A1 | 11/2012 |
| WO | 2013135853 A1 | 9/2013 |
| WO | 2014109308 A1 | 7/2014 |
| WO | 2015089419 A1 | 6/2015 |
| WO | 2015/134787 A2 | 9/2015 |
| WO | 2016025747 A1 | 2/2016 |
| WO | 2016164762 A1 | 10/2016 |
| WO | 2016195153 A1 | 12/2016 |
| WO | 2017/184768 A2 | 10/2017 |
| WO | 2017176040 A1 | 10/2017 |
| WO | 2017/210666 A1 | 12/2017 |
| WO | 2018112555 A1 | 6/2018 |
| WO | 2018190355 A1 | 10/2018 |
| WO | 2019/027767 A1 | 2/2019 |
| WO | 2019088662 A1 | 5/2019 |
| WO | 2019126627 A1 | 6/2019 |
| WO | 2019152957 A1 | 8/2019 |
| WO | 2019199133 A1 | 10/2019 |
| WO | 2019220088 A1 | 11/2019 |
| WO | 2020017808 A1 | 1/2020 |
| WO | 2020051507 A1 | 3/2020 |
| WO | 2020080875 A1 | 4/2020 |
| WO | 2020106916 A1 | 5/2020 |
| WO | 2020247382 A1 | 12/2020 |
| WO | 2021007382 A1 | 1/2021 |
| WO | 2021076977 A1 | 4/2021 |
| WO | 2021091188 A1 | 5/2021 |
| WO | 2021125797 A1 | 6/2021 |
| WO | 2021194253 A1 | 9/2021 |
| WO | 2021255262 A1 | 12/2021 |
| WO | 2022091971 A1 | 5/2022 |
| WO | 2022120194 A1 | 6/2022 |
| WO | 2022129097 A2 | 6/2022 |
| WO | 2022139687 A1 | 6/2022 |
| WO | 2022245307 A1 | 11/2022 |
| WO | 2022266119 A1 | 12/2022 |
| WO | 2023023055 A1 | 2/2023 |
| WO | 2023107574 A2 | 6/2023 |
| WO | 2023193244 A1 | 10/2023 |
| WO | 2023239921 A1 | 12/2023 |
| WO | 2023239922 A1 | 12/2023 |

OTHER PUBLICATIONS

PCT Written Opinion for PCT/US22/23902, dated Sep. 9, 2022.
U.S. Appl. No. 18/475,879, Pending.
U.S. Appl. No. 18/332,065, Pending.
U.S. Appl. No. 17/542,055, Pending.
U.S. Appl. No. 18/332101, Pending.
Cheng et al. "Polycation Architecture Affects Complexation and Delivery of Short Antisense Oligonucleotides: Micelleplexes Outperform Polyplexes." Biomacromolecules 2022 23 (8), 3257-3271, DOI: 10.1021/acs.biomac.2c00338.
Sprouse et al. "Tuning Cationic Block Copolymer Micelle Size by pH and Ionic Strength." Biomacromolecules 2016, 17, 9, 2849-2859. DOI:10.1021/acs.biomac.6b00654.
Convertine et al. "Development of a novel endosomolytic diblock copolymer for siRNA delivery." Journal of controlled release : official journal of the Controlled Release Society vol. 133,3 (2009): 221-9. DOI: 10.1016/j.jconrel.2008.10.004.
Convertine et al. "pH-responsive polymeric micelle carriers for siRNA drugs." Biomacromolecules vol. 11,11 (2010): 2904-11. doi: 10.1021/bm100652w.
Lauber et al. "pH- and Thermoresponsive Self-Assembly of Cationic Triblock Copolymers with Controlled Dynamics." Macromolecules 2017, 50, 1, 416-423. doi: 10.1021/acs.macromol.6b02201.
Haridharan et al. "Exploration of Novel Pyrene Labeled Amphiphilic Block Copolymers: Synthesis Via ATRP, Characterization and Properties." Journal of Macromolecular Science, Part A, vol. 47, No. 9, Jul. 2010, pp. 918-926, doi:10.1080/10601325.2010.501681.
Kanth et al. "Recent advances in development of poly (dimethylaminoethyl methacrylate) antimicrobial polymers, European Polymer Journal." vol. 163, 2022, doi: 10.1016/j.eurpolymj.2021.110930.
Manganiello et al. "Diblock copolymers with tunable pH transitions for gene delivery." Biomaterials vol. 33,7 (2012): 2301-9. doi: 10.1016/j.biomaterials.2011.11.019.
Muehlebach et al. "Synthesis of Well-Defined Macromonomers and Comb Copolymers from Polymers Made by Atom Transfer Radical Polymerization." J Polym Sci Part A: Polym Chem. vol. 41,21 (2003): 3425-3439, doi: 10.1002/pola. 10940.
Pegg et al. "Solubilisation of oils in aqueous solutions of a random cationic copolymer." Journal of colloid and interface science vol. 502 (2017): 210-218. doi:10.1016/j.jcis.2017.04.093.
Grimme et al. "Polycation Architecture Affects Complexation and Delivery of Short Antisense Oligonucleotides: Micelleplexes Outperform Polyplexes." Biomacromolecules 2022, 23, 8, 3257-3271, doi: 10.1021/acs.biomac.2c00338.

The DBTL cycle for non-viral gene delivery development based on three pillars: automated synthesis, high throughput testing, and machine learning design.

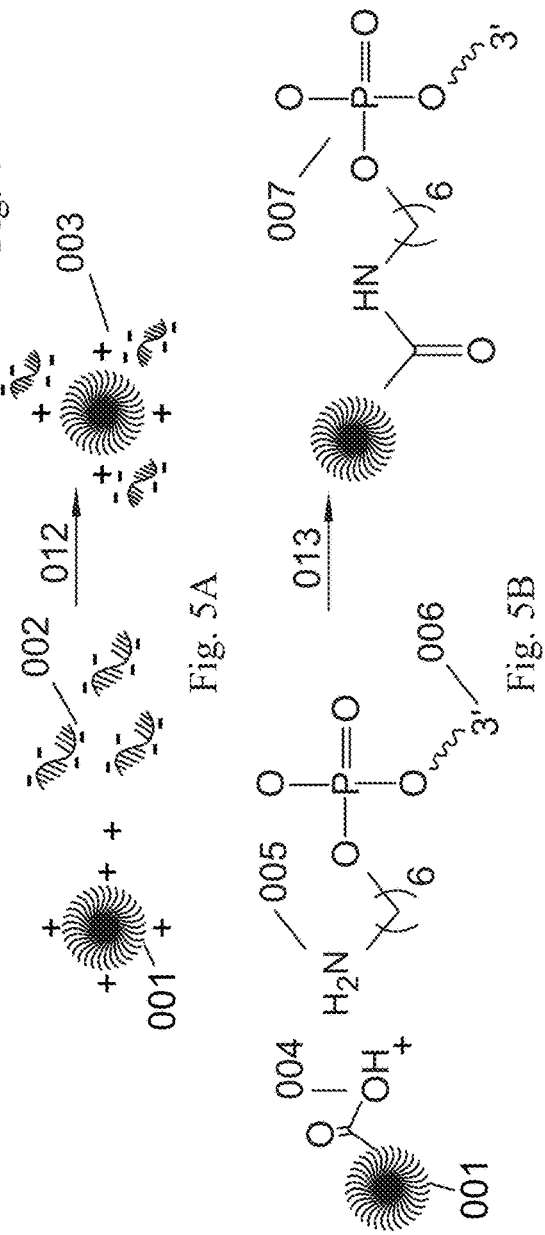

```
                         SEQUENCE LISTING

<160> NUMBER OF SEQ ID NOS: 1003

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctacataat                                                           10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgttacaca                                                           10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tggggcccaa                                                           10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagtttatcc                                                           10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
accccgtctt                                                              10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggccatca                                                              10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagcttgctc                                                              10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acgttctata                                                              10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tacagcaaaa                                                              10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gttaggtggt                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```
ggagaccgac                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tggccccttg                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggccgtaag                                                              10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgttcgtcaa                                                              10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cggacgtgga                                                              10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 agaggggggca                                                             10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gttcaggtcg                                                              10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctcgcaagag                                                              10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcaacgactt                                                              10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gccatccatc                                                              10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttccgagcag                                                              10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cttctggaca                                                              10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aacattagac                                                              10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagcaatagt                                                              10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agggtaagac                                                              10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgttgtcttg                                                              10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttccccgcc                                                              10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgaatggatc                                                              10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
catcacttgc                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctctcgcact                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gttcacgtgc                                                          10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aataagcctg                                                          10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttaacaatt                                                          10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
attcagatcc                                                          10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cctgctgatt                                                          10

```
<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttggtcata                                                          10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcttcctgtt                                                          10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
actgccatgg                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
catgtatagt                                                          10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggtagcggca                                                          10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcactctaac                                                          10

<210> SEQ ID NO 42
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaggtgcacc                                                          10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aatgctcgtt                                                          10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgtctagaaa                                                          10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgcctgcct                                                          10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
actataaaag                                                          10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tagtatcgag                                                          10

<210> SEQ ID NO 48
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atcgcagtcc                                                            10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcatcagaac                                                            10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcctagacgc                                                            10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gccgggcggg                                                            10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcccagaaga                                                            10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cttagagctg                                                            10

<210> SEQ ID NO 54
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 54
gtctgcgctt                                                            10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cgccgtcctt                                                            10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tttatctgct                                                            10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tgcttcggag                                                            10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggggagaatg                                                            10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gtggtaagtg                                                            10

<210> SEQ ID NO 60
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 60
gaaattagta                                                          10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gctatcctaa                                                          10

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atctgtacga                                                          10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agttcggggc                                                          10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cgagtctgtc                                                          10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atcctacgca                                                          10

<210> SEQ ID NO 66
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 66
atggtggata                                                          10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cctctaacta                                                          10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
atagctgcac                                                          10

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gacagaattt                                                          10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
caattggcat                                                          10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tctagtagac                                                          10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 72
ttattcatgg                                                             10

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttggcaaccg                                                             10

<210> SEQ ID NO 74
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cataatacat                                                             10

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
acagactcac                                                             10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcgatgctgc                                                             10

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
catctttgcc                                                             10

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 78
gtgactccag                                                                  10

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggacgagtct                                                                  10

<210> SEQ ID NO 80
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tagtggcgtg                                                                  10

<210> SEQ ID NO 81
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aacgcagctt                                                                  10

<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agaacaggtg                                                                  10

<210> SEQ ID NO 83
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aggctatgtt                                                                  10

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 84
cctggatctt                                                            10

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctagccggcc                                                            10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
accagttatc                                                            10

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
acgttatagc                                                            10

<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tcgagtttga                                                            10

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tgaagcgagc                                                            10

<210> SEQ ID NO 90
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
```
gactggcgaa    10

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gatggaccta    10

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtccacaacg    10

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cctccccaga    10

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttatgacgcc    10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cttgatccgt    10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aatgcgcaat                                                          10

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtacccctca                                                          10

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cgacagctcg                                                          10

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgacctggct                                                          10

<210> SEQ ID NO 100
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ttcatagccc                                                          10

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cccaagagaa                                                          10

<210> SEQ ID NO 102
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aaacgaagta                                                          10

<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gacgtttaca                                                          10

<210> SEQ ID NO 104
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gatcgatttg                                                          10

<210> SEQ ID NO 105
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cactgtcacc                                                          10

<210> SEQ ID NO 106
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgtgagagtt                                                          10

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gacgtaacct                                                          10

<210> SEQ ID NO 108
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cagactctgc                                                          10

```
<210> SEQ ID NO 109
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tatgccaata                                                          10

<210> SEQ ID NO 110
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
acaggtgatg                                                          10

<210> SEQ ID NO 111
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtcatcgcgt                                                          10

<210> SEQ ID NO 112
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tcttataaac                                                          10

<210> SEQ ID NO 113
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtgtagactg                                                          10

<210> SEQ ID NO 114
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aaacaaccgg                                                          10
```

```
<210> SEQ ID NO 115
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atcctgtacc                                                          10

<210> SEQ ID NO 116
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ttataagaat                                                          10

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ataagtaggc                                                          10

<210> SEQ ID NO 118
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tctcgtaagg                                                          10

<210> SEQ ID NO 119
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gatccgccgc                                                          10

<210> SEQ ID NO 120
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tgtcaggttt                                                          10

<210> SEQ ID NO 121
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tccgaagccc                                                                10

<210> SEQ ID NO 122
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tccatgtcca                                                                10

<210> SEQ ID NO 123
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtgatggtac                                                                10

<210> SEQ ID NO 124
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctccacatac                                                                10

<210> SEQ ID NO 125
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ttcggatgag                                                                10

<210> SEQ ID NO 126
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
acgacatcgc                                                                10

<210> SEQ ID NO 127
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gagatgcaca                                                          10

<210> SEQ ID NO 128
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tttgtatggc                                                          10

<210> SEQ ID NO 129
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cttttctaga                                                          10

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agtctaatca                                                          10

<210> SEQ ID NO 131
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gacttagcca                                                          10

<210> SEQ ID NO 132
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tatcacagta                                                          10

<210> SEQ ID NO 133
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 133
aagctcgagt                                                              10

<210> SEQ ID NO 134
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tgttacgaca                                                              10

<210> SEQ ID NO 135
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aaggatagtc                                                              10

<210> SEQ ID NO 136
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gcacttagcc                                                              10

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gagggatccg                                                              10

<210> SEQ ID NO 138
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
attctagaag                                                              10

<210> SEQ ID NO 139
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 139
gataactgat                                                           10

<210> SEQ ID NO 140
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
atctgactgt                                                           10

<210> SEQ ID NO 141
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
caaagcgaac                                                           10

<210> SEQ ID NO 142
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gaaattgcga                                                           10

<210> SEQ ID NO 143
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gggtccagtc                                                           10

<210> SEQ ID NO 144
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
atcaggtagc                                                           10

<210> SEQ ID NO 145
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 145
gaaaggtcct                                                              10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggctaccaca                                                              10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ttattgctga                                                              10

<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
cgccgcgttt                                                              10

<210> SEQ ID NO 149
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ttttcaaaag                                                              10

<210> SEQ ID NO 150
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ctgggctaaa                                                              10

<210> SEQ ID NO 151
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 151
cccgatgaga                                                          10

<210> SEQ ID NO 152
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tgggaaatat                                                          10

<210> SEQ ID NO 153
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gtacgagcgg                                                          10

<210> SEQ ID NO 154
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcgtgcagct                                                          10

<210> SEQ ID NO 155
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
agtctgcgga                                                          10

<210> SEQ ID NO 156
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
taactattta                                                          10

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gagttgccgg                                                                 10

<210> SEQ ID NO 158
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cagcccggcg                                                                 10

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tcacctacat                                                                 10

<210> SEQ ID NO 160
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
agtggctaac                                                                 10

<210> SEQ ID NO 161
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
agaatgtgag                                                                 10

<210> SEQ ID NO 162
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tagtttcgca                                                                 10

<210> SEQ ID NO 163
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 163
cttcatttct                                                            10

<210> SEQ ID NO 164
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gccatgatat                                                            10

<210> SEQ ID NO 165
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
acggcaaatc                                                            10

<210> SEQ ID NO 166
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atcgatagta                                                            10

<210> SEQ ID NO 167
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cctaaaggca                                                            10

<210> SEQ ID NO 168
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tacgagcggt                                                            10

<210> SEQ ID NO 169
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
```

-continued tttgtcgtcg                                                          10

<210> SEQ ID NO 170
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tacaagcttg                                                          10

<210> SEQ ID NO 171
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaccaacacg                                                          10

<210> SEQ ID NO 172
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gaacgacgaa                                                          10

<210> SEQ ID NO 173
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tcggaacgca                                                          10

<210> SEQ ID NO 174
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
atccggtggt                                                          10

<210> SEQ ID NO 175
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
taaaacgtag                                                          10

<210> SEQ ID NO 176
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tatgtgagcc                                                          10

<210> SEQ ID NO 177
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gaggcatcga                                                          10

<210> SEQ ID NO 178
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gaatgggtgg                                                          10

<210> SEQ ID NO 179
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aacgacacaa                                                          10

<210> SEQ ID NO 180
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gtacgatgca                                                          10

<210> SEQ ID NO 181
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agaaggcgcc                                                          10

<210> SEQ ID NO 182
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ccgcaatgga                                                           10

<210> SEQ ID NO 183
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tacggatttt                                                           10

<210> SEQ ID NO 184
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gtcgttagct                                                           10

<210> SEQ ID NO 185
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggactagggc                                                           10

<210> SEQ ID NO 186
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
attggtattc                                                           10

<210> SEQ ID NO 187
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atcccagaga                                                           10

<210> SEQ ID NO 188
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gtcccagctc                                                              10

<210> SEQ ID NO 189
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cacgaggaat                                                              10

<210> SEQ ID NO 190
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tacaattgca                                                              10

<210> SEQ ID NO 191
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
attcctgaat                                                              10

<210> SEQ ID NO 192
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tagcgaggcg                                                              10

<210> SEQ ID NO 193
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctggatgggc                                                              10

```
<210> SEQ ID NO 194
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gcgacggcca                                                            10

<210> SEQ ID NO 195
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
acctgcacaa                                                            10

<210> SEQ ID NO 196
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
catgacagac                                                            10

<210> SEQ ID NO 197
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ttaccaacgt                                                            10

<210> SEQ ID NO 198
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
caggtgtgtg                                                            10

<210> SEQ ID NO 199
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cgagggacgg                                                            10

<210> SEQ ID NO 200
```

-continued

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cgtctcggta                                                          10

<210> SEQ ID NO 201
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
taagctatct                                                          10

<210> SEQ ID NO 202
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tactcccta                                                           10

<210> SEQ ID NO 203
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ttatattcat                                                          10

<210> SEQ ID NO 204
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
agcgatctgc                                                          10

<210> SEQ ID NO 205
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tcttctgatc                                                          10

<210> SEQ ID NO 206
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
atagttccca                                                           10

<210> SEQ ID NO 207
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tttacgggtg                                                           10

<210> SEQ ID NO 208
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gtgtcccctg                                                           10

<210> SEQ ID NO 209
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209 gcggggggtcg                                                          10

<210> SEQ ID NO 210
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cattgatcta                                                           10

<210> SEQ ID NO 211
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
agggacggtg                                                           10

<210> SEQ ID NO 212
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 212
cagttacttt                                                          10

<210> SEQ ID NO 213
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ccatacttcc                                                          10

<210> SEQ ID NO 214
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
atcagaatta                                                          10

<210> SEQ ID NO 215
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
aaactaggca                                                          10

<210> SEQ ID NO 216
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
aatgtcgttg                                                          10

<210> SEQ ID NO 217
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cacatgggtc                                                          10

<210> SEQ ID NO 218
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 218
ggtcgctggt                                                          10

<210> SEQ ID NO 219
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
actgtattac                                                          10

<210> SEQ ID NO 220
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ccgagacgcg                                                          10

<210> SEQ ID NO 221
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
actccaaccc                                                          10

<210> SEQ ID NO 222
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
atattacaag                                                          10

<210> SEQ ID NO 223
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ccatggatag                                                          10

<210> SEQ ID NO 224
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 224
ccgtctcaat                                                              10

<210> SEQ ID NO 225
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gatcgtcggg                                                              10

<210> SEQ ID NO 226
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tcttgttttg                                                              10

<210> SEQ ID NO 227
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
aatattgctc                                                              10

<210> SEQ ID NO 228
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aacgtcgtct                                                              10

<210> SEQ ID NO 229
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
aatatttttg                                                              10

<210> SEQ ID NO 230
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 230
cgtaacgtgc                                                              10

<210> SEQ ID NO 231
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcgtggttat                                                              10

<210> SEQ ID NO 232
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
caaaacatta                                                              10

<210> SEQ ID NO 233
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
cgtatcctga                                                              10

<210> SEQ ID NO 234
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tcgcttacaa                                                              10

<210> SEQ ID NO 235
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tccattgtgt                                                              10

<210> SEQ ID NO 236
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 236
gcccccattc                                                          10

<210> SEQ ID NO 237
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tgacgtctat                                                          10

<210> SEQ ID NO 238
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tgggccgagg                                                          10

<210> SEQ ID NO 239
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
aagtgtcaag                                                          10

<210> SEQ ID NO 240
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gacagtagag                                                          10

<210> SEQ ID NO 241
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cgcagccatc                                                          10

<210> SEQ ID NO 242
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 242
gaggcagaac                                                            10

<210> SEQ ID NO 243
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gttgaaattg                                                            10

<210> SEQ ID NO 244
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
atctgataaa                                                            10

<210> SEQ ID NO 245
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
agctgtctct                                                            10

<210> SEQ ID NO 246
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ttttaggtta                                                            10

<210> SEQ ID NO 247
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tatctgtccg                                                            10

<210> SEQ ID NO 248
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
```
aaaacatatg                                                            10

<210> SEQ ID NO 249
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gtaaagaaga                                                            10

<210> SEQ ID NO 250
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tcgacgtgca                                                            10

<210> SEQ ID NO 251
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tagatcttaa                                                            10

<210> SEQ ID NO 252
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cactggtcac                                                            10

<210> SEQ ID NO 253
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
attctgatgt                                                            10

<210> SEQ ID NO 254
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254

```
atggccctga                                                            10

<210> SEQ ID NO 255
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggtgatgaga                                                            10

<210> SEQ ID NO 256
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
caccgtgggg                                                            10

<210> SEQ ID NO 257
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gcttgctcgg                                                            10

<210> SEQ ID NO 258
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ccagttgaac                                                            10

<210> SEQ ID NO 259
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cgtctgtacc                                                            10

<210> SEQ ID NO 260
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ccaacgcggc                                                            10
```

<210> SEQ ID NO 261
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
acgtgatcga                                                            10

<210> SEQ ID NO 262
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ccatcgaatc                                                            10

<210> SEQ ID NO 263
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
cggtgtctgc                                                            10

<210> SEQ ID NO 264
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
aaaccacctc                                                            10

<210> SEQ ID NO 265
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tcaatgttcc                                                            10

<210> SEQ ID NO 266
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ttcgacatgt                                                            10

```
<210> SEQ ID NO 267
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
aggcacgata                                                              10

<210> SEQ ID NO 268
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cacgagatca                                                              10

<210> SEQ ID NO 269
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
catgctgggg                                                              10

<210> SEQ ID NO 270
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
taccatggtt                                                              10

<210> SEQ ID NO 271
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ttgcccatat                                                              10

<210> SEQ ID NO 272
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tgcacattcg                                                              10
```

```
<210> SEQ ID NO 273
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gttatgttgg                                                          10

<210> SEQ ID NO 274
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tgagttatga                                                          10

<210> SEQ ID NO 275
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gatggccccc                                                          10

<210> SEQ ID NO 276
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gatgggttac                                                          10

<210> SEQ ID NO 277
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
agctacgttg                                                          10

<210> SEQ ID NO 278
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
accccatgca                                                          10

<210> SEQ ID NO 279
```

<210> SEQ ID NO 279
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tactaccgtt                                                              10

<210> SEQ ID NO 280
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tcgcttctac                                                              10

<210> SEQ ID NO 281
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ctggcagtgc                                                              10

<210> SEQ ID NO 282
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tctatatata                                                              10

<210> SEQ ID NO 283
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggattagttc                                                              10

<210> SEQ ID NO 284
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gtgttacgct                                                              10

<210> SEQ ID NO 285
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tcgactccgt                                                          10

<210> SEQ ID NO 286
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggtagcaggc                                                          10

<210> SEQ ID NO 287
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tattggattc                                                          10

<210> SEQ ID NO 288
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gttcgatcga                                                          10

<210> SEQ ID NO 289
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
atattaatat                                                          10

<210> SEQ ID NO 290
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
agaacgattg                                                          10

<210> SEQ ID NO 291
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 291
gtaaagtgta                                                          10

<210> SEQ ID NO 292
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cccatgtgcc                                                          10

<210> SEQ ID NO 293
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gtggcctcgc                                                          10

<210> SEQ ID NO 294
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gacactagga                                                          10

<210> SEQ ID NO 295
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
atattctgac                                                          10

<210> SEQ ID NO 296
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
taagtagacg                                                          10

<210> SEQ ID NO 297
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
taacggtcta                                                              10

<210> SEQ ID NO 298
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tagtttcatt                                                              10

<210> SEQ ID NO 299
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ttggatccga                                                              10

<210> SEQ ID NO 300
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cgtgacaacc                                                              10

<210> SEQ ID NO 301
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cgcgctcaga                                                              10

<210> SEQ ID NO 302
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
cgttcttaat                                                              10

<210> SEQ ID NO 303
<211> LENGTH: 10
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 303
acaagagttt                                                            10

<210> SEQ ID NO 304
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304
agggttatag                                                            10

<210> SEQ ID NO 305
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
accacgactc                                                            10

<210> SEQ ID NO 306
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
gtactcgggg                                                            10

<210> SEQ ID NO 307
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
acaaatatct                                                            10

<210> SEQ ID NO 308
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
gatcggggtg                                                            10

<210> SEQ ID NO 309
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
atgtaactcc                                                                 10

<210> SEQ ID NO 310
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
atgaagaagc                                                                 10

<210> SEQ ID NO 311
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
atgtattgtc                                                                 10

<210> SEQ ID NO 312
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tgcattggaa                                                                 10

<210> SEQ ID NO 313
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gcggacgatc                                                                 10

<210> SEQ ID NO 314
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ccgtacttga                                                                 10

<210> SEQ ID NO 315
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 315
tttgcccccg                                                          10

<210> SEQ ID NO 316
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
acctcacgcg                                                          10

<210> SEQ ID NO 317
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
attaaggggc                                                          10

<210> SEQ ID NO 318
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
cgtggacatg                                                          10

<210> SEQ ID NO 319
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ttagcccttc                                                          10

<210> SEQ ID NO 320
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cgagagtttg                                                          10

<210> SEQ ID NO 321
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 321
tgcatcctct                                                          10

<210> SEQ ID NO 322
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgcgattccg                                                          10

<210> SEQ ID NO 323
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ttattacgtt                                                          10

<210> SEQ ID NO 324
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tgatgtggtt                                                          10

<210> SEQ ID NO 325
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gggcgtcaat                                                          10

<210> SEQ ID NO 326
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
cccttgaaat                                                          10

<210> SEQ ID NO 327
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
```
tctttggggc                                                              10

<210> SEQ ID NO 328
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
accggcaggc                                                              10

<210> SEQ ID NO 329
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gctaaaatct                                                              10

<210> SEQ ID NO 330
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gccgttgacg                                                              10

<210> SEQ ID NO 331
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ggagttgttg                                                              10

<210> SEQ ID NO 332
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tacttgagaa                                                              10

<210> SEQ ID NO 333
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
cgggtgcgct                                                          10

<210> SEQ ID NO 334
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
aaaagcgtct                                                          10

<210> SEQ ID NO 335
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gtaaagatag                                                          10

<210> SEQ ID NO 336
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gcctggtcag                                                          10

<210> SEQ ID NO 337
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggcaaaaagg                                                          10

<210> SEQ ID NO 338
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
acccttctct                                                          10

<210> SEQ ID NO 339
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tcacatagtg                                                          10

<210> SEQ ID NO 340
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tcgtctgtgc                                                          10

<210> SEQ ID NO 341
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
tgctcggatc                                                          10

<210> SEQ ID NO 342
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
agcagtcccg                                                          10

<210> SEQ ID NO 343
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tttgggctgt                                                          10

<210> SEQ ID NO 344
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ctcacgatct                                                          10

<210> SEQ ID NO 345
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tggcgcatac                                                          10

<210> SEQ ID NO 346
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 346
gcaattgaaa                                                          10

<210> SEQ ID NO 347
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 347
tcgggagacg                                                          10

<210> SEQ ID NO 348
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 348
cccggcgaaa                                                          10

<210> SEQ ID NO 349
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 349
tgatgcggaa                                                          10

<210> SEQ ID NO 350
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 350
aactgaggcg                                                          10

<210> SEQ ID NO 351
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 351
catattattt                                                          10

```
<210> SEQ ID NO 352
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
aaaagtcatt                                                                10

<210> SEQ ID NO 353
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
aagcggtgag                                                                10

<210> SEQ ID NO 354
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aaggtaatca                                                                10

<210> SEQ ID NO 355
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ctgacactta                                                                10

<210> SEQ ID NO 356
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ctgttttcta                                                                10

<210> SEQ ID NO 357
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
cacatggcag                                                                10

<210> SEQ ID NO 358
```

<210> SEQ ID NO 358
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ttcaatccgg                                                              10

<210> SEQ ID NO 359
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tgtccggcat                                                              10

<210> SEQ ID NO 360
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
tggtaccgtg                                                              10

<210> SEQ ID NO 361
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
aagagatatt                                                              10

<210> SEQ ID NO 362
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gatgtactac                                                              10

<210> SEQ ID NO 363
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gaaatggaat                                                              10

<210> SEQ ID NO 364
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ttaaaatact                                                             10

<210> SEQ ID NO 365
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tgaccggaac                                                             10

<210> SEQ ID NO 366
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gtcgccgcaa                                                             10

<210> SEQ ID NO 367
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
taggataccg                                                             10

<210> SEQ ID NO 368
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
agtccaattg                                                             10

<210> SEQ ID NO 369
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gggggctata                                                             10

<210> SEQ ID NO 370
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 370 accttcagtt					10

<210> SEQ ID NO 371
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371 atggcaagta					10

<210> SEQ ID NO 372
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372 agaatgtttt					10

<210> SEQ ID NO 373
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373 agttcgtttg					10

<210> SEQ ID NO 374
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374 cactactgac					10

<210> SEQ ID NO 375
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375 gatcaagagc					10

<210> SEQ ID NO 376
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
atttatcgag                                                          10

<210> SEQ ID NO 377
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
cctttttcca                                                          10

<210> SEQ ID NO 378
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gcacagaggt                                                          10

<210> SEQ ID NO 379
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
tgatctgaat                                                          10

<210> SEQ ID NO 380
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gttggaggga                                                          10

<210> SEQ ID NO 381
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ttttgaaggt                                                          10

<210> SEQ ID NO 382
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 382
taagtcctaa                                                              10

<210> SEQ ID NO 383
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ggtgttaggg                                                              10

<210> SEQ ID NO 384
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
tgtatgcacc                                                              10

<210> SEQ ID NO 385
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
ccgtgccatt                                                              10

<210> SEQ ID NO 386
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gaaatcaccc                                                              10

<210> SEQ ID NO 387
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
tttgcacgtg                                                              10

<210> SEQ ID NO 388
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 388
cgtctgtttt                                                              10

<210> SEQ ID NO 389
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
ctacaccaca                                                              10

<210> SEQ ID NO 390
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tgctacaggg                                                              10

<210> SEQ ID NO 391
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gggaatatat                                                              10

<210> SEQ ID NO 392
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tcatgtattt                                                              10

<210> SEQ ID NO 393
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tctccgttta                                                              10

<210> SEQ ID NO 394
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 394
tacctctcgc                                                                    10

<210> SEQ ID NO 395
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcttcaaccg                                                                    10

<210> SEQ ID NO 396
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
atgaagctac                                                                    10

<210> SEQ ID NO 397
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
cggtacaact                                                                    10

<210> SEQ ID NO 398
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gtgtggtcgt                                                                    10

<210> SEQ ID NO 399
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ggggtcatgt                                                                    10

<210> SEQ ID NO 400
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 400
aggcagccca                                                              10

<210> SEQ ID NO 401
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
caagcacgat                                                              10

<210> SEQ ID NO 402
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tcaaatggat                                                              10

<210> SEQ ID NO 403
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
ggactgaata                                                              10

<210> SEQ ID NO 404
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ccgtagacgt                                                              10

<210> SEQ ID NO 405
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
cggcgtaccg                                                              10

<210> SEQ ID NO 406
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
```
ggcggcgccc                                                         10

<210> SEQ ID NO 407
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
agacttgatc                                                         10

<210> SEQ ID NO 408
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
accttgcaca                                                         10

<210> SEQ ID NO 409
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
taaggtgagt                                                         10

<210> SEQ ID NO 410
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
ttgttgtttc                                                         10

<210> SEQ ID NO 411
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gagggaatac                                                         10

<210> SEQ ID NO 412
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ctcgtacgcg                                                              10

<210> SEQ ID NO 413
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ccgcggttta                                                              10

<210> SEQ ID NO 414
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ttaaagttaa                                                              10

<210> SEQ ID NO 415
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gcatatgggt                                                              10

<210> SEQ ID NO 416
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
agtctgagcc                                                              10

<210> SEQ ID NO 417
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tgtcggttcg                                                              10

<210> SEQ ID NO 418
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ggtctcaacc                                                              10

<210> SEQ ID NO 419
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
gtaacggcat                                                          10

<210> SEQ ID NO 420
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
acactgagaa                                                          10

<210> SEQ ID NO 421
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
cccaacgtcg                                                          10

<210> SEQ ID NO 422
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
aagaaactgc                                                          10

<210> SEQ ID NO 423
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
accagcccac                                                          10

<210> SEQ ID NO 424
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tgtagttact                                                          10

<210> SEQ ID NO 425
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
ggctagaggc                                                              10

<210> SEQ ID NO 426
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gttcggcaga                                                              10

<210> SEQ ID NO 427
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ccaaaataga                                                              10

<210> SEQ ID NO 428
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
cccatataac                                                              10

<210> SEQ ID NO 429
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
gtcactaccg                                                              10

<210> SEQ ID NO 430
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gtagtgtggc                                                              10

```
<210> SEQ ID NO 431
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
caatctcata                                                          10

<210> SEQ ID NO 432
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ccatgttata                                                          10

<210> SEQ ID NO 433
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
taagcagtgg                                                          10

<210> SEQ ID NO 434
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tcggcggcta                                                          10

<210> SEQ ID NO 435
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
tattaaatgc                                                          10

<210> SEQ ID NO 436
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
gtcgccatta                                                          10

<210> SEQ ID NO 437
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ggcgtcgttc                                                         10

<210> SEQ ID NO 438
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
ctagtagata                                                         10

<210> SEQ ID NO 439
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tcgtcagtat                                                         10

<210> SEQ ID NO 440
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
ggggtatcgg                                                         10

<210> SEQ ID NO 441
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
tgctctgcca                                                         10

<210> SEQ ID NO 442
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
tgccgtaact                                                         10

<210> SEQ ID NO 443
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
cggtacaggc                                                            10

<210> SEQ ID NO 444
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tcctaatttg                                                            10

<210> SEQ ID NO 445
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tctttctgga                                                            10

<210> SEQ ID NO 446
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ccgcgacttg                                                            10

<210> SEQ ID NO 447
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
acctatagcg                                                            10

<210> SEQ ID NO 448
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
gccggcacct                                                            10

<210> SEQ ID NO 449
<211> LENGTH: 10
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 449
tttgataggc                                                              10

<210> SEQ ID NO 450
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
actgtgagct                                                              10

<210> SEQ ID NO 451
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ttatcgttca                                                              10

<210> SEQ ID NO 452
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
actagtggcc                                                              10

<210> SEQ ID NO 453
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cctccgtggt                                                              10

<210> SEQ ID NO 454
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
ttagggtatg                                                              10

<210> SEQ ID NO 455
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 455
gaatcaggcg                                                                10

<210> SEQ ID NO 456
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ggctgaccaa                                                                10

<210> SEQ ID NO 457
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
tgccagaccg                                                                10

<210> SEQ ID NO 458
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
tccctacgcg                                                                10

<210> SEQ ID NO 459
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
tccgctggag                                                                10

<210> SEQ ID NO 460
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ggatcaaaac                                                                10

<210> SEQ ID NO 461
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 461
ttcacctcac                                                              10

<210> SEQ ID NO 462
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gacacacggc                                                              10

<210> SEQ ID NO 463
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tgggcgatta                                                              10

<210> SEQ ID NO 464
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
taagatcttc                                                              10

<210> SEQ ID NO 465
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
ctccgactac                                                              10

<210> SEQ ID NO 466
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gggccatcat                                                              10

<210> SEQ ID NO 467
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 467
tcaggccaga                                                              10

<210> SEQ ID NO 468
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
cttgtggggc                                                              10

<210> SEQ ID NO 469
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
agatagtctg                                                              10

<210> SEQ ID NO 470
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gcgtcaaagt                                                              10

<210> SEQ ID NO 471
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
acgaaaattt                                                              10

<210> SEQ ID NO 472
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gagtctggtg                                                              10

<210> SEQ ID NO 473
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 473
atcgagcgac                                                            10

<210> SEQ ID NO 474
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ggtcctcaga                                                            10

<210> SEQ ID NO 475
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tgattttgtc                                                            10

<210> SEQ ID NO 476
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gcatttctca                                                            10

<210> SEQ ID NO 477
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gcatgccagt                                                            10

<210> SEQ ID NO 478
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
attagacgac                                                            10

<210> SEQ ID NO 479
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 479
aaagcccata                                                            10

<210> SEQ ID NO 480
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
cactacattc                                                            10

<210> SEQ ID NO 481
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
cacggtttct                                                            10

<210> SEQ ID NO 482
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
cccaccagtg                                                            10

<210> SEQ ID NO 483
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
ctcacttgtc                                                            10

<210> SEQ ID NO 484
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gatagactct                                                            10

<210> SEQ ID NO 485
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
```
atttccattt                                                          10

<210> SEQ ID NO 486
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
atatgtggcc                                                          10

<210> SEQ ID NO 487
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
cgggacgaac                                                          10

<210> SEQ ID NO 488
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
agaaccgtga                                                          10

<210> SEQ ID NO 489
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tagtgtactg                                                          10

<210> SEQ ID NO 490
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
aactaatcga                                                          10

<210> SEQ ID NO 491
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
cgaagtgacg                                                               10

<210> SEQ ID NO 492
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
cggagcctcg                                                               10

<210> SEQ ID NO 493
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
atcacacgag                                                               10

<210> SEQ ID NO 494
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
cgacgagttc                                                               10

<210> SEQ ID NO 495
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
gcttcccgtg                                                               10

<210> SEQ ID NO 496
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
gattcatacc                                                               10

<210> SEQ ID NO 497
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
gagagaagcg                                                               10

<210> SEQ ID NO 498
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
gaagtggcct                                                              10

<210> SEQ ID NO 499
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ggacgacgcc                                                              10

<210> SEQ ID NO 500
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tagggtctca                                                              10

<210> SEQ ID NO 501
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
aactacaggt                                                              10

<210> SEQ ID NO 502
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gtggcctgtg                                                              10

<210> SEQ ID NO 503
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
ctttaccagc                                                              10

<210> SEQ ID NO 504
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
cgcgttactg                                                                10

<210> SEQ ID NO 505
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
ttgctcccgt                                                                10

<210> SEQ ID NO 506
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
catcaaacaa                                                                10

<210> SEQ ID NO 507
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gctttatgat                                                                10

<210> SEQ ID NO 508
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ctgcatactg                                                                10

<210> SEQ ID NO 509
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
ggtggctcag                                                                10

```
<210> SEQ ID NO 510
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
ggacgatcaa                                                          10

<210> SEQ ID NO 511
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
ccgactggtg                                                          10

<210> SEQ ID NO 512
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
ggaacaaccg                                                          10

<210> SEQ ID NO 513
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
gaacgagacc                                                          10

<210> SEQ ID NO 514
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
caccaagaaa                                                          10

<210> SEQ ID NO 515
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
atgcattacc                                                          10

<210> SEQ ID NO 516
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
gtatcatgcc                                                             10

<210> SEQ ID NO 517
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
agtagatgtt                                                             10

<210> SEQ ID NO 518
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ctctagatgt                                                             10

<210> SEQ ID NO 519
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
gctacttgtg                                                             10

<210> SEQ ID NO 520
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
tatgaaacgt                                                             10

<210> SEQ ID NO 521
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
cctcgttgat                                                             10

<210> SEQ ID NO 522
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ctagagccat                                                              10

<210> SEQ ID NO 523
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
tagagttata                                                              10

<210> SEQ ID NO 524
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
aacgagaggc                                                              10

<210> SEQ ID NO 525
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ggtctaccgt                                                              10

<210> SEQ ID NO 526
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gcccctcac                                                               10

<210> SEQ ID NO 527
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
cataggaatt                                                              10

<210> SEQ ID NO 528
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 528
tccggctcgt                                                            10

<210> SEQ ID NO 529
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tgagagtcgg                                                            10

<210> SEQ ID NO 530
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
cgtagaaata                                                            10

<210> SEQ ID NO 531
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ctttacatga                                                            10

<210> SEQ ID NO 532
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gagcgccgtc                                                            10

<210> SEQ ID NO 533
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
ggctctcggc                                                            10

<210> SEQ ID NO 534
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 534
agagcttgtt                                                            10

<210> SEQ ID NO 535
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
aatcagccac                                                            10

<210> SEQ ID NO 536
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
agaagagcca                                                            10

<210> SEQ ID NO 537
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
tcgtatgagt                                                            10

<210> SEQ ID NO 538
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ttcttcctcg                                                            10

<210> SEQ ID NO 539
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
acacaaaagc                                                            10

<210> SEQ ID NO 540
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 540
cgcgggaccc                                                          10

<210> SEQ ID NO 541
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
gtcgcgacac                                                          10

<210> SEQ ID NO 542
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
ccggaggaaa                                                          10

<210> SEQ ID NO 543
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
cggcgtatga                                                          10

<210> SEQ ID NO 544
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
taggcattct                                                          10

<210> SEQ ID NO 545
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
aaaggaggga                                                          10

<210> SEQ ID NO 546
<211> LENGTH: 10
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 546
acctttacgg                                                          10

<210> SEQ ID NO 547
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ctaccgttaa                                                          10

<210> SEQ ID NO 548
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gagcttcgcc                                                          10

<210> SEQ ID NO 549
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
gccatagaag                                                          10

<210> SEQ ID NO 550
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tttagcgtat                                                          10

<210> SEQ ID NO 551
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
gcaaacagat                                                          10

<210> SEQ ID NO 552
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 552
taggtcatgg                                                          10

<210> SEQ ID NO 553
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
ctctaacaga                                                          10

<210> SEQ ID NO 554
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ggctcatgaa                                                          10

<210> SEQ ID NO 555
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
caatgtctca                                                          10

<210> SEQ ID NO 556
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
tgatcgtatt                                                          10

<210> SEQ ID NO 557
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
gcgcttttca                                                          10

<210> SEQ ID NO 558
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 558
aagattatat                                                              10

<210> SEQ ID NO 559
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
actagctgac                                                              10

<210> SEQ ID NO 560
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ggtgagctca                                                              10

<210> SEQ ID NO 561
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
cgctttcgct                                                              10

<210> SEQ ID NO 562
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
tgattcaaaa                                                              10

<210> SEQ ID NO 563
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
actgaacagg                                                              10

<210> SEQ ID NO 564
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
```
attcgagcta            10

<210> SEQ ID NO 565
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
tgtaggctaa            10

<210> SEQ ID NO 566
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
acaaagcttt            10

<210> SEQ ID NO 567
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
gcccgaggga            10

<210> SEQ ID NO 568
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
gcccgctggg            10

<210> SEQ ID NO 569
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
accccgctga            10

<210> SEQ ID NO 570
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
cttatgccct 10

<210> SEQ ID NO 571
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
ccgccatagc 10

<210> SEQ ID NO 572
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
cttaatgatt 10

<210> SEQ ID NO 573
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
cagtccacaa 10

<210> SEQ ID NO 574
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
atggacggac 10

<210> SEQ ID NO 575
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
cggcctctcg 10

<210> SEQ ID NO 576
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
tagtcgccat 10

<210> SEQ ID NO 577
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
gttgatcttc                                                          10

<210> SEQ ID NO 578
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
acttgccaag                                                          10

<210> SEQ ID NO 579
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
atgactggtt                                                          10

<210> SEQ ID NO 580
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
tgtcgtagga                                                          10

<210> SEQ ID NO 581
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
agcaaacacg                                                          10

<210> SEQ ID NO 582
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tactgatgaa                                                          10

```
<210> SEQ ID NO 583
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
gtatcccata                                                          10

<210> SEQ ID NO 584
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
tagccaggtt                                                          10

<210> SEQ ID NO 585
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
cgtgtggcga                                                          10

<210> SEQ ID NO 586
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
atcgaattgc                                                          10

<210> SEQ ID NO 587
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
ccccaatatt                                                          10

<210> SEQ ID NO 588
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
cccgtttctc                                                          10
```

```
<210> SEQ ID NO 589
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
tccgcatcta                                                          10

<210> SEQ ID NO 590
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
caagcctcat                                                          10

<210> SEQ ID NO 591
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
tttcaatccc                                                          10

<210> SEQ ID NO 592
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
ccttcccatc                                                          10

<210> SEQ ID NO 593
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
aggtacaaga                                                          10

<210> SEQ ID NO 594
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
gtgtaatgga                                                          10

<210> SEQ ID NO 595
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
aaactgagct                                                           10

<210> SEQ ID NO 596
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
atctctgccc                                                           10

<210> SEQ ID NO 597
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
cgacatttgc                                                           10

<210> SEQ ID NO 598
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
tgtgaacccg                                                           10

<210> SEQ ID NO 599
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tgacacccca                                                           10

<210> SEQ ID NO 600
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
taggccaaag                                                           10

<210> SEQ ID NO 601
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
gaaattgtag                                                              10

<210> SEQ ID NO 602
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
gcgtctgatt                                                              10

<210> SEQ ID NO 603
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
tctcattgtt                                                              10

<210> SEQ ID NO 604
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ctgacatctc                                                              10

<210> SEQ ID NO 605
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
gtatccagtg                                                              10

<210> SEQ ID NO 606
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
gatggccgtt                                                              10

<210> SEQ ID NO 607
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 607
tcaccctctc                                                          10

<210> SEQ ID NO 608
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
ggcactattc                                                          10

<210> SEQ ID NO 609
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
aaataactgt                                                          10

<210> SEQ ID NO 610
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
cagctccatt                                                          10

<210> SEQ ID NO 611
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ctcttgactc                                                          10

<210> SEQ ID NO 612
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
tttcctatac                                                          10

<210> SEQ ID NO 613
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ccatacccga                                                                10

<210> SEQ ID NO 614
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
tcgccgagcg                                                                10

<210> SEQ ID NO 615
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
cgctgaagcc                                                                10

<210> SEQ ID NO 616
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
tctggcccca                                                                10

<210> SEQ ID NO 617
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
gctacattga                                                                10

<210> SEQ ID NO 618
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
cgcatcataa                                                                10

<210> SEQ ID NO 619
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 619
gcaaagggcc                                                              10

<210> SEQ ID NO 620
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
aacggcgcag                                                              10

<210> SEQ ID NO 621
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
cgactgacat                                                              10

<210> SEQ ID NO 622
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
atgacagggc                                                              10

<210> SEQ ID NO 623
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
caagttctcc                                                              10

<210> SEQ ID NO 624
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
tcgccgcttt                                                              10

<210> SEQ ID NO 625
<211> LENGTH: 10
<212> TYPE: DNA
<213> ORGANISM: Artificial Sequence
<220> FEATURE:
<223> OTHER INFORMATION: Description of Artificial Sequence: Synthetic
```

```
            oligonucleotide

<400> SEQUENCE: 625
atgccggaaa                                                          10

<210> SEQ ID NO 626
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
gcggttacta                                                          10

<210> SEQ ID NO 627
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
gacattacaa                                                          10

<210> SEQ ID NO 628
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
cagagagggc                                                          10

<210> SEQ ID NO 629
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gcaccgcctc                                                          10

<210> SEQ ID NO 630
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
cggtccgagc                                                          10

<210> SEQ ID NO 631
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 631
tgtccggtgc                                                                10

<210> SEQ ID NO 632
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
ggtcggttgc                                                                10

<210> SEQ ID NO 633
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
gctcagctaa                                                                10

<210> SEQ ID NO 634
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
agcagttcgt                                                                10

<210> SEQ ID NO 635
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
aaatcgatga                                                                10

<210> SEQ ID NO 636
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
gctcggtatg                                                                10

<210> SEQ ID NO 637
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 637
cccgccgcgg                                                              10

<210> SEQ ID NO 638
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
gtgtgatagg                                                              10

<210> SEQ ID NO 639
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
ttggactcca                                                              10

<210> SEQ ID NO 640
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tgcttatcta                                                              10

<210> SEQ ID NO 641
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
caaaaggcgt                                                              10

<210> SEQ ID NO 642
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
taggggcct                                                               10

<210> SEQ ID NO 643
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
```

-continued aagtattaat 10

<210> SEQ ID NO 644
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
gtttagcccg 10

<210> SEQ ID NO 645
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
cgctaatatg 10

<210> SEQ ID NO 646
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
acaacacgtt 10

<210> SEQ ID NO 647
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
agagatgctc 10

<210> SEQ ID NO 648
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
tgcctgatat 10

<210> SEQ ID NO 649
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
cttgtaagta                                                           10

<210> SEQ ID NO 650
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
catattgccg                                                           10

<210> SEQ ID NO 651
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
cttagaaagt                                                           10

<210> SEQ ID NO 652
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
atgttgtatt                                                           10

<210> SEQ ID NO 653
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
cgcattgaag                                                           10

<210> SEQ ID NO 654
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ttatgttggt                                                           10

<210> SEQ ID NO 655
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
tcgcctcaga                                                           10

<210> SEQ ID NO 656
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 656
ttcgttgagg    10

<210> SEQ ID NO 657
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 657
ggtgccgggc    10

<210> SEQ ID NO 658
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 658
accattgtaa    10

<210> SEQ ID NO 659
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 659
ttgattgtca    10

<210> SEQ ID NO 660
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 660
cggctcacct    10

<210> SEQ ID NO 661
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 661
ctatcacatg    10

<210> SEQ ID NO 662
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
gtagacagaa                                                          10

<210> SEQ ID NO 663
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
cctttaccaa                                                          10

<210> SEQ ID NO 664
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
gcacatcgac                                                          10

<210> SEQ ID NO 665
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
tctcactttc                                                          10

<210> SEQ ID NO 666
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ttcgagtact                                                          10

<210> SEQ ID NO 667
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
tagaagagca                                                          10

-continued

```
<210> SEQ ID NO 668
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
aaccccacca                                                          10

<210> SEQ ID NO 669
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
ctgtatcagt                                                          10

<210> SEQ ID NO 670
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
acataatgag                                                          10

<210> SEQ ID NO 671
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
agccttccgc                                                          10

<210> SEQ ID NO 672
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
cagtgctttt                                                          10

<210> SEQ ID NO 673
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
tagtccgtgt                                                          10

<210> SEQ ID NO 674
```

<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
cggaatcggt                                                              10

<210> SEQ ID NO 675
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
cttgcggaga                                                              10

<210> SEQ ID NO 676
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
aaaaatttgg                                                              10

<210> SEQ ID NO 677
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
tgttttccgc                                                              10

<210> SEQ ID NO 678
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
atgctaggcg                                                              10

<210> SEQ ID NO 679
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
gactaatttc                                                              10

<210> SEQ ID NO 680
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
ctgtagtaac                                                               10

<210> SEQ ID NO 681
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
cggatgactt                                                               10

<210> SEQ ID NO 682
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
tcagagtgga                                                               10

<210> SEQ ID NO 683
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
caaaatagcg                                                               10

<210> SEQ ID NO 684
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gaagaagaag                                                               10

<210> SEQ ID NO 685
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
cacccgcacg                                                               10

<210> SEQ ID NO 686
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 686
acgatgcccg                                                              10

<210> SEQ ID NO 687
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
cctactacac                                                              10

<210> SEQ ID NO 688
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
attgaaacaa                                                              10

<210> SEQ ID NO 689
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gaccgaagat                                                              10

<210> SEQ ID NO 690
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
acggcctgaa                                                              10

<210> SEQ ID NO 691
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691 agggqaggtc                                                              10

<210> SEQ ID NO 692
<211> LENGTH: 10
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 692
caatcaactt                                                              10

<210> SEQ ID NO 693
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
ggacaaccga                                                              10

<210> SEQ ID NO 694
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
tccctaaggc                                                              10

<210> SEQ ID NO 695
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
gttctacacg                                                              10

<210> SEQ ID NO 696
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
actaaccagt                                                              10

<210> SEQ ID NO 697
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
gaagctggat                                                              10

<210> SEQ ID NO 698
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 698
ggaaccatgg                                                                10

<210> SEQ ID NO 699
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
ctctacctgg                                                                10

<210> SEQ ID NO 700
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
taatgcctgc                                                                10

<210> SEQ ID NO 701
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
taaaggcaat                                                                10

<210> SEQ ID NO 702
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
cgcctgggaa                                                                10

<210> SEQ ID NO 703
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
tcttggggaa                                                                10

<210> SEQ ID NO 704
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 704
agagagagag                                                                    10

<210> SEQ ID NO 705
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
gcgttggcgc                                                                    10

<210> SEQ ID NO 706
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
ttacgacaga                                                                    10

<210> SEQ ID NO 707
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
ggaactctta                                                                    10

<210> SEQ ID NO 708
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
gattgtggag                                                                    10

<210> SEQ ID NO 709
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
gggcactgat                                                                    10

<210> SEQ ID NO 710
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 710
agacgcacca                                                              10

<210> SEQ ID NO 711
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
ccaattataa                                                              10

<210> SEQ ID NO 712
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
tagagacgca                                                              10

<210> SEQ ID NO 713
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
cctcttgtcg                                                              10

<210> SEQ ID NO 714
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
gaggaagctc                                                              10

<210> SEQ ID NO 715
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
agtcccgagt                                                              10

<210> SEQ ID NO 716
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 716
tgcttgcagt                                                          10

<210> SEQ ID NO 717
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
cccacttccc                                                          10

<210> SEQ ID NO 718
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
cgttgccgcg                                                          10

<210> SEQ ID NO 719
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
cccctggttc                                                          10

<210> SEQ ID NO 720
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
acgaccaata                                                          10

<210> SEQ ID NO 721
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
cttagggttc                                                          10

<210> SEQ ID NO 722
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
```
aaacatatca 10

<210> SEQ ID NO 723
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
gggtcgtaga 10

<210> SEQ ID NO 724
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
ctccgtagcg 10

<210> SEQ ID NO 725
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
ctggtcataa 10

<210> SEQ ID NO 726
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
ttgacagatc 10

<210> SEQ ID NO 727
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
gagtaaagtc 10

<210> SEQ ID NO 728
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
atatgggctt 10

<210> SEQ ID NO 729
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
tacaactact 10

<210> SEQ ID NO 730
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
aattcagccg 10

<210> SEQ ID NO 731
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
gattgtacta 10

<210> SEQ ID NO 732
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
tcgtaatgcg 10

<210> SEQ ID NO 733
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
cgataactgc 10

<210> SEQ ID NO 734
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
aacttggcgg 10

<210> SEQ ID NO 735
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
cgtggatgta                                                                10

<210> SEQ ID NO 736
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
ccttcccgaa                                                                10

<210> SEQ ID NO 737
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
ctaaacccgt                                                                10

<210> SEQ ID NO 738
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
caacattccc                                                                10

<210> SEQ ID NO 739
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
cttaccctct                                                                10

<210> SEQ ID NO 740
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
ggaaagttct                                                                10

```
<210> SEQ ID NO 741
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
cggattggct                                                          10

<210> SEQ ID NO 742
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
aatgtagggc                                                          10

<210> SEQ ID NO 743
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
aatgaatcgc                                                          10

<210> SEQ ID NO 744
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
atcatacacc                                                          10

<210> SEQ ID NO 745
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
agttgggcag                                                          10

<210> SEQ ID NO 746
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
agaagaaggg                                                          10
```

```
<210> SEQ ID NO 747
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
gcgtgcgcta                                                              10

<210> SEQ ID NO 748
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
ccccgataaa                                                              10

<210> SEQ ID NO 749
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
taccaagtgc                                                              10

<210> SEQ ID NO 750
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
tgtgttttcg                                                              10

<210> SEQ ID NO 751
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
cccagatgtc                                                              10

<210> SEQ ID NO 752
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gcgagcttcc                                                              10

<210> SEQ ID NO 753
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
gtgtcacgta                                                                10

<210> SEQ ID NO 754
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
ataggccgag                                                                10

<210> SEQ ID NO 755
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
gagctaccag                                                                10

<210> SEQ ID NO 756
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
cgcggcggag                                                                10

<210> SEQ ID NO 757
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
tcttgcacga                                                                10

<210> SEQ ID NO 758
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
tgccctaaag                                                                10

<210> SEQ ID NO 759
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
ttgcgctttg                                                          10

<210> SEQ ID NO 760
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
catataaagg                                                          10

<210> SEQ ID NO 761
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
aatagcgaat                                                          10

<210> SEQ ID NO 762
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
tacgctaagg                                                          10

<210> SEQ ID NO 763
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
acttagttcg                                                          10

<210> SEQ ID NO 764
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
cgtgcggaac                                                          10

<210> SEQ ID NO 765
<211> LENGTH: 10
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 765 acccgattcg					10

<210> SEQ ID NO 766
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 766 tgcagagttt					10

<210> SEQ ID NO 767
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 767 gaatcattag					10

<210> SEQ ID NO 768
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 768 agtacactgg					10

<210> SEQ ID NO 769
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 769 ttgtgcggtt					10

<210> SEQ ID NO 770
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 770 atgacatgca					10

<210> SEQ ID NO 771
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 771
ttctcggacg                                                           10

<210> SEQ ID NO 772
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
agattgaaga                                                           10

<210> SEQ ID NO 773
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
ggcggactgt                                                           10

<210> SEQ ID NO 774
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
tttatggtaa                                                           10

<210> SEQ ID NO 775
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
cagtagggtg                                                           10

<210> SEQ ID NO 776
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
gacaggcaag                                                           10

<210> SEQ ID NO 777
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 777
gatgtgtcgt                                                                10

<210> SEQ ID NO 778
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
acttgacgga                                                                10

<210> SEQ ID NO 779
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
aagtccgaaa                                                                10

<210> SEQ ID NO 780
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
tgggtgtagg                                                                10

<210> SEQ ID NO 781
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
acttaccgcg                                                                10

<210> SEQ ID NO 782
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
ctgtgcaccc                                                                10

<210> SEQ ID NO 783
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 783
attgctctct                                                            10

<210> SEQ ID NO 784
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
cagaagacaa                                                            10

<210> SEQ ID NO 785
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
ttacgctata                                                            10

<210> SEQ ID NO 786
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
acgtggaaat                                                            10

<210> SEQ ID NO 787
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
tgaggctggt                                                            10

<210> SEQ ID NO 788
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
attatgagat                                                            10

<210> SEQ ID NO 789
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
gacttgtagt                                                          10

<210> SEQ ID NO 790
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
tcgctgagga                                                          10

<210> SEQ ID NO 791
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
cccaactcta                                                          10

<210> SEQ ID NO 792
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
gatagggagg                                                          10

<210> SEQ ID NO 793
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
tagaaatcag                                                          10

<210> SEQ ID NO 794
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
gtcgctagaa                                                          10

<210> SEQ ID NO 795
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 795
aaaatagaaa                                                              10

<210> SEQ ID NO 796
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
gctcctgggt                                                              10

<210> SEQ ID NO 797
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
cgcgctcgcg                                                              10

<210> SEQ ID NO 798
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
ggcaaacgca                                                              10

<210> SEQ ID NO 799
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
tttactacct                                                              10

<210> SEQ ID NO 800
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
atcctaaact                                                              10

<210> SEQ ID NO 801
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
```

-continued ctccgtatgt                                                                10

<210> SEQ ID NO 802
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
tatcgtccag                                                                10

<210> SEQ ID NO 803
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
gccggcggta                                                                10

<210> SEQ ID NO 804
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
tgctccattt                                                                10

<210> SEQ ID NO 805
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
tggctgttgt                                                                10

<210> SEQ ID NO 806
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
tactgcgcaa                                                                10

<210> SEQ ID NO 807
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
tatacggctt                                                          10

<210> SEQ ID NO 808
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
ggttattacc                                                          10

<210> SEQ ID NO 809
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
atcaggagga                                                          10

<210> SEQ ID NO 810
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
ctattgccag                                                          10

<210> SEQ ID NO 811
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
acgtacacac                                                          10

<210> SEQ ID NO 812
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
cagcctagct                                                          10

<210> SEQ ID NO 813
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
gaaaaacaac                                                          10

<210> SEQ ID NO 814
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
cgttcagtta                                                          10

<210> SEQ ID NO 815
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
caatcagaat                                                          10

<210> SEQ ID NO 816
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
gggctactct                                                          10

<210> SEQ ID NO 817
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
ccccattggg                                                          10

<210> SEQ ID NO 818
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
tagggaacgg                                                          10

<210> SEQ ID NO 819
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
cagctgatac                                                          10

<210> SEQ ID NO 820
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
attcctgtga                                                          10

<210> SEQ ID NO 821
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
tcagagccgt                                                          10

<210> SEQ ID NO 822
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
catgaaaagc                                                          10

<210> SEQ ID NO 823
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
tgacctgtga                                                          10

<210> SEQ ID NO 824
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
gcattagcag                                                          10

<210> SEQ ID NO 825
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
gacagaacca                                                          10

<210> SEQ ID NO 826
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
tccagtatat                                                          10

<210> SEQ ID NO 827
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
tgttccgcta                                                          10

<210> SEQ ID NO 828
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
gatatccatt                                                          10

<210> SEQ ID NO 829
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
catatggacc                                                          10

<210> SEQ ID NO 830
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
gatatagtaa                                                          10

<210> SEQ ID NO 831
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
caccttttt                                                           10

<210> SEQ ID NO 832

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
agcttgcggg                                                          10

<210> SEQ ID NO 833
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
cgcacaggga                                                          10

<210> SEQ ID NO 834
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
tctgggtgct                                                          10

<210> SEQ ID NO 835
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
tgagtcgttt                                                          10

<210> SEQ ID NO 836
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
ttacaatgtg                                                          10

<210> SEQ ID NO 837
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
cttgcaaaca                                                          10

<210> SEQ ID NO 838
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
tgtcgagctg                                                          10

<210> SEQ ID NO 839
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
actttaacct                                                          10

<210> SEQ ID NO 840
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
atataagtgc                                                          10

<210> SEQ ID NO 841
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ggaagggcgt                                                          10

<210> SEQ ID NO 842
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
tttgacttga                                                          10

<210> SEQ ID NO 843
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
gtataaacgg                                                          10

<210> SEQ ID NO 844
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 844
taaccggatg                                                              10

<210> SEQ ID NO 845
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
ttctcatcag                                                              10

<210> SEQ ID NO 846
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
ctcggttacg                                                              10

<210> SEQ ID NO 847
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
atatggttct                                                              10

<210> SEQ ID NO 848
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
cgcccccgaa                                                              10

<210> SEQ ID NO 849
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
acctcgatcg                                                              10

<210> SEQ ID NO 850
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 850
ctcgaataat                                                          10

<210> SEQ ID NO 851
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
gcccgagctt                                                          10

<210> SEQ ID NO 852
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
aacagtcaac                                                          10

<210> SEQ ID NO 853
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
ctggaacctc                                                          10

<210> SEQ ID NO 854
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
aataacgggg                                                          10

<210> SEQ ID NO 855
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
acgccccact                                                          10

<210> SEQ ID NO 856
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 856
ggcaacatga                                                                10

<210> SEQ ID NO 857
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
gctatttcgc                                                                10

<210> SEQ ID NO 858
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
ttccacttta                                                                10

<210> SEQ ID NO 859
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
gccgatggat                                                                10

<210> SEQ ID NO 860
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
aagttggtaa                                                                10

<210> SEQ ID NO 861
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
cactagctag                                                                10

<210> SEQ ID NO 862
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 862
acatgccct                                                            10

<210> SEQ ID NO 863
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
ttcattactc                                                           10

<210> SEQ ID NO 864
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
ggtttaatat                                                           10

<210> SEQ ID NO 865
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
cctgcagtga                                                           10

<210> SEQ ID NO 866
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
tctttaagtt                                                           10

<210> SEQ ID NO 867
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
tggcgatcga                                                           10

<210> SEQ ID NO 868
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 868
cttttagct                                                               10

<210> SEQ ID NO 869
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
cccagtctct                                                              10

<210> SEQ ID NO 870
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
aaatgtttcg                                                              10

<210> SEQ ID NO 871
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
atataagacg                                                              10

<210> SEQ ID NO 872
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
tcactttaca                                                              10

<210> SEQ ID NO 873
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
cctggcgccc                                                              10

<210> SEQ ID NO 874
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 874
ggattactgg                                                            10

<210> SEQ ID NO 875
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
gaatgatctt                                                            10

<210> SEQ ID NO 876
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
gctcggatcg                                                            10

<210> SEQ ID NO 877
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
cagctgcgag                                                            10

<210> SEQ ID NO 878
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
acccttacta                                                            10

<210> SEQ ID NO 879
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
aggtgaaact                                                            10

<210> SEQ ID NO 880
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
```
cgaatttgat                                                             10

<210> SEQ ID NO 881
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
cgctgtgcgg                                                             10

<210> SEQ ID NO 882
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
ttaccgcacc                                                             10

<210> SEQ ID NO 883
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
ggaatcttaa                                                             10

<210> SEQ ID NO 884
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
ctcaacaccc                                                             10

<210> SEQ ID NO 885
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
cgtgcccttg                                                             10

<210> SEQ ID NO 886
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886

```
gcaggctcga                                                          10

<210> SEQ ID NO 887
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
accaacgaag                                                          10

<210> SEQ ID NO 888
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
cctgtaattt                                                          10

<210> SEQ ID NO 889
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
gggtgggatg                                                          10

<210> SEQ ID NO 890
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
ttgctcaccg                                                          10

<210> SEQ ID NO 891
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
ttacgaccac                                                          10

<210> SEQ ID NO 892
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ttttctaacc                                                          10
```

<210> SEQ ID NO 893
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
gctttagata                                                          10

<210> SEQ ID NO 894
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
cacgtattgg                                                          10

<210> SEQ ID NO 895
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
aaatatctcc                                                          10

<210> SEQ ID NO 896
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
gctggaaaac                                                          10

<210> SEQ ID NO 897
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
gagcgcatta                                                          10

<210> SEQ ID NO 898
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
gtggaggggt                                                          10

<210> SEQ ID NO 899
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 899
tccactggga                                                              10

<210> SEQ ID NO 900
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 900
caatagcgga                                                              10

<210> SEQ ID NO 901
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 901
catctagttt                                                              10

<210> SEQ ID NO 902
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 902
gaagttccgg                                                              10

<210> SEQ ID NO 903
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 903
agcgagattc                                                              10

<210> SEQ ID NO 904
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 904
ttaaggtcgg                                                              10

```
<210> SEQ ID NO 905
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
aatggttagg                                                          10

<210> SEQ ID NO 906
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
cgttattata                                                          10

<210> SEQ ID NO 907
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
acggaaagga                                                          10

<210> SEQ ID NO 908
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
ccttgtcccg                                                          10

<210> SEQ ID NO 909
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
atactttttt                                                          10

<210> SEQ ID NO 910
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
ctgggtctgg                                                          10

<210> SEQ ID NO 911
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
aaccattgcg                                                           10

<210> SEQ ID NO 912
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
agaccgggcc                                                           10

<210> SEQ ID NO 913
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
tgggacacac                                                           10

<210> SEQ ID NO 914
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914
tgcgcagttg                                                           10

<210> SEQ ID NO 915
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
cgttcgcctt                                                           10

<210> SEQ ID NO 916
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
tctcactcgt                                                           10

<210> SEQ ID NO 917
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
acaccgacgt                                                          10

<210> SEQ ID NO 918
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
ttcagcccct                                                          10

<210> SEQ ID NO 919
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
aggcgactaa                                                          10

<210> SEQ ID NO 920
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
tgctatcaag                                                          10

<210> SEQ ID NO 921
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
gtccagtagc                                                          10

<210> SEQ ID NO 922
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
cgtgtgggcg                                                          10

<210> SEQ ID NO 923
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 923
gtggttctcc                                                           10

<210> SEQ ID NO 924
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
gcagccgacg                                                           10

<210> SEQ ID NO 925
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
gctgtccacg                                                           10

<210> SEQ ID NO 926
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
cgacactcat                                                           10

<210> SEQ ID NO 927
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
catggcacct                                                           10

<210> SEQ ID NO 928
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
tgtgacgtgt                                                           10

<210> SEQ ID NO 929
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
tttggactaa                                                                10

<210> SEQ ID NO 930
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
ttcatgcccg                                                                10

<210> SEQ ID NO 931
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
ttgatcgtgg                                                                10

<210> SEQ ID NO 932
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
tagcatagga                                                                10

<210> SEQ ID NO 933
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
gtagttgcaa                                                                10

<210> SEQ ID NO 934
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
gggacagcta                                                                10

<210> SEQ ID NO 935
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 935
aaacccccaa                                                              10

<210> SEQ ID NO 936
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
actctcacaa                                                              10

<210> SEQ ID NO 937
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
atcattgcca                                                              10

<210> SEQ ID NO 938
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
ccagtttgcg                                                              10

<210> SEQ ID NO 939
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
acattagtca                                                              10

<210> SEQ ID NO 940
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
ctccagggta                                                              10

<210> SEQ ID NO 941
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 941
gaagggccaa                                                           10

<210> SEQ ID NO 942
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
cagtctcccc                                                           10

<210> SEQ ID NO 943
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
gagacattcc                                                           10

<210> SEQ ID NO 944
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
aacggtgttg                                                           10

<210> SEQ ID NO 945
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
agcattatca                                                           10

<210> SEQ ID NO 946
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
ctataccgag                                                           10

<210> SEQ ID NO 947
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 947
aactggatca                                                                10

<210> SEQ ID NO 948
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
gtcttgtcgg                                                                10

<210> SEQ ID NO 949
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
gacgagccgc                                                                10

<210> SEQ ID NO 950
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
ggaacactgt                                                                10

<210> SEQ ID NO 951
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
taaatgcgtt                                                                10

<210> SEQ ID NO 952
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
gcgaacacag                                                                10

<210> SEQ ID NO 953
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 953
ttctctcaac                                                              10

<210> SEQ ID NO 954
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
gtcgtactga                                                              10

<210> SEQ ID NO 955
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
tgtggcgtaa                                                              10

<210> SEQ ID NO 956
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
tgagcggcgt                                                              10

<210> SEQ ID NO 957
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
cctcgtgaac                                                              10

<210> SEQ ID NO 958
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
gagcaatgaa                                                              10

<210> SEQ ID NO 959
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
```
cgagacctaa                                                            10

<210> SEQ ID NO 960
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
aactgagcgc                                                            10

<210> SEQ ID NO 961
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
taaagctcgt                                                            10

<210> SEQ ID NO 962
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
ctctttacgt                                                            10

<210> SEQ ID NO 963
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
ccccgtggaa                                                            10

<210> SEQ ID NO 964
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
tcggttcgtc                                                            10

<210> SEQ ID NO 965
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 965
ctgcttacac                                                          10

<210> SEQ ID NO 966
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
acaccgtaat                                                          10

<210> SEQ ID NO 967
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
cctggtcggc                                                          10

<210> SEQ ID NO 968
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
ggttatttgg                                                          10

<210> SEQ ID NO 969
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
gcaactgagt                                                          10

<210> SEQ ID NO 970
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
ataaggcctc                                                          10

<210> SEQ ID NO 971
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
cgtgcgaagg                                                          10

<210> SEQ ID NO 972
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
gtcacacact                                                            10

<210> SEQ ID NO 973
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
catacggcaa                                                            10

<210> SEQ ID NO 974
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
gaactgccca                                                            10

<210> SEQ ID NO 975
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
aatatgtgaa                                                            10

<210> SEQ ID NO 976
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
ccgatcctgt                                                            10

<210> SEQ ID NO 977
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
caaagagcct                                                            10

<210> SEQ ID NO 978
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
taacttagag                                                          10

<210> SEQ ID NO 979
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
cagcatgtag                                                          10

<210> SEQ ID NO 980
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
ccccatgcag                                                          10

<210> SEQ ID NO 981
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 981
tctgaaccac                                                          10

<210> SEQ ID NO 982
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
gcgtgcaaaa                                                          10

<210> SEQ ID NO 983
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
gctagtaccg                                                          10

```
<210> SEQ ID NO 984
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
tttcccgcgc                                                          10

<210> SEQ ID NO 985
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
ccttagtagg                                                          10

<210> SEQ ID NO 986
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
ttgtgtcttg                                                          10

<210> SEQ ID NO 987
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
gcaacgaagc                                                          10

<210> SEQ ID NO 988
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
tgaaaccctt                                                          10

<210> SEQ ID NO 989
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
ttctacgatc                                                          10

<210> SEQ ID NO 990
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
attaaaggtg                                                           10

<210> SEQ ID NO 991
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
tatctaacgg                                                           10

<210> SEQ ID NO 992
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
agtgctcctg                                                           10

<210> SEQ ID NO 993
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
ccgtccctct                                                           10

<210> SEQ ID NO 994
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
ctaacgagcg                                                           10

<210> SEQ ID NO 995
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 995
aagtccggct                                                           10

<210> SEQ ID NO 996
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
ggcgtataag                                                              10

<210> SEQ ID NO 997
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
agatattagg                                                              10

<210> SEQ ID NO 998
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
tcctaacagc                                                              10

<210> SEQ ID NO 999
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
gaggatacgc                                                              10

<210> SEQ ID NO 1000
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
cgctctttaa                                                              10

<210> SEQ ID NO 1001
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
agacgtgtgc tcttccgatc t                                                 21

<210> SEQ ID NO 1002
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1002
agatcggaag agcgtcgtgt                                                20

<210> SEQ ID NO 1003
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(41)
<223> OTHER INFORMATION: a, c, t, g, unknown or other
<220> FEATURE:
<221> NAME/KEY: misc_feature
<222> LOCATION: (32)..(41)
<223> OTHER INFORMATION: This region represents the random sequence
      fragment

<400> SEQUENCE: 1003
agacgtgtgc tcttccgatc tgctacataa tnnnnnnnnn nagatcggaa gagcgtcgtg        60
t                                                                        61
```

RAPID DESIGN, BUILD, TEST, AND LEARN TECHNOLOGIES FOR IDENTIFYING AND USING NON-VIRAL CARRIERS

CROSS-REFERENCE TO RELATED APPLICATIONS

This application claims priority under 35 U.S.C. § 119(e) to U.S. Provisional Application Ser. No. 63/172,069 filed on Apr. 7, 2021, the entire disclosure of which is incorporated herein by reference.

FIELD OF THE DISCLOSURE

The disclosure relates to barcoded polymer nanoparticles for in vivo screening and for in vivo therapeutic delivery, and methods therefor. More particularly, the invention relates to polymer nanoparticles, such as reversible addition-fragmentation chain transfer (RAFT) polymer compositions, associated with polynucleotide barcodes, for therapeutic delivery, and for high throughput in vivo screening of drug delivery nanoparticles.

BACKGROUND

Genetic medicines (including gene therapy, gene silencing, splicing regulators, and nuclease based gene editors) are poised to produce revolutionary treatments, including vaccines, infectious disease treatments, antimicrobial treatments, antiviral treatments, and most notably, genetic disease treatments. However, the in vivo delivery of these genetic medicine payloads to the specific tissues and cells that need to be treated, while avoiding tissues and cells that can reduce the efficacy or safety of the genetic medicine, poses a significant challenge. Additional challenges include the ability to deliver large genetic payloads or multiple payloads. Adeno-associated viruses (AAVs) are the most widely used tool for genetic medicine delivery, but AAVs are not able to deliver large genetic payloads or multiple payloads (such as the clustered regularly interspaced short palindromic repeats (CRISPR)/Cas9 system), and they sometimes trigger unwanted immune responses, including the generation of anti-AAV antibodies, a cell mediated response. Some of the immune responses caused by AAV in patients are potentially fatal immune responses.

Therapeutics based on the CRISPR/Cas9 system have an exceptional potential to treat a number of genetic diseases due to the capability of this system for precise and programmable gene editing. Gene editing and repair using the CRISPR/Cas9 system has two main mechanisms, including non-homologous end joining (NHEJ) which repairs the site of cut by inducing random indel mutation, and homology-directed repair (HDR), which repairs the cut site based on a pre-existing template. Because a pre-designed template can be used for HDR-directed repair, therapies based on this mechanism can be tailored to cure a large number of different genetic diseases. However, the main challenge is that HDR repair requires the delivery of CRISPR/Cas9, small guide RNA (sgRNA) and a donor DNA strand at the same time to a particular location. This requirement becomes particularly limiting for in vivo applications because ensuring co-delivery of multiple large molecules to the same targeted location is currently not feasible. For example, the Cas9 enzyme sequence and guide RNA complex is too large to fit into AAVs.

Thus, there is a need for effective non-viral delivery systems, including gene delivery systems. The current state-of-the-art non-viral gene delivery systems, such as liposomes, have many drawbacks such as poor biocompatibility and the inability to easily engineer or functionalize them. Additional concerns are that such non-viral gene delivery systems are easily degraded by various enzymes as they pass through intracellular or intercellular compartments, and these systems have not been able to package multiple large payloads.

The inventors have designed barcoded polymer nanoparticle (e.g., a polymer derived from a controlled living/radical polymerization such as a RAFT polymer) delivery compositions. These compositions have the advantage of being biocompatible, non-toxic, and can be programmed in many ways. For example, the barcoded polymer nanoparticle delivery compositions can be programmed to have functional groups that enable them to evade early degradation, that enable them to evade immune responses, and that enable intracellular imaging and controlled delivery of therapeutic genes and other therapeutic molecules. Thus, these non-viral delivery compositions can enhance the stability, safety, and/or efficacy of genetic medicine payloads and other payloads by providing immune evasion, tissue-directed intracellular delivery, and the ability to deliver large genetic payloads or multiple payloads.

The present disclosure combines these non-viral delivery compositions with rapid design, build, test, and learn (DBTL) technologies that will vastly accelerate gene delivery and address the disadvantages that exist in limited gene delivery vehicles. In addition to hastening editing therapies of today to transition through clinicals, it is anticipated that these technologies will enable the general delivery of larger more molecularly diverse genetic payloads, and other payloads, which will in turn, continue to improve treatments for genetic diseases and other diseases.

SUMMARY

In some aspects, the disclosure provides for a composition comprising a non-viral delivery vehicle comprising one or more nanoparticle forming polymers, and a nucleic acid construct.

In some aspects, the disclosure provides for a method of in vivo screening for a desired polymer nanoparticle for use as a delivery vehicle, the method comprising (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or the tissues of the animal, (e) detecting the nucleic acid constructs in the cells or the tissues of the animal, and (f) identifying the desired polymer nanoparticle for use as a delivery vehicle.

In some aspects, the disclosure provides for a method of treating a patient with a disease, the method comprising administering to the patient the polymer nanoparticle identified in the in vivo screening methods described herein, wherein the polymer nanoparticle further comprises a drug payload, such as a polynucleotide or a protein payload or a small molecule therapeutic payload, and treating the disease in the patient.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the "EXAMPLES" are applicable to any of the following embodiments of the invention described in the numbered clauses below.

1. A composition comprising:
   a. a non-viral delivery vehicle comprising one or more nanoparticle forming polymers, and
   b. a nucleic acid construct.

2. The composition of clause 1, wherein the non-viral delivery vehicle comprises a polymer nanoparticle.

3. The composition of clause 1 or 2, wherein the nucleic acid construct is associated with the non-viral delivery vehicle via an electrostatic interaction.

4. The composition of any one of clauses 1 to 3, wherein the nucleic acid construct is associated with the non-viral delivery vehicle by an electrostatic interaction of a positively charged polymer segment of the one or more nanoparticle forming polymers and a negatively charged polynucleotide segment of the nucleic acid construct.

5. The composition of any one of clauses 1 to 3, wherein the nucleic acid construct is associated with the non-viral delivery vehicle by a high affinity, non-covalent bond interaction between a biotin molecule on the 5' and/or the 3' end of the nucleic acid construct and a molecule that binds to biotin on the one or more nanoparticle forming polymers.

6. The composition of any one of clauses 1 to 3, wherein the nucleic acid construct is associated with the non-viral delivery vehicle by a covalent bond between a carboxy terminated polymer segment and the nucleic acid construct, wherein the nucleic acid construct comprises a primary amine on the 5' and/or the 3' end.

7. The composition of any one of the preceding clauses, wherein the nucleic acid construct comprises:
   a. two primer binding segments; and
   b. one or more unique polynucleotide barcodes between the two primer binding segments.

8. The composition of clause 7, wherein the primer binding segments range in length from about 15 base pairs to about 30 base pairs.

9. The composition of clause 7 or 8, wherein the primer binding segments are a universal primer binding set.

10. The composition of any one of clauses 7 to 9, wherein the one or more polynucleotide barcodes comprise unique sequences of 6-20 nucleotides in length.

11. The composition of clause 10, wherein the polynucleotide barcodes further comprise a hamming distance of at least 2-6 bases between any two unique polynucleotide barcode sequences.

12. The composition of any one of the preceding clauses, wherein the nucleic acid construct further comprises from about 6 to about 12 random bases at the 3' end of the polynucleotide barcode.

13. The composition of clause 12, wherein the about 6 to about 12 random bases at the 3' end of the polynucleotide barcode are for bioinformatic removal of PCR duplicates.

14. The composition of any one of the preceding clauses, wherein the nucleic acid construct ranges in length from about 42 nucleotides to about 210 nucleotides.

15. The composition of any one of the preceding clauses, wherein the one or more nanoparticle forming polymers comprise monomer units compatible with a controlled living/radical polymerization.

16. The composition of any one of the preceding clauses, wherein the one or more nanoparticle forming polymers are prepared by reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, or ring-opening polymerization.

17. The composition of any one of the preceding clauses, wherein the one or more nanoparticle forming polymers are prepared from monomers containing a vinyl group.

18. The composition of any one of the preceding clauses, wherein the one or more nanoparticle forming polymers are prepared using a chain transfer agent such as those used in reversible addition-fragmentation chain transfer (RAFT).

19. The composition of any one of the preceding clauses, wherein the one or more nanoparticle forming polymers are RAFT block copolymers comprising
   a. a first terminus comprising a first capping unit derived from a first chain transfer agent in a RAFT copolymerization process;
   b. a first block prepared from one or more monomer units covalently attached to the first reactive functional unit, and having a molecular weight ($M_n$) in the range of about 1 kDa to about 500 kDa and a degree of polymerization in the range of about 10 to about 2500;
   c. optionally a second block prepared from one or more monomer units covalently attached to the first block, and having a molecular weight ($M_n$) in the range of about 1 kDa to about 500 kDa and a degree of polymerization in the range of about 20 to about 2000; and
   d. a second terminus comprising a second capping unit derived from a first or a second chain transfer agent.

20. The composition of clause 19, wherein the non-viral delivery vehicle has one or more of an overall molecular weight ($M_n$) in the range of about 25 kDa to about 60 kDa, an overall degree of polymerization in the range of about 700 to about 900, a target size in the range of about of about 10 to about 60 nm, and a maximum corona-to-core ratio (CCR) of about 1.5 to about 3.5.

21. The composition of clause 19 or 20, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

22. The composition of clause 19 or 20, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

23. The composition of any one of clauses 19 to 22, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

24. The composition of any one of clauses 19 to 23, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate. and methyl methacrylate.

25. The composition of any one of clauses 19 to 23, wherein the second block is a random copolymer prepared from three different monomer units independently selected from the group consisting of 2-dimethylaminoethyl acrylate, 2-(diethylamino) ethyl methacrylate, 2-(diisopropylamino)

ethyl methacrylate, butyl methacrylate, ethyl acrylic acid, propyl acrylic acid, (hydroxyethyl)methacrylate, and methyl methacrylate.

26. The composition of any one of clauses 19 to 25, wherein the second block is a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

27. The composition of any one of clauses 19 to 26, wherein each chain transfer agent is independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylventanoic acid, 4-cyano-4-((phenylcarbonothioyl)thio)pentanoic acid, and 4-cyano-4-[(dodecylsulfanylthiocarbonyl)sulfanyl] pentanoic acid.

28. The composition of any one of clauses 19 to 27, wherein the first capping unit is of the formula

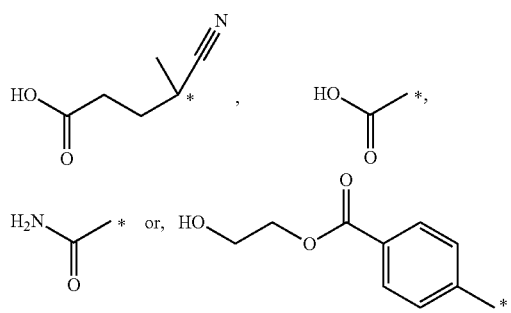

wherein * represents a point of covalent attachment to the first block.

29. The composition of any one of clauses 19 to 28, wherein the second capping unit is of the formula

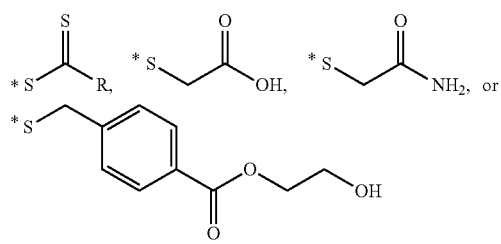

wherein * represents a point of covalent attachment to the second block, and R is —SC$_2$-C$_{12}$ alkyl or C$_6$H$_5$.

30. A method of in vivo screening for a desired polymer nanoparticle for use as a delivery vehicle, the method comprising (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or the tissues of the animal, (e) detecting the nucleic acid constructs in the cells or the tissues of the animal, and (f) identifying the desired polymer nanoparticle for use as a delivery vehicle.

31. The method of clause 30 wherein the polymer nanoparticle associated with the nucleic acid construct is according to any one of clauses 1 to 29.

32. The method of clause 30 or 31 wherein the nucleic acid construct is detected by a method selected from the group consisting of the polymerase chain reaction (PCR), isothermal amplification, sequencing, or a combination thereof, to obtain nucleotide sequence data.

33. The method of any one of clauses 30 to 32, wherein the polymer nanoparticle is loaded with a payload.

34. The method of clause 33, wherein the payload is a luminescent molecule.

35. The method of clause 34, wherein the luminescence is used to track the biodistribution or cell uptake via imaging.

36. The method of any one of clauses 30 to 35, wherein the administration to the animal is via an intramuscular, an intravenous, an intraperitoneal, an oral, or a pulmonary route.

37. The method of any one of clauses 30 to 36, wherein the nucleic acid construct is isolated from the cells and the tissues by mixing with a first organic compound and incubating the organic phase with an aqueous phase of the cell or tissue sample, separating the organic phase from the aqueous phase, mixing the organic phase with a second organic compound, incubating the mixture, precipitating the nucleic acid construct from the mixture, removing the organic phase by evaporation, and resuspending the nucleic acid construct in an aqueous composition.

38. The method of clause 37, wherein the organic phase comprises phenol chloroform.

39. The method of clause 37, wherein the nucleic acid construct is separated from cationic material in the cells or tissues by titrating the aqueous composition of the nucleic acid construct to a pH of greater than 7.4.

40. The method of clause 30, wherein the nucleic acid construct is separated from material in the cells or tissues by binding the nucleic acid construct with a molecule with a binding affinity to the nucleic acid construct greater than the binding affinity to the cell or tissue material.

41. The method of clause 30, wherein the nucleic acid construct is separated from material in the cells or tissues via size exclusion chromatography.

42. The method of clause 30, wherein the nucleic acid construct is separated from material in the cells or tissues via dialysis or diafiltration.

43. The method of clause 30, wherein the nucleic acid construct is separated from material in the cells or tissues via filtration.

44. The method of clause 30, wherein the nucleic acid construct is separated from material in the cells or tissues by digesting proteins using an enzyme.

45. The method of clause 44 wherein the enzyme is Proteinase K.

46. The method of clause 30, wherein the nucleic acid constructs associated with the polymer nanoparticles are detected by first diluting the isolated nucleic acid constructs by a factor of at least 1000 times, and then amplifying the nucleic acid constructs by PCR using primers.

47. The method of clause 46, wherein the primers from the PCR step are enzymatically digested prior to detection of amplicons.

48. The method of clause 32, wherein the nucleotide sequence data is converted to fast Q files; and the fast Q files are mapped to known polynucleotide barcodes and the polynucleotide barcodes are enumerated.

49. A method of treating a patient with a disease, the method comprising administering to the patient the polymer nanoparticle identified in the in vivo screening method of any one of clauses 30 to 48, wherein the polymer nanoparticle further comprises a payload, and treating the disease in the patient.

BRIEF DESCRIPTION OF THE DRAWINGS

FIG. 4 is an illustration of one representative example of a nucleic acid construct of the present disclosure, showing the length (in base pairs (bp)) of the primer binding segments (20 bp and 21 bp in the construct shown), the polynucleotide barcode (8 bp in the construct shown), and the random sequence fragment (7 bp in the construct shown) of the present disclosure.

FIGS. 5(a)-5(c) are a schematic drawing of nucleic acid construct labeling reaction methods using electrostatic loading reaction (FIG. 5(a)), avidin-streptavidin conjugation (FIG. 5(b)), and direct amidification (FIG. 5(c)).

In FIG. 11(a), the area under the curve denoted by the bar in the graph accounts for 84.17% of the cells.

DETAILED DESCRIPTION OF ILLUSTRATIVE EMBODIMENTS

Figure 1:
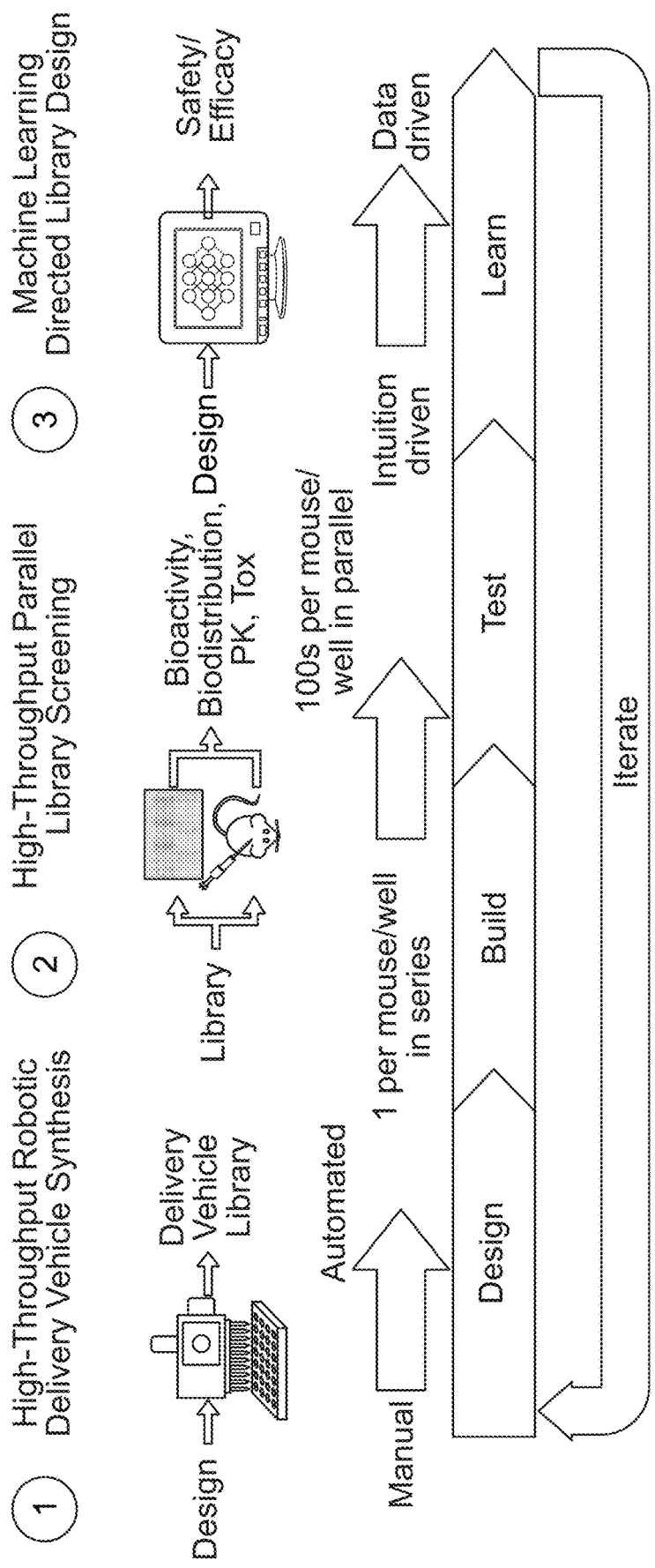
FIG. 1 is a schematic diagram showing a simplified flow diagram illustrating a DBTL cycle for non-viral gene delivery development based on automated synthesis, high throughput testing, and machine learning design.

The invention relates to barcoded polymer nanoparticles for in vivo screening and for in vivo therapeutic delivery, and methods therefor. More particularly, the invention relates to polymer nanoparticles, such as a controlled living/radical polymerization products, such as reversible addition-fragmentation chain transfer (RAFT) polymer compositions, associated with polynucleotide barcodes, for therapeutic delivery, and for high throughput in vivo screening of drug delivery nanoparticles. In one embodiment, the payload can be a nucleic acid of 3 kB or more, or any other suitable payload, such as another polynucleotide or a protein or a small molecule therapeutic or a luminescent molecule.

The invention relates to the use of barcoded polymer nanoparticle compositions (e.g., a polymer nanoparticle derived from a controlled living/radical polymerization process, such as RAFT copolymers) as a platform with a high degree of tunability in structure and function, opportunities to protect payloads from adverse reactions or degradation by the immune system, and passive cell targeting via surface charge, or particle size. These delivery systems also lend themselves to computer-aided design, and they have suitable pathways to robust, commercial scale manufacturing processes with higher yields and fewer purification steps than viral delivery composition manufacturing processes.

In one embodiment a composition comprising a polymer nanoparticle (e.g., a polymer nanoparticle derived from a controlled living/radical polymerization process, such as RAFT polymer) associated with a nucleic acid construct is provided. In another embodiment, a method of in vivo screening to identity a desired polymer nanoparticle (e.g., a polymer nanoparticle derived from a controlled living/radical polymerization process, such as RAFT polymer) associated with a nucleic acid construct for use as a delivery vehicle is provided. In another embodiment, a method of treating a patient with a disease is provided comprising administering to the patient the polymer nanoparticle identified in the screening method.

In one embodiment, the method of in vivo screening for a desired polymer nanoparticle for use as a delivery vehicle comprises, (a) preparing a library comprising two or more types of polymer nanoparticles, wherein each polymer nanoparticle is associated with a nucleic acid construct comprising a different polynucleotide barcode, (b) administering the library to an animal, (c) removing cells or tissues from the animal, (d) isolating the nucleic acid constructs from the cells or tissues of the animal, (e) detecting the nucleic acid constructs in the cells or tissue of the animal, and (f) identifying the desired polymer nanoparticle for use as a delivery vehicle. In various embodiments, the nucleic acid construct can be detected by, for example, the polymerase chain reaction (PCR), isothermal amplification, or sequencing the nucleic acids in the cells or tissues of the animal.

In another embodiment, a method of treating a patient with a disease is provided, comprising administering to the patient the polymer nanoparticle identified in the in vivo screening method, wherein the polymer nanoparticle further comprises a drug payload, such as a polynucleotide or a protein payload, or a small molecule therapeutic or luminescent molecule payload, and treating the disease in the patient.

In various embodiments, any suitable route for administration of the library of polymer nanoparticles associated with nucleic acid constructs for the method of in vivo screening for the polymer nanoparticle associated with a nucleic acid construct, or for the method of treatment can be used including parenteral administration. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques. In other embodiments, oral or pulmonary routes of administration can be used.

In one aspect, libraries of barcoded polymer nanoparticles can be pooled and concentrated before administration to the animal of the nucleic acid constructs associated with the polymer nanoparticles. Methods for library preparation and for sequencing are described in Green and Sambrook, "Molecular Cloning: A Laboratory Manual", 4th Edition, Cold Spring Harbor Laboratory Press, (2012), incorporated herein by reference.

In various embodiments, cell or tissue samples may be analyzed for the presence of the polymer nanoparticle associated with the nucleic acid constructs described herein. The samples can be any tissue, cell, or fluid sample from an animal, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, or any tissue or cell sample from an animal. Exemplary tissue or cell samples include brain tissue or cells, muscle tissue or cells, skin tissue or cells, heart tissue or cells, kidney tissue or cells, stomach tissue or cells, liver tissue or cells, urinary tract tissue or cells, gastrointestinal tract tissue or cells, head or neck tissue or cells, lung tissue or cells, reproductive tract tissue or cells, pancreatic tissue or cells, or any other tissue or cell type from an animal.

In one illustrative aspect for removing cells or tissues from the animal and isolating the nucleic acid constructs from the cells or tissues of the animal, the nucleic acid constructs are removed from cells or tissues of the animal. In various embodiments, nucleic acid constructs (e.g., DNA or RNA) obtained from the tissues or cells of the animal can be removed by rupturing the cells and isolating the nucleic acid constructs from the lysate. Techniques for rupturing cells and for isolation of nucleic acids are well-known in the art, and removal techniques include homogenization, such as by using a bead-beating technique. In other embodiments, the nucleic acid constructs may be isolated by rupturing cells using a detergent or a solvent, such as phenol-chloroform. In another aspect, the nucleic acid constructs may be separated from the lysate by physical methods including, but not limited to, centrifugation, dialysis, diafiltration, filtration, size exclusion, pressure techniques, digestion of proteins with Proteinase K, or by using a substance with an affinity for nucleic acids such as, for example, beads that bind nucleic acids.

In one illustrative embodiment, the nucleic acid constructs are removed from cells or tissues by treating with a mixture of an organic phase (e.g., phenol chloroform) and an aqueous phase (e.g., water). The organic phase (e.g., phenol chloroform) is isolated and the nucleic acid construct can be precipitated by raising the pH, for example, to pH 7.4. The organic phase (e.g., phenol chloroform) can be evaporated and the nucleic acid constructs can be suspended in water and diluted to appropriate concentrations for PCR and/or sequencing. In one embodiment, the isolated nucleic acid constructs are suspended in either water or a buffer after sufficient washing.

In other embodiments, commercial kits are available for isolation of the nucleic acid constructs, such as Qiagen™, Nuclisensm™, Wizard™ (Promega), QiaAmp 96 DNA Extraction Kit™ and a Qiacube HT™ instrument, and Promegam™. Methods for preparing nucleic acids for PCR and/or sequencing are also described in Green and Sambrook, "Molecular Cloning: A Laboratory Manual", 4th Edition, Cold Spring Harbor Laboratory Press, (2012), incorporated herein by reference.

The polynucleotide barcodes can be detected by using, for example, the polymerase chain reaction (PCR), isothermic amplification, sequencing, and/or imaging. The polymerase chain reaction (PCR) has been developed to analyze nucleic acids in a laboratory. PCR evolved over the last decade into a new generation of devices and methods known as Next Generation Sequencing (NGS). NGS provides faster detection and amplification of nucleic acids at a cheaper price. The NGS devices and methods allow for rapid sequencing as the nucleic acids are amplified in massively parallel, high-throughput platforms.

In one illustrative aspect, the nucleic acid constructs can be sequenced, to detect the polynucleotide barcodes using any suitable sequencing method including Next Generation Sequencing (e.g., using Illumina, ThermoFisher, or PacBio or Oxford Nanopore Technologies sequencing platforms), sequencing by synthesis, pyrosequencing, nanopore sequencing, or modifications or combinations thereof can be used. In one embodiment, the sequencing can be amplicon sequencing. In another embodiment, the sequencing can be whole genome sequencing. In another embodiment, the sequencing can be exome/targeted hybridization sequencing. Methods for sequencing nucleic acids are also well-known in the art and are described in Sambrook et al., "Molecular Cloning: A Laboratory Manual", Cold Spring Harbor Laboratory Press, incorporated herein by reference.

In one aspect, the nucleic acid construct can comprise a polynucleotide barcode and the barcode comprises a unique sequence not present in any known genome for identification of the polynucleotide barcode. In another embodiment, a set of different nucleic acid constructs with different polynucleotide barcodes (e.g., 88 or 96 different polynucleotide barcodes) can be used to allow for multiplexing of samples on one sequencing run.

In various embodiments, the polynucleotide barcodes can be from about 5 to about 35 base pairs in length, about 5 to about 34 base pairs in length, about 5 to about 33 base pairs in length, about 5 to about 32 base pairs in length, about 5 to about 31 base pairs in length, about 5 to about 30 base pairs in length, about 5 to about 29 base pairs in length, about 5 to about 28 base pairs in length, about 5 to about 27 base pairs in length, about 5 to about 26 base pairs in length, about 5 to about 25 base pairs in length, about 5 to about 24 base pairs in length, about 5 to about 23 base pairs in length, about 5 to about 22 base pairs in length, about 5 to about 21 base pairs in length, about 5 to about 20 base pairs in length, about 5 to about 19 base pairs in length, about 5 to about 18 base pairs in length, about 5 to about 17 base pairs in length, about 5 to about 16 base pairs in length, about 5 to about 15 base pairs in length, about 5 to 14 base pairs in length, about 5 to 13 base pairs in length, about 5 to 12 base pairs in length, about 5 to 11 base pairs in length, about 5 to 10 base pairs in length, about 5 to 9 base pairs in length, about 5 to 8 base pairs in length, about 6 to 10 base pairs in length, about 7 to 10 base pairs in length, about 8 to 10 base pairs in length, or about 6 to about 20 base pairs in length.

Various embodiments of polynucleotide barcodes are shown below in Table 1 (labeled "Polynucleotide Barcodes"). These polynucleotide barcodes can be used in the nucleic acid constructs alone or in combinations of, for example, two or more polynucleotide barcodes, three or more polynucleotide barcodes, four or more polynucleotide barcodes, etc. In the embodiment where more than one polynucleotide barcode is used, the hamming distance between the polynucleotide barcodes can be about 2 to about 6 nucleotides, or any suitable number of nucleotides can form a hamming distance, or no nucleotides are present between the polynucleotide barcodes.

TABLE 1

| Polynucleotide Barcodes | SEQ ID NO: | Polynucleotide Barcodes | SEQ ID NO: | Polynucleotide Barcodes | SEQ ID NO: |
| --- | --- | --- | --- | --- | --- |
| GCTACATAAT | 1 | AGCAGTCCCG | 342 | CAAAATAGCG | 683 |
| ATGTTACACA | 2 | TTTGGGCTGT | 343 | GAAGAAGAAG | 684 |
| TGGGGCCCAA | 3 | CTCACGATCT | 344 | CACCCGCACG | 685 |
| TAGTTTATCC | 4 | TGGCGCATAC | 345 | ACGATGCCCG | 686 |
| ACCCCGTCTT | 5 | GCAATTGAAA | 346 | CCTACTACAC | 687 |
| CCGGCCATCA | 6 | TCGGGAGACG | 347 | ATTGAAACAA | 688 |
| GAGCTTGCTC | 7 | CCCGGCGAAA | 348 | GACCGAAGAT | 689 |
| ACGTTCTATA | 8 | TGATGCGGAA | 349 | ACGGCCTGAA | 690 |
| TACAGCAAAA | 9 | AACTGAGGCG | 350 | AGGGGAGGTC | 691 |
| GTTAGGTGGT | 10 | CATATTATTT | 351 | CAATCAACTT | 692 |
| GGAGACCGAC | 11 | AAAAGTCATT | 352 | GGACAACCGA | 693 |
| TGGCCCCTTG | 12 | AAGCGGTGAG | 353 | TCCCTAAGGC | 694 |
| TGGCCGTAAG | 13 | AAGGTAATCA | 354 | GTTCTACACG | 695 |
| CGTTCGTCAA | 14 | CTGACACTTA | 355 | ACTAACCAGT | 696 |
| CGGACGTGGA | 15 | CTGTTTTCTA | 356 | GAAGCTGGAT | 697 |
| AGAGGGGGCA | 16 | CACATGGCAG | 357 | GGAACCATGG | 698 |

TABLE 1-continued

| Polynucleotide Barcodes | SEQ ID NO: | Polynucleotide Barcodes | SEQ ID NO: | Polynucleotide Barcodes | SEQ ID NO: |
| --- | --- | --- | --- | --- | --- |
| GTTCAGGTCG | 17 | TTCAATCCGG | 358 | CTCTACCTGG | 699 |
| CTCGCAAGAG | 18 | TGTCCGGCAT | 359 | TAATGCCTGC | 700 |
| GCAACGACTT | 19 | TGGTACCGTG | 360 | TAAAGGCAAT | 701 |
| GCCATCCATC | 20 | AAGAGATATT | 361 | CGCCTGGGAA | 702 |
| TTCCGAGCAG | 21 | GATGTACTAC | 362 | TCTTGGGGAA | 703 |
| CTTCTGGACA | 22 | GAAATGGAAT | 363 | AGAGAGAGAG | 704 |
| AACATTAGAC | 23 | TTAAAATACT | 364 | GCGTTGGCGC | 705 |
| AAGCAATAGT | 24 | TGACCGGAAC | 365 | TTACGACAGA | 706 |
| AGGGTAAGAC | 25 | GTCGCCGCAA | 366 | GGAACTCTTA | 707 |
| CGTTGTCTTG | 26 | TAGGATACCG | 367 | GATTGTGGAG | 708 |
| TTTCCCCGCC | 27 | AGTCCAATTG | 368 | GGGCACTGAT | 709 |
| CGAATGGATC | 28 | GGGGGCTATA | 369 | AGACGCACCA | 710 |
| CATCACTTGC | 29 | ACCTTCAGTT | 370 | CCAATTATAA | 711 |
| CTCTCGCACT | 30 | ATGGCAAGTA | 371 | TAGAGACGCA | 712 |
| GTTCACGTGC | 31 | AGAATGTTTT | 372 | CCTCTTGTCG | 713 |
| AATAAGCCTG | 32 | AGTTCGTTTG | 373 | GAGGAAGCTC | 714 |
| GTTAACAATT | 33 | CACTACTGAC | 374 | AGTCCCGAGT | 715 |
| ATTCAGATCC | 34 | GATCAAGAGC | 375 | TGCTTGCAGT | 716 |
| CCTGCTGATT | 35 | ATTTATCGAG | 376 | CCCACTTCCC | 717 |
| CTTGGTCATA | 36 | CCTTTTTCCA | 377 | CGTTGCCGCG | 718 |
| TCTTCCTGTT | 37 | GCACAGAGGT | 378 | CCCCTGGTTC | 719 |
| ACTGCCATGG | 38 | TGATCTGAAT | 379 | ACGACCAATA | 720 |
| CATGTATAGT | 39 | GTTGGAGGGA | 380 | CTTAGGGTTC | 721 |
| GGTAGCGGCA | 40 | TTTTGAAGGT | 381 | AAACATATCA | 722 |
| TCACTCTAAC | 41 | TAAGTCCTAA | 382 | GGGTCGTAGA | 723 |
| AAGGTGCACC | 42 | GGTGTTAGGG | 383 | CTCCGTAGCG | 724 |
| AATGCTCGTT | 43 | TGTATGCACC | 384 | CTGGTCATAA | 725 |
| TGTCTAGAAA | 44 | CCGTGCCATT | 385 | TTGACAGATC | 726 |
| CTGCCTGCCT | 45 | GAAATCACCC | 386 | GAGTAAAGTC | 727 |
| ACTATAAAAG | 46 | TTTGCACGTG | 387 | ATATGGGCTT | 728 |
| TAGTATCGAG | 47 | CGTCTGTTTT | 388 | TACAACTACT | 729 |
| ATCGCAGTCC | 48 | CTACACCACA | 389 | AATTCAGCCG | 730 |
| TCATCAGAAC | 49 | TGCTACAGGG | 390 | GATTGTACTA | 731 |
| TCCTAGACGC | 50 | GGGAATATAT | 391 | TCGTAATGCG | 732 |
| GCCGGGCGGG | 51 | TCATGTATTT | 392 | CGATAACTGC | 733 |
| GCCCAGAAGA | 52 | TCTCCGTTTA | 393 | AACTTGGCGG | 734 |
| CTTAGAGCTG | 53 | TACCTCTCGC | 394 | CGTGGATGTA | 735 |
| GTCTGCGCTT | 54 | GCTTCAACCG | 395 | CCTTCCCGAA | 736 |

TABLE 1-continued

| Polynucleotide Barcodes | SEQ ID NO: | Polynucleotide Barcodes | SEQ ID NO: | Polynucleotide Barcodes | SEQ ID NO: |
|---|---|---|---|---|---|
| CGCCGTCCTT | 55 | ATGAAGCTAC | 396 | CTAAACCCGT | 737 |
| TTTATCTGCT | 56 | CGGTACAACT | 397 | CAACATTCCC | 738 |
| TGCTTCGGAG | 57 | GTGTGGTCGT | 398 | CTTACCCTCT | 739 |
| GGGGAGAATG | 58 | GGGGTCATGT | 399 | GGAAAGTTCT | 740 |
| GTGGTAAGTG | 59 | AGGCAGCCCA | 400 | CGGATTGGCT | 741 |
| GAAATTAGTA | 60 | CAAGCACGAT | 401 | AATGTAGGGC | 742 |
| GCTATCCTAA | 61 | TCAAATGGAT | 402 | AATGAATCGC | 743 |
| ATCTGTACGA | 62 | GGACTGAATA | 403 | ATCATACACC | 744 |
| AGTTCGGGGC | 63 | CCGTAGACGT | 404 | AGTTGGGCAG | 745 |
| CGAGTCTGTC | 64 | CGGCGTACCG | 405 | AGAAGAAGGG | 746 |
| ATCCTACGCA | 65 | GGCGGCGCCC | 406 | GCGTGCGCTA | 747 |
| ATGGTGGATA | 66 | AGACTTGATC | 407 | CCCCGATAAA | 748 |
| CCTCTAACTA | 67 | ACCTTGCACA | 408 | TACCAAGTGC | 749 |
| ATAGCTGCAC | 68 | TAAGGTGAGT | 409 | TGTGTTTTCG | 750 |
| GACAGAATTT | 69 | TTGTTGTTTC | 410 | CCCAGATGTC | 751 |
| CAATTGGCAT | 70 | GAGGGAATAC | 411 | GCGAGCTTCC | 752 |
| TCTAGTAGAC | 71 | CTCGTACGCG | 412 | GTGTCACGTA | 753 |
| TTATTCATGG | 72 | CCGCGGTTTA | 413 | ATAGGCCGAG | 754 |
| TTGGCAACCG | 73 | TTAAAGTTAA | 414 | GAGCTACCAG | 755 |
| CATAATACAT | 74 | GCATATGGGT | 415 | CGCGGCGGAG | 756 |
| ACAGACTCAC | 75 | AGTCTGAGCC | 416 | TCTTGCACGA | 757 |
| GCGATGCTGC | 76 | TGTCGGTTCG | 417 | TGCCCTAAAG | 758 |
| CATCTTTGCC | 77 | GGTCTCAACC | 418 | TTGCGCTTTG | 759 |
| GTGACTCCAG | 78 | GTAACGGCAT | 419 | CATATAAAGG | 760 |
| GGACGAGTCT | 79 | ACACTGAGAA | 420 | AATAGCGAAT | 761 |
| TAGTGGCGTG | 80 | CCCAACGTCG | 421 | TACGCTAAGG | 762 |
| AACGCAGCTT | 81 | AAGAAACTGC | 422 | ACTTAGTTCG | 763 |
| AGAACAGGTG | 82 | ACCAGCCCAC | 423 | CGTGCGGAAC | 764 |
| AGGCTATGTT | 83 | TGTAGTTACT | 424 | ACCCGATTCG | 765 |
| CCTGGATCTT | 84 | GGCTAGAGGC | 425 | TGCAGAGTTT | 766 |
| CTAGCCGGCC | 85 | GTTCGGCAGA | 426 | GAATCATTAG | 767 |
| ACCAGTTATC | 86 | CCAAAATAGA | 427 | AGTACACTGG | 768 |
| ACGTTATAGC | 87 | CCCATATAAC | 428 | TTGTGCGGTT | 769 |
| TCGAGTTTGA | 88 | GTCACTACCG | 429 | ATGACATGCA | 770 |
| TGAAGCGAGC | 89 | GTAGTGTGGC | 430 | TTCTCGGACG | 771 |
| GACTGGCGAA | 90 | CAATCTCATA | 431 | AGATTGAAGA | 772 |
| GATGGACCTA | 91 | CCATGTTATA | 432 | GGCGGACTGT | 773 |
| GTCCACAACG | 92 | TAAGCAGTGG | 433 | TTTATGGTAA | 774 |
| CCTCCCCAGA | 93 | TCGGCGGCTA | 434 | CAGTAGGGTG | 775 |
| TTATGACGCC | 94 | TATTAAATGC | 435 | GACAGGCAAG | 776 |
| CTTGATCCGT | 95 | GTCGCCATTA | 436 | GATGTGTCGT | 777 |
| AATGCGCAAT | 96 | GGCGTCGTTC | 437 | ACTTGACGGA | 778 |
| GTACCCCTCA | 97 | CTAGTAGATA | 438 | AAGTCCGAAA | 779 |
| CGACAGCTCG | 98 | TCGTCAGTAT | 439 | TGGGTGTAGG | 780 |
| TGACCTGGCT | 99 | GGGGTATCGG | 440 | ACTTACCGCG | 781 |
| TTCATAGCCC | 100 | TGCTCTGCCA | 441 | CTGTGCACCC | 782 |
| CCCAAGAGAA | 101 | TGCCGTAACT | 442 | ATTGCTCTCT | 783 |
| AAACGAAGTA | 102 | CGGTACAGGC | 443 | CAGAAGACAA | 784 |
| GACGTTTACA | 103 | TCCTAATTTG | 444 | TTACGCTATA | 785 |
| GATCGATTTG | 104 | TCTTTCTGGA | 445 | ACGTGGAAAT | 786 |
| CACTGTCACC | 105 | CCGCGACTTG | 446 | TGAGGCTGGT | 787 |
| TGTGAGAGTT | 106 | ACCTATAGCG | 447 | ATTATGAGAT | 788 |
| GACGTAACCT | 107 | GCCGGCACCT | 448 | GACTTGTAGT | 789 |
| CAGACTCTGC | 108 | TTTGATAGGC | 449 | TCGCTGAGGA | 790 |
| TATGCCAATA | 109 | ACTGTGAGCT | 450 | CCCAACTCTA | 791 |
| ACAGGTGATG | 110 | TTATCGTTCA | 451 | GATAGGGAGG | 792 |
| GTCATCGCGT | 111 | ACTAGTGGCC | 452 | TAGAAATCAG | 793 |
| TCTTATAAAC | 112 | CCTCCGTGGT | 453 | GTCGCTAGAA | 794 |
| GTGTAGACTG | 113 | TTAGGGTATG | 454 | AAAATAGAAA | 795 |
| AAACAACCGG | 114 | GAATCAGGCG | 455 | GCTCCTGGGT | 796 |
| ATCCTGTACC | 115 | GGCTGACCAA | 456 | CGCGCTCGCG | 797 |
| TTATAAGAAT | 116 | TGCCAGACCG | 457 | GGCAAACGCA | 798 |
| ATAAGTAGGC | 117 | TCCCTACGCG | 458 | TTTACTACCT | 799 |
| TCTCGTAAGG | 118 | TCCGCTGGAG | 459 | ATCCTAAACT | 800 |
| GATCCGCCGC | 119 | GGATCAAAAC | 460 | CTCCGTATGT | 801 |
| TGTCAGGTTT | 120 | TTCACCTCAC | 461 | TATCGTCCAG | 802 |
| TCCGAAGCCC | 121 | GACACACGGC | 462 | GCCGGCGGTA | 803 |
| TCCATGTCCA | 122 | TGGGCGATTA | 463 | TGCTCCATTT | 804 |
| GTGATGGTAC | 123 | TAAGATCTTC | 464 | TGGCTGTTGT | 805 |
| CTCCACATAC | 124 | CTCCGACTAC | 465 | TACTGCGCAA | 806 |
| TTCGGATGAG | 125 | GGGCCATCAT | 466 | TATACGGCTT | 807 |
| ACGACATCGC | 126 | TCAGGCCAGA | 467 | GGTTATTACC | 808 |
| GAGATGCACA | 127 | CTTGTGGGC | 468 | ATCAGGAGGA | 809 |
| TTTGTATGGC | 128 | AGATAGTCTG | 469 | CTATTGCCAG | 810 |
| CTTTTCTAGA | 129 | GCGTCAAAGT | 470 | ACGTACACAC | 811 |
| AGTCTAATCA | 130 | ACGAAAATTT | 471 | CAGCCTAGCT | 812 |

TABLE 1-continued

| Polynucleotide Barcodes | SEQ ID NO: | Polynucleotide Barcodes | SEQ ID NO: | Polynucleotide Barcodes | SEQ ID NO: |
|---|---|---|---|---|---|
| GACTTAGCCA | 131 | GAGTCTGGTG | 472 | GAAAAACAAC | 813 |
| TATCACAGTA | 132 | ATCGAGCGAC | 473 | CGTTCAGTTA | 814 |
| AAGCTCGAGT | 133 | GGTCCTCAGA | 474 | CAATCAGAAT | 815 |
| TGTTACGACA | 134 | TGATTTTGTC | 475 | GGGCTACTCT | 816 |
| AAGGATAGTC | 135 | GCATTTCTCA | 476 | CCCCATTGGG | 817 |
| GCACTTAGCC | 136 | GCATGCCAGT | 477 | TAGGGAACGG | 818 |
| GAGGGATCCG | 137 | ATTAGACGAC | 478 | CAGCTGATAC | 819 |
| ATTCTAGAAG | 138 | AAAGCCCATA | 479 | ATTCCTGTGA | 820 |
| GATAACTGAT | 139 | CACTACATTC | 480 | TCAGAGCCGT | 821 |
| ATCTGACTGT | 140 | CACGGTTCT | 481 | CATGAAAAGC | 822 |
| CAAAGCGAAC | 141 | CCCACCAGTG | 482 | TGACCTGTGA | 823 |
| GAAATTGCGA | 142 | CTCACTTGTC | 483 | GCATTAGCAG | 824 |
| GGGTCCAGTC | 143 | GATAGACTCT | 484 | GACAGAACCA | 825 |
| ATCAGGTAGC | 144 | ATTTCCATTT | 485 | TCCAGTATAT | 826 |
| GAAAGGTCCT | 145 | ATATGTGGCC | 486 | TGTTCCGCTA | 827 |
| GGCTACCACA | 146 | CGGGACGAAC | 487 | GATATCCATT | 828 |
| TTATTGCTGA | 147 | AGAACCGTGA | 488 | CATATGGACC | 829 |
| CGCCGCGTTT | 148 | TAGTGTACTG | 489 | GATATAGTAA | 830 |
| TTTTCAAAAG | 149 | AACTAATCGA | 490 | CACCTTTTTT | 831 |
| CTGGGCTAAA | 150 | CGAAGTGACG | 491 | AGCTTGCGGG | 832 |
| CCCGATGAGA | 151 | CGGAGCCTCG | 492 | CGCACAGGGA | 833 |
| TGGGAAATAT | 152 | ATCACACGAG | 493 | TCTGGGTGCT | 834 |
| GTACGAGCGG | 153 | CGACGAGTTC | 494 | TGAGTCGTTT | 835 |
| GCGTGCAGCT | 154 | GCTTCCCGTG | 495 | TTACAATGTG | 836 |
| AGTCTGCGGA | 155 | GATTCATACC | 496 | CTTGCAAACA | 837 |
| TAACTATTTA | 156 | GAGAGAAGCG | 497 | TGTCGAGCTG | 838 |
| GAGTTGCCGG | 157 | GAAGTGGCCT | 498 | ACTTTAACCT | 839 |
| CAGCCCGGCG | 158 | GGACGACGCC | 499 | ATATAAGTGC | 840 |
| TCACCTACAT | 159 | TAGGGTCTCA | 500 | GGAAGGGCGT | 841 |
| AGTGGCTAAC | 160 | AACTACAGGT | 501 | TTTGACTTGA | 842 |
| AGAATGTGAG | 161 | GTGGCCTGTG | 502 | GTATAAACGG | 843 |
| TAGTTTCGCA | 162 | CTTTACCAGC | 503 | TAACCGGATG | 844 |
| CTTCATTTCT | 163 | CGCGTTACTG | 504 | TTCTCATCAG | 845 |
| GCCATGATAT | 164 | TTGCTCCCGT | 505 | CTCGGTTACG | 846 |
| ACGGCAAATC | 165 | CATCAAACAA | 506 | ATATGGTTCT | 847 |
| ATCGATAGTA | 166 | GCTTTATGAT | 507 | CGCCCCGAA | 848 |
| CCTAAAGGCA | 167 | CTGCATACTG | 508 | ACCTCGATCG | 849 |
| TACGAGCGGT | 168 | GGTGGCTCAG | 509 | CTCGAATAAT | 850 |
| TTTGTCGTCG | 169 | GGACGATCAA | 510 | GCCCGAGCTT | 851 |
| TACAAGCTTG | 170 | CCGACTGGTG | 511 | AACAGTCAAC | 852 |
| GACCAACACG | 171 | GGAACAACCG | 512 | CTGGAACCTC | 853 |
| GAACGACGAA | 172 | GAACGAGACC | 513 | AATAACGGGG | 854 |
| TCGGAACGCA | 173 | CACCAAGAAA | 514 | ACGCCCCACT | 855 |
| ATCCGGTGGT | 174 | ATGCATTACC | 515 | GGCAACATGA | 856 |
| TAAAACGTAG | 175 | GTATCATGCC | 516 | GCTATTTCGC | 857 |
| TATGTGAGCC | 176 | AGTAGATGTT | 517 | TTCCACTTTA | 858 |
| GAGGCATCGA | 177 | CTCTAGATGT | 518 | GCCGATGGAT | 859 |
| GAATGGGTGG | 178 | GCTACTTGTG | 519 | AAGTTGGTAA | 860 |
| AACGACACAA | 179 | TATGAAACGT | 520 | CACTAGCTAG | 861 |
| GTACGATGCA | 180 | CCTCGTTGAT | 521 | ACATGCCCCT | 862 |
| AGAAGGCGCC | 181 | CTAGAGCCAT | 522 | TTCATTACTC | 863 |
| CCGCAATGGA | 182 | TAGAGTTATA | 523 | GGTTTAATAT | 864 |
| TACGGATTTT | 183 | AACGAGAGGC | 524 | CCTGCAGTGA | 865 |
| GTCGTTAGCT | 184 | GGTCTACCGT | 525 | TCTTTAAGTT | 866 |
| GGACTAGGGC | 185 | GCCCCTCAC | 526 | TGGCGATCGA | 867 |
| ATTGGTATTC | 186 | CATAGGAATT | 527 | CTTTTTAGCT | 868 |
| ATCCCAGAGA | 187 | TCCGGCTCGT | 528 | CCCAGTCTCT | 869 |
| GTCCCAGCTC | 188 | TGAGAGTCGG | 529 | AAATGTTTCG | 870 |
| CACGAGGAAT | 189 | CGTAGAAATA | 530 | ATATAAGACG | 871 |
| TACAATTGCA | 190 | CTTTACATGA | 531 | TCACTTTACA | 872 |
| ATTCCTGAAT | 191 | GAGCGCCGTC | 532 | CCTGGCGCCC | 873 |
| TAGCGAGGCG | 192 | GGCTCTCGGC | 533 | GGATTACTGG | 874 |
| CTGGATGGGC | 193 | AGAGCTTGTT | 534 | GAATGATCTT | 875 |
| GCGACGGCCA | 194 | AATCAGCCAC | 535 | GCTCGGATCG | 876 |
| ACCTGCACAA | 195 | AGAAGAGCCA | 536 | CAGCTGCGAG | 877 |
| CATGACAGAC | 196 | TCGTATGAGT | 537 | ACCCTTACTA | 878 |
| TTACCAACGT | 197 | TTCTTCCTCG | 538 | AGGTGAAACT | 879 |
| CAGGTGTGTG | 198 | ACACAAAAGC | 539 | CGAATTTGAT | 880 |
| CGAGGGACGG | 199 | CGCGGGACCC | 540 | CGCTGTGCGG | 881 |
| CGTCTCGGTA | 200 | GTCGCGACAC | 541 | TTACCGCACC | 882 |
| TAAGCTATCT | 201 | CCGGAGGAAA | 542 | GGAATCTTAA | 883 |
| TACTCCCCTA | 202 | CGGCGTATGA | 543 | CTCAACACCC | 884 |
| TTATATTCAT | 203 | TAGGCATTCT | 544 | CGTGCCCTTG | 885 |
| AGCGATCTGC | 204 | AAAGGAGGGA | 545 | GCAGGCTCGA | 886 |
| TCTTCTGATC | 205 | ACCTTTACGG | 546 | ACCAACGAAG | 887 |
| ATAGTTCCCA | 206 | CTACCGTTAA | 547 | CCTGTAATTT | 888 |

TABLE 1-continued

| Polynucleotide Barcodes | SEQ ID NO: | Polynucleotide Barcodes | SEQ ID NO: | Polynucleotide Barcodes | SEQ ID NO: |
|---|---|---|---|---|---|
| TTTACGGGTG | 207 | GAGCTTCGCC | 548 | GGGTGGGATG | 889 |
| GTGTCCCCTG | 208 | GCCATAGAAG | 549 | TTGCTCACCG | 890 |
| GCGGGGGTCG | 209 | TTTAGCGTAT | 550 | TTACGACCAC | 891 |
| CATTGATCTA | 210 | GCAAACAGAT | 551 | TTTTCTAACC | 892 |
| AGGGACGGTG | 211 | TAGGTCATGG | 552 | GCTTTAGATA | 893 |
| CAGTTACTTT | 212 | CTCTAACAGA | 553 | CACGTATTGG | 894 |
| CCATACTTCC | 213 | GGCTCATGAA | 554 | AAATATCTCC | 895 |
| ATCAGAATTA | 214 | CAATGTCTCA | 555 | GCTGGAAAAC | 896 |
| AAACTAGGCA | 215 | TGATCGTATT | 556 | GAGCGCATTA | 897 |
| AATGTCGTTG | 216 | GCGCTTTTCA | 557 | GTGGAGGGGT | 898 |
| CACATGGGTC | 217 | AAGATTATAT | 558 | TCCACTGGGA | 899 |
| GGTCGCTGGT | 218 | ACTAGCTGAC | 559 | CAATAGCGGA | 900 |
| ACTGTATTAC | 219 | GGTGAGCTCA | 560 | CATCTAGTTT | 901 |
| CCGAGACGCG | 220 | CGCTTTCGCT | 561 | GAAGTTCCGG | 902 |
| ACTCCAACCC | 221 | TGATTCAAAA | 562 | AGCGAGATTC | 903 |
| ATATTACAAG | 222 | ACTGAACAGG | 563 | TTAAGGTCGG | 904 |
| CCATGGATAG | 223 | ATTCGAGCTA | 564 | AATGGTTAGG | 905 |
| CCGTCTCAAT | 224 | TGTAGGCTAA | 565 | CGTTATTATA | 906 |
| GATCGTCGGG | 225 | ACAAAGCTTT | 566 | ACGGAAAGGA | 907 |
| TCTTGTTTTG | 226 | GCCCGAGGGA | 567 | CCTTGTCCCG | 908 |
| AATATTGCTC | 227 | GCCCGCTGGG | 568 | ATACTTTTTT | 909 |
| AACGTCGTCT | 228 | ACCCCGCTGA | 569 | CTGGGTCTGG | 910 |
| AATATTTTTG | 229 | CTTATGCCCT | 570 | AACCATTGCG | 911 |
| CGTAACGTGC | 230 | CCGCCATAGC | 571 | AGACCGGGCC | 912 |
| GCGTGGTTAT | 231 | CTTAATGATT | 572 | TGGGACACAC | 913 |
| CAAAACATTA | 232 | CAGTCCACAA | 573 | TGCGCAGTTG | 914 |
| CGTATCCTGA | 233 | ATGGACGGAC | 574 | CGTTCGCCTT | 915 |
| TCGCTTACAA | 234 | CGGCCTCTCG | 575 | TCTCACTCGT | 916 |
| TCCATTGTGT | 235 | TAGTCGCCAT | 576 | ACACCGACGT | 917 |
| GCCCCCATTC | 236 | GTTGATCTTC | 577 | TTCAGCCCCT | 918 |
| TGACGTCTAT | 237 | ACTTGCCAAG | 578 | AGGCGACTAA | 919 |
| TGGGCCGAGG | 238 | ATGACTGGTT | 579 | TGCTATCAAG | 920 |
| AAGTGTCAAG | 239 | TGTCGTAGGA | 580 | GTCCAGTAGC | 921 |
| DACAGTAGAG | 240 | AGCAAACACG | 581 | CGTGTGGGCG | 922 |
| CGCAGCCATC | 241 | TACTGATGAA | 582 | GTGGTTCTCC | 923 |
| GAGGCAGAAC | 242 | GTATCCCATA | 583 | GCAGCCGACG | 924 |
| GTTGAAATTG | 243 | TAGCCAGGTT | 584 | GCTGTCCACG | 925 |
| ATCTGATAAA | 244 | CGTGTGGCGA | 585 | CGACACTCAT | 926 |
| AGCTGTCTCT | 245 | ATCGAATTGC | 586 | CATGGCACCT | 927 |
| TTTTAGGTTA | 246 | CCCCAATATT | 587 | TGTGACGTGT | 928 |
| TATCTGTCCG | 247 | CCCGTTTCTC | 588 | TTTTGGACTAA | 929 |
| AAAACATATG | 248 | TCCGCATCTA | 589 | TTCATGCCCG | 930 |
| GTAAAGAAGA | 249 | CAAGCCTCAT | 590 | TTGATCGTGG | 931 |
| TCGACGTGCA | 250 | TTTCAATCCC | 591 | TAGCATAGGA | 932 |
| TAGATCTTAA | 251 | CCTTCCCATC | 592 | GTAGTTGCAA | 933 |
| CACTGGTCAC | 252 | AGGTACAAGA | 593 | GGGACAGCTA | 934 |
| ATTCTGATGT | 253 | GTGTAATGGA | 594 | AAACCCCCAA | 935 |
| ATGGCCCTGA | 254 | AAACTGAGCT | 595 | ACTCTCACAA | 936 |
| GGTGATGAGA | 255 | ATCTCTGCCC | 596 | ATCATTGCCA | 937 |
| CACCGTGGGG | 256 | CGACATTTGC | 597 | CCAGTTTGCG | 938 |
| GCTTGCTCGG | 257 | TGTGAACCCG | 598 | ACATTAGTCA | 939 |
| CCAGTTGAAC | 258 | TGACACCCCA | 599 | CTCCAGGGTA | 940 |
| CGTCTGTACC | 259 | TAGGCCAAAG | 600 | GAAGGGCCAA | 941 |
| CCAACGCGGC | 260 | GAAATTGTAG | 601 | CAGTCTCCCC | 942 |
| ACGTGATCGA | 261 | GCGTCTGATT | 602 | GAGACATTCC | 943 |
| CCATCGAATC | 262 | TCTCATTGTT | 603 | AACGGTGTTG | 944 |
| CGGTGTCTGC | 263 | CTGACATCTC | 604 | AGCATTATCA | 945 |
| AAACCACCTC | 264 | GTATCCAGTG | 605 | CTATACCGAG | 946 |
| TCAATGTTCC | 265 | GATGGCCGTT | 606 | AACTGGATCA | 947 |
| TTCGACATGT | 266 | TCACCCTCTC | 607 | GTCTTGTCGG | 948 |
| AGGCACGATA | 267 | GGCACTATTC | 608 | GACGAGCCGC | 949 |
| CACGAGATCA | 268 | AAATAACTGT | 609 | GGAACACTGT | 950 |
| CATGCTGGGG | 269 | CAGCTCCATT | 610 | TAAATGCGTT | 951 |
| TACCATGGTT | 270 | CTCTTGACTC | 611 | GCGAACACAG | 952 |
| TTGCCCATAT | 271 | TTTCCTATAC | 612 | TTCTCTCAAC | 953 |
| TGCACATTCG | 272 | CCATACCCGA | 613 | GTCGTACTGA | 954 |
| GTTATGTTGG | 273 | TCGCCGAGCG | 614 | TGTGGCGTAA | 955 |
| TGAGTTATGA | 274 | CGCTGAAGCC | 615 | TGAGCGGCGT | 956 |
| GATGGCCCCC | 275 | TCTGGCCCCA | 616 | CCTCGTGAAC | 957 |
| GATGGGTTAC | 276 | GCTACATTGA | 617 | GAGCAATGAA | 958 |
| AGCTACGTTG | 277 | CGCATCATAA | 618 | CGAGACCTAA | 959 |
| ACCCCATGCA | 278 | GCAAAGGGCC | 619 | AACTGAGCGC | 960 |
| TACTACCGTT | 279 | AACGGCGCAG | 620 | TAAAGCTCGT | 961 |
| TCGCTTCTAC | 280 | CGACTGACAT | 621 | CTCTTTACGT | 962 |
| CTGGCAGTGC | 281 | ATGACAGGGC | 622 | CCCCGTGGAA | 963 |
| TCTATATATA | 282 | CAAGTTCTCC | 623 | TCGGTTCGTC | 964 |

TABLE 1-continued

| Polynucleotide Barcodes | SEQ ID NO: | Polynucleotide Barcodes | SEQ ID NO: | Polynucleotide Barcodes | SEQ ID NO: |
|---|---|---|---|---|---|
| GGATTAGTTC | 283 | TCGCCGCTTT | 624 | CTGCTTACAC | 965 |
| GTGTTACGCT | 284 | ATGCCGGAAA | 625 | ACACCGTAAT | 966 |
| TCGACTCCGT | 285 | GCGGTTACTA | 626 | CCTGGTCGGC | 967 |
| GGTAGCAGGC | 286 | GACATTACAA | 627 | GGTTATTTGG | 968 |
| TATTGGATTC | 287 | CAGAGAGGGC | 628 | GCAACTGAGT | 969 |
| GTTCGATCGA | 288 | GCACCGCCTC | 629 | ATAAGGCCTC | 970 |
| ATATTAATAT | 289 | CGGTCCGAGC | 630 | CGTGCGAAGG | 971 |
| AGAACGATTG | 290 | TGTCCGGTGC | 631 | GTCACACACT | 972 |
| GTAAAGTGTA | 291 | GGTCGGTTGC | 632 | CATACGGCAA | 973 |
| CCCATGTGCC | 292 | GCTCAGCTAA | 633 | GAACTGCCCA | 974 |
| GTGGCCTCGC | 293 | AGCAGTTCGT | 634 | AATATGTGAA | 975 |
| GACACTAGGA | 294 | AAATCGATGA | 635 | CCGATCCTGT | 976 |
| ATATTCTGAC | 295 | GCTCGGTATG | 636 | CAAAGAGCCT | 977 |
| TAAGTAGACG | 296 | CCCGCCGCGG | 637 | TAACTTAGAG | 978 |
| TAACGGTCTA | 297 | GTGTGATAGG | 638 | CAGCATGTAG | 979 |
| TAGTTTCATT | 298 | TTGGACTCCA | 639 | CCCCATGCAG | 980 |
| TTGGATCCGA | 299 | TGCTTATCTA | 640 | TCTGAACCAC | 981 |
| CGTGACAACC | 300 | CAAAAGGCGT | 641 | GCGTGCAAAA | 982 |
| CGCGCTCAGA | 301 | TAGGGGGCCT | 642 | GCTAGTACCG | 983 |
| CGTTCTTAAT | 302 | AAGTATTAAT | 643 | TTTCCCGCGC | 984 |
| ACAAGAGTTT | 303 | GTTTAGCCCG | 644 | CCTTAGTAGG | 985 |
| AGGGTTATAG | 304 | CGCTAATATG | 645 | TTGTGTCTTG | 986 |
| ACCACGACTC | 305 | ACAACACGTT | 646 | GCAACGAAGC | 987 |
| GTACTCGGGG | 306 | AGAGATGCTC | 647 | TGAAACCCTT | 988 |
| ACAAATATCT | 307 | TGCCTGATAT | 648 | TTCTACGATC | 989 |
| GATCGGGGTG | 308 | CTTGTAAGTA | 649 | ATTAAAGGTG | 990 |
| ATGTAACTCC | 309 | CATATTGCCG | 650 | TATCTAACGG | 991 |
| ATGAAGAAGC | 310 | CTTAGAAAGT | 651 | AGTGCTCCTG | 992 |
| ATGTATTGTC | 311 | ATGTTGTATT | 652 | CCGTCCCTCT | 993 |
| TGCATTGGAA | 312 | CGCATTGAAG | 653 | CTAACGAGCG | 994 |
| GCGGACGATC | 313 | TTATGTTGGT | 654 | AAGTCCGGCT | 995 |
| CCGTACTTGA | 314 | TCGCCTCAGA | 655 | GGCGTATAAG | 996 |
| TTTGCCCCCG | 315 | TTCGTTGAGG | 656 | AGATATTAGG | 997 |
| ACCTCACGCG | 316 | GGTGCCGGGC | 657 | TCCTAACAGC | 998 |
| ATTAAGGGGC | 317 | ACCATTGTAA | 658 | GAGGATACGC | 999 |
| CGTGGACATG | 318 | TTGATTGTCA | 659 | CGCTCTTTAA | 1000 |
| TTAGCCCTTC | 319 | CGGCTCACCT | 660 | ACCGGCAGGC | 328 |
| CGAGAGTTTG | 320 | CTATCACATG | 661 | GCTAAATCT | 329 |
| TGCATCCTCT | 321 | GTAGACAGAA | 662 | GCCGTTGACG | 330 |
| TGCGATTCCG | 322 | CCTTTACCAA | 663 | GGAGTTGTTG | 331 |
| TTATTACGTT | 323 | GCACATCGAC | 664 | TACTTGAGAA | 332 |
| TGATGTGGTT | 324 | TCTCACTTTC | 665 | CGGGTGCGCT | 333 |
| GGGCGTCAAT | 325 | TTCGAGTACT | 666 | AAAAGCGTCT | 334 |
| CCCTTGAAAT | 326 | TAGAAGAGCA | 667 | GTAAAGATAG | 335 |
| TCTTTGGGGC | 327 | AACCCCACCA | 668 | GCCTGGTCAG | 336 |
| ACCGGCAGGC | 328 | CTGTATCAGT | 669 | GGCAAAAAGG | 337 |
| GCTAAATCT | 329 | ACATAATGAG | 670 | ACCCTTCTCT | 338 |
| GCCGTTGACG | 330 | AGCCTTCCGC | 671 | TCACATAGTG | 339 |
| GGAGTTGTTG | 331 | CAGTGCTTTT | 672 | TCGTCTGTGC | 340 |
| TACTTGAGAA | 332 | TAGTCCGTGT | 673 | TGCTCGGATC | 341 |
| CGGGTGCGCT | 333 | CGGAATCGGT | 674 | GGCGTATAAG | 996 |
| AAAAGCGTCT | 334 | CTTGCGGAGA | 675 | AGATATTAGG | 997 |
| GTAAAGATAG | 335 | AAAAATTTGG | 676 | TCCTAACAGC | 998 |
| GCCTGGTCAG | 336 | TGTTTTCCGC | 677 | GAGGATACGC | 999 |
| GGCAAAAAGG | 337 | ATGCTAGGCG | 678 | CGCTCTTTAA | 1000 |
| ACCCTTCTCT | 338 | GACTAATTTC | 679 | GGCGTATAAG | 996 |
| TCACATAGTG | 339 | CTGTAGTAAC | 680 | AGATATTAGG | 997 |
| TCGTCTGTGC | 340 | CGGATGACTT | 681 | TCCTAACAGC | 998 |
| TGCTCGGATC | 341 | TCAGAGTGGA | 682 | GAGGATACGC | 999 |

In another embodiment, a random sequence fragment can be linked to the 5' and/or the 3' end of the polynucleotide barcode and the random sequence fragment can, for example, be used for bioinformatic removal of PCR duplicates. The random sequence fragment can also be used to add length to the nucleic acid construct and can serve as a marker for bioinformatic analysis to identify the beginning or the end of the polynucleotide barcode after sequencing. In another embodiment, the nucleic acid construct comprises at least a first and a second random sequence fragment, and the first random sequence fragment can be linked to the 5' end of the polynucleotide barcode and the second random sequence fragment can be linked to the 3' end of the polynucleotide barcode. In another embodiment, one or at least one random sequence fragment is linked to the 5' and/or the 3' end of the polynucleotide barcode. In one aspect, the random sequence fragments can be extended as needed to make the nucleic acid construct longer for different applications such as whole genome sequencing where short inserts may be lost.

In various embodiments, the random sequence fragments can be from about 5 to about 20 base pairs in length, about 5 to about 19 base pairs in length, about 5 to about 18 base pairs in length, about 5 to about 17 base pairs in length, about 5 to about 16 base pairs in length, about 5 to about 15 base pairs in length, about 5 to about 14 base pairs in length, about 5 to about 13 base pairs in length, about 5 to about 12 base pairs in length, about 5 to about 11 base pairs in length, about 5 to about 10 base pairs in length, about 5 to about 9 base pairs in length, about 5 to about 8 base pairs in length, about 6 to about 10 base pairs in length, about 7 to about 10 base pairs in length, or about 8 to about 10 base pairs in length.

In another illustrative aspect, the polynucleotide barcode may be flanked by primer binding segments (i.e., directly or indirectly linked to the polynucleotide barcode) so that the nucleic acid construct comprising the polynucleotide barcode can be amplified during a polymerase chain reaction (PCR) and/or sequencing protocol. In one aspect, the primer binding segments can be useful for binding to one or more universal primers or a universal primer set. In one illustrative embodiment, the universal primers can contain overhang sequences that enable attachment of index adapters for sequencing. In this aspect, the primers can be any primers of interest. In this embodiment, the first primer binding segment can be linked at its 3' end to the 5' end of a first random sequence fragment and the second primer binding segment can be linked at its 5' end to the 3' end of a second random sequence fragment with the polynucleotide barcode between the random sequence fragments. In another embodiment, the first primer binding segment can be linked at its 3' end to the 5' end of the polynucleotide barcode and the second primer binding segment can be linked at its 5' end to the 3' end of a random sequence fragment (see FIG. 1 for an example) linked to the 3' end of the polynucleotide barcode. In another embodiment, the first primer binding segment can be linked at its 3' end to the 5' end of a random sequence fragment and the second primer binding segment can be linked at its 5' end to the 3' end of the polynucleotide barcode where the polynucleotide barcode is linked at its 5' end to the 3' end of the random sequence fragment. In yet another embodiment, the first primer binding segment can be linked at its 3' end to the 5' end of the polynucleotide barcode and the second primer binding segment can be linked at its 5' end to the 3' end of the polynucleotide barcode.

In embodiments where primer binding segments are included in the nucleic acid construct, the primer binding segments can range in length from about 15 base pairs to about 30, from about 15 base pairs to about 29 base pairs, from about 15 base pairs to about 28 base pairs, from about 15 base pairs to about 26 base pairs, from about 15 base pairs to about 24 base pairs, from about 15 base pairs to about 22 base pairs, from about 15 base pairs to about 20 base pairs, 16 base pairs to about 28 base pairs, from about 16 base pairs to about 26 base pairs, from about 16 base pairs to about 24 base pairs, from about 16 base pairs to about 22 base pairs, from about 16 base pairs to about 20 base pairs, 17 base pairs to about 28 base pairs, from about 17 base pairs to about 26 base pairs, from about 17 base pairs to about 24 base pairs, from about 17 base pairs to about 22 base pairs, from about 17 base pairs to about 20 base pairs, 18 base pairs to about 28 base pairs, from about 18 base pairs to about 26 base pairs, from about 18 base pairs to about 24 base pairs, from about 18 base pairs to about 22 base pairs, or from about 18 base pairs to about 20 base pairs.

An exemplary sequence of a nucleic acid construct is shown below. The /5AmMC6/ is a 5' amine modification for attachment to the polymer nanoparticle. The *'s are phosphorothioate bond modifications for stability. The A*G*A*CGTGTGCTCTTCCGATCT (SEQ ID NO: 1001) sequence is the 5' primer binding segment sequence. The GCTACATAAT (SEQ ID NO: 1) is an exemplary barcode polynucleotide sequence. The N's represent the random sequence fragment. The AGATCGGAAGAGCGTCG*T*G*T (SEQ ID NO: 1002) is the 3' primer binding segment sequence.

(SEQ ID NO: 1003)
/5AmMC6/A*G*A*CGTGTGCTCTTCCGATCTGCTACA

TAATNNNNNNNNNNNAGATCGGAAGAGCGTCG*T*G*T

In all of the various embodiments described above, the entire nucleic acid construct can range in length from about 30 base pairs to about 240 base pairs, about 30 base pairs to about 230 base pairs, about 30 base pairs to about 220 base pairs, about 30 base pairs to about 210 base pairs, about 30 base pairs to about 200 base pairs, about 30 base pairs to about 190 base pairs, about 30 base pairs to about 180 base pairs, about 30 base pairs to about 170 base pairs, about 30 base pairs to about 160 base pairs, about 30 base pairs to about 150 base pairs, about 30 base pairs to about 140 base pairs, about 30 base pairs to about 130 base pairs, about 30 base pairs to about 120 base pairs, from about 30 base pairs to about 110 base pairs, from about 30 base pairs to about 100 base pairs, from about 30 base pairs to about 90 base pairs, from about 30 base pairs to about 80 base pairs, from about 30 base pairs to about 70 base pairs, from about 30 base pairs to about 60 base pairs, from about 30 base pairs to about 50 base pairs, from about 30 base pairs to about 40 base pairs, 40 base pairs to about 120 base pairs, from about 40 base pairs to about 110 base pairs, from about 40 base pairs to about 100 base pairs, from about 40 base pairs to about 90 base pairs, from about 40 base pairs to about 80 base pairs, from about 40 base pairs to about 70 base pairs, from about 40 base pairs to about 60 base pairs, from about 40 base pairs to about 50 base pairs, 50 base pairs to about 120 base pairs, from about 50 base pairs to about 110 base pairs, from about 50 base pairs to about 100 base pairs, from about 50 base pairs to about 90 base pairs, from about 50 base pairs to about 80 base pairs, from about 50 base pairs to about 70 base pairs, from about 50 base pairs to about 60 base pairs, or about 42 base pairs to about 210 base pairs.

The nucleic acid constructs are associated with the polymer nanoparticles, and exemplary polymer nanoparticle to nucleic acid construct ratio ranges are about 20:1 to about 10000:1, about 20:1 to about 9000:1, about 20:1 to about 8000:1, about 20:1 to about 7000:1, about 20:1 to about 6000:1, about 20:1 to about 5000:1, about 20:1 to about 4000:1, about 20:1 to about 3000:1, about 20:1 to about 2000:1, about 20:1 to about 1000:1, about 20:1 to about 900:1, about 20:1 to about 800:1, about 20:1 to about 700:1, about 20:1 to about 600:1, about 20:1 to about 500:1, about 20:1 to about 400:1, about 20:1 to about 300:1, about 20:1 to about 200:1, or about 20:1 to about 100:1.

In one illustrative aspect, the barcoded polymer nanoparticles may be used as delivery vehicles according to the present disclosure. In some embodiments, the non-viral delivery vehicle comprises one or more nanoparticle forming polymers. In some embodiments, the non-viral delivery vehicle comprises polymer nanoparticles. In some embodiments, the non-viral delivery vehicle is not a lipid based system. In some embodiments, the non-viral delivery vehicle comprises polymer nanoparticles made from controlled living/radical polymerization processes. It will be appreciated that the identity of the monomer units is not particularly limited so long as the monomer units being used are compatible with a controlled living/radical polymerization, such as reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, ring-opening polymerization, or like polymerization processes. In some embodiments, the polymer nanoparticles may be made by RAFT copolymerization to synthesize a diverse set of block copolymers, and to screen their ability to form complexes with a payload. In one aspect, polymer nanoparticles (e.g., RAFT copolymers) may be produced by chemically bonding a payload to a constituent polymer, such as by the grafting of the payload onto RAFT copolymers using chain transfer agents, and subsequently assembling the polymers into a delivery vehicle.

In various embodiments, payloads may be combined with the polymer nanoparticles compositions using any or all of covalent bonds, electrostatic interactions, and ligand affinity interactions. In one aspect, covalent bonding methods include the use of EDC/NHS to form stable amide bonds between the payload and the polymer nanoparticles for improved stability (both "on the shelf" and in vivo), ease of separation and extraction, and sensitive detection. In another illustrative aspect, electrostatic bonding methods include the use of cationic polymer nanoparticles that electrostatically complex with the payload. In another embodiment, ligand affinity bonding includes the use of ligands such as avidin and biotin, both covalently bonded to the polymer nanoparticles and the payload via EDC/NHS chemistry to yield the stable combination of the payload and the polymer nanoparticles.

It will be appreciated that RAFT polymerization is generally known in the art. Suitable reagents, monomers, and conditions for RAFT polymerization previously investigated can be used in the copolymers, methods, and compositions described herein, such as those described in U.S. Pat. Nos. 9,006,193, 9,464,300, and 9,476,063, the disclosures of each of which are incorporated by reference in their entirety.

Chain transfer agents (CTAs) useful in connection with the present disclosure are known in the art. The identity of the CTA is not particularly limited. It will be appreciated that chain transfers steps that form the basis of RAFT polymerization involve a reversible transfer of a functional chain end-group (typically a thiocarbonylthio group, Z—C(=S) S—R) between chains and the propagating radicals. The overall process is comprised of the insertion of monomers between the R— and Z—C(=S)S-groups of a RAFT agent (CTA), which form the α and ω end-group of the majority of the resulting polymeric chains. Suitable CTAs for use in connection with the present disclosure include but are not limited to trithiocarbonates (Z=S-alkyl), dithiobenzoates (Z=Ph), dithiocarbamate (Z=N-alkyl), xanthates (Z=O-alkyl), and the like. (See, Sébastien Perrier, *Macromolecules* 2017 50 (19), 7433-7447) In some embodiments, RAFT copolymerization may be achieved using chain transfer agents (CTAs) containing one or more terminal carboxyl groups in order to obtain carboxy terminated polymers with ends available for bonding to the payload via the methods described above. In this embodiment, when the resulting mono or di-carboxy terminated polymer is dispersed in a low pH (e.g., a pH of less than 6) buffer, both ends of the polymer are exposed and available for labeling via EDC/NHS chemistry. In this embodiment, when the polymer is transferred to a physiological pH (~pH 7), the core blocks self-assemble, encapsulating the payload in the hydrophobic core, to be released and exposed upon acidification in the endosomal compartment of a cell. In some embodiments, the first or second chain transfer agent can be selected from the group consisting of bis(carboxymethyl)trithiocarbonate, bis (2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl)thio)pentanoic acid, and 4-cyano-4-[(dodecylsulfanylthiocarbonyl)sulfanyl] pentanoic acid, 4-cyano-4-(thiobenzoylthio)pentanoic acid, 2-cyano-2-propyl benzodithioate, cyanomethyl methyl(phenyl)carbamodithioate, 2-cyano-2-propyl dodecyl trithiocarbonate, 2-(dodecylthiocarbonothioylthio)-2-methylpropionic acid, cyanomethyl dodecyl trithiocarbonate, 2-cyano-2-propyl 4-cyanobenzodithioate, and the like.

It will be apprectiated that RAFT useful in connection with the present disclosure can be of a variety of polymer compositions. For example, RAFT polymers useful in connection with the present disclosure can be a random block polymer comprising a single polymer block, or a diblock RAFT copolymer comprising two polymer blocks, or a triblock RAFT copolymer comprising three polymer blocks, or further numbers of blocks can be used. The skilled person will readily appreciate that the preparation of block polymers by RAFT polymerization is known in the art and that such polymerization processes can be applied to the present disclosure. (See, Goby, et. al., Nat. Commun. 4:2505 doi: 10.1038/ncomms3505 (2013))

In some embodiments, RAFT copolymers as prepared herein can be described by the following structure:

where each CTACap is a capping unit derived from the chain transfer agent(s) used in the process for preparing the RAFT copolymer. The CTA used for preparing each of Block 1 and Block 2 can be the same or different. In some embodiments, the CTA used to prepare each of Block 1 and Block 2 is the same (e.g. macroCTA). In some embodiments, the CTA used to prepare each of Block 1 and Block 2 is different. In some embodiments, the CTA used to prepare one or both of Block 1 and Block 2 comprises a functional group for the covalent attachment of a biomolecule, drug, or label to the RAFT copolymer. In some embodiments, the covalent attachment can be via an ester or an amide bond. In some embodiments, the covalent attachment can be via EDC-NHS chemistry. In some embodiments, the first capping unit is of the formula

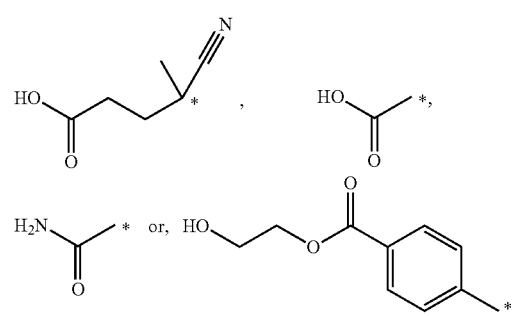

wherein * represents a point of covalent attachment to the first block. In some embodiments, the second capping unit is of the formula

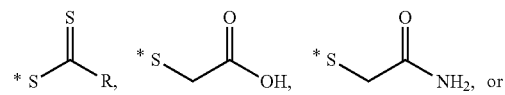

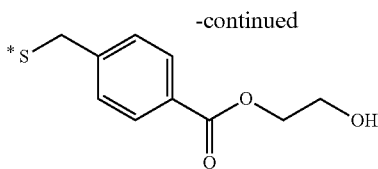

wherein * represents a point of covalent attachment to the second block, and R is —$SC_2$-$C_{12}$ alkyl or $C_6H_5$, In some embodiments, the RAFT copolymer can be associated with a DNA molecule, in particular a nucleic acid construct of the present disclosure, via several methods including, electrostatic interaction, high affinity, non-covalent bond, avidin-streptavidin conjugation, or by direct covalent attachment through, for example, an amide bond. In some embodiments, the RAFT copolymer can be associated with a DNA molecule, in particular a nucleic acid construct of the present disclosure, via electrostatic interaction complexed with a biological molecule. In some embodiments, the RAFT copolymer can be associated with a DNA molecule, in particular a nucleic acid construct of the present disclosure, via electrostatic interaction complexed with a biological molecule. In some embodiments, the RAFT copolymer can be associated with a DNA molecule, in particular a nucleic acid construct of the present disclosure, via a high affinity, non-covalent bond, avidin-streptavidin conjugation. In some embodiments, the RAFT copolymer can be associated with a DNA molecule, in particular a nucleic acid construct of the present disclosure, by direct covalent attachment through, for example, an amide bond.

As shown in FIGS. 5(a)-5(e), the PNPs described herein can be associated with a nucleic acid construct of the present disclosure via electrostatic interaction, avidin-streptavidin conjugation, or by direct covalent attachment. Briefly, as shown in FIGS. 5(a)-5(e), the labels provided in the figure are as follows: 001. Polymer nanoparticle (PNP) with positively charged corona in the case of electrostatic loading. 002. Nucleic acid constructs with negative charges due to the phosphate groups. 003. Electrostatically loaded PNP-nucleic acid construct complex. 004. Carboxylate group on the terminal end of the polymer chains in the corona of the PNP. 005. Primary amine group on the 5' end of the amine terminated nucleic acid construct. 006. Phosphate group on the 3' end of the nucleic acid construct. 007. Amide bond formed in the direct amidification reaction between the amine terminal nucleic acid construct and the carboxylate terminated PNP. 008. Primary amine on the biotin bonding protein such as avidin. 010. Amide bond formed between the carboxylate group on the terminal end of the polymer chains in the corona of the PNP and the primary amine on the biotin bonding protein such as avidin. 011. Nucleic acid construct with a biotin functional group on the 5' terminus. 012. Electrostatic coupling reaction that occurs when positively charged PNPs are mixed with negatively charged nucleic acid constructs. 013. Direct amidification reaction that is carried out via an EDA-NHC reaction between the carboxylate group on the terminal end of the polymer chains in the corona of the PNP and the primary amine on the amine terminated nucleic acid constructs. 014 Direct amidification reaction that is carried out via an EDA-NHC reaction between the carboxylate group on the terminal end of the polymer chains in the corona of the PNP and the primary amine on the biotin bonding protein such as avidin. 015. Coupling of the biotin on the 5' end of the nucleic acid construct and the avidin conjugated to the carboxylate terminus on the corona of the PNPs.

In some embodiments, each of Block 1 and Block 2 can comprise one or more monomer units polymerized using a RAFT polymerization process. It will be appreciated that the identity of the monomer units is not particularly limited so long as the monomer units being used are compatible with a controlled living/radical polymerization, such as reversible-deactivation radical polymerization, atom transfer radical polymerization (ATRP), reversible addition fragmentation chain transfer polymerization (RAFT), iodine-transfer polymerization (ITP), selenium-centered radical-mediated polymerization, telluride-mediated polymerization (TERP), stibine-mediated polymerization, ring-opening polymerization, or like polymerization processes. Suitable monomer units include but are not limited to 2-dimethylaminoethyl acrylate (DMAEMA), 2-(diethylamino) ethyl methacrylate (DEAEMA), 2-(diisopropylamino) ethyl methacrylate (DPAEMA), butyl methacrylate (BMA), ethyl acrylic acid (EAA), propyl acrylic acid (PAA), (hydroxyethyl)methacrylate (HEMA), methyl methacrylate (MMA), Acrylic acid (AA), Acetoacetanilide (AAA), 4-Aminobenzonitrile (ABN), 9-Anthracenylmethyl acrylate (ACMA), 9-Anthracenylmethyl methacrylate (ACMMA), Aminoethyl methacrylate (AEM), 2-(2-aminoethylamino) ethyl methacrylate (AEAEMA), 4-(2-Acryloxyethoxy)-2-hydroxybenzophenone (AEHBP), 2-Aminoethyl methacrylate (AEMA), N-(2-Aminoethyl) methacrylamide (AEMAA), 3-amino-2-hydroxypropyl methacrylate (AEAHPMA), 3-aminopropyl methacrylamide (AHPMA), Allyl methacrylate (ALMA), Acrylamide (AM), Amidoamine (AMA), 3-Methacryl amido-3-methylbutanoic acid (AMBA), 2-Allyloxybenzaldehyde (AOBA), [2-(Acryloyloxy)ethyl]trimethylammonium chloride (AOETMA), 3-(Acryloyloxy)-2-hydroxypropyl methacrylate (AOHOPMA), 4-Aminophenethyl alcohol (APA), N-(3-Aminopropyl)methacrylamide (APMA), 5-(3-(Amino)-propoxy)-2-nitrobenzyl methacrylate (APNBMA), N—[N'-(2-aminoethyl)-2-aminoethyl]aspartamide (Asp (DET)), 2-Azidoethyl Methacrylate (AzEMA), 2,2'-Bithiophene (2-2-BTP), tert-Butyl acrylate (BA), Bromoacetaldehyde diethyl acetal (BAADA), N-(t-BOC-aminopropyl) methacrylamide (BAPMAA), tert-Butyl 2-bromoacrylate (BBA), 4-Butylbenzoyl chloride (BBC), 1,3-Butadiene (BD), 2-Butyl-2-ethyl-1,3-propanediol (BEPD), Di-tert-butyl iminodiacetate (BIDA), 3-(Bromomethyl)-5-((trimethylsilyl)ethynyl)benzenesulfonyl fluoride (BMTMSEBS), 2-(Benzyloxy)ethanol (BOE), 4-tert-Butoxystyrene (BOS), Branched polyethyleneimine (BPEI), 3-Bromo-5-((trimethylsilyl)ethynyl)benzenesulfonyl fluoride (BTMSEBS), ε-Caprolactone (CAP), Carboxybetaine methacrylate (CBMA), 2-Cyanoethyl N,N-diisopropylchlorophosphoramidite (CEDPCPP), N-Cyclohexylmaleimide (CHMI), 3-Chloro-2-hydroxypropyl methacrylate (CHPMA), Dodecyl acrylate (DA), N,N-Diallylacrylamide (DAA), Diallylmethylamine (DAMA), Diallyldimethylammonium chloride (DADMAC), 2,5-Diaminopyridine (DAP), 5,5'-Dibromo-4,4'-didodecyl-2,2'-bithiophene (DBDDBT), 5,5'-Dibromo-4,4'-ditetradecyl-2,2'-bithiophene (DBDTBT), 2,5-Dibromo-3-hexylthiophene (DBHTP), Dichloromethylvinylsilane (DCMVS), 2-(Diethylamino)ethanethiol hydrochloride (DEAET), 2-(Diethylamino)ethyl methacrylate (DEAEMA), Diethyl oxalpropionate (DEOP), DL-Lactide (DLL), N,N-dimethylamino-2-ethylmethacrylate) (DMA), N-[3-(N,N-dimethylamino)propyl]-methacrylamide (DMAPMA), [2-(Methacryloyloxy)ethyl]dimethyl-(3-sulfopropyl)ammonium hydroxide (DMAPS), N,N'-dimethylbutylamine (DMBA), N,N'-dimethylethanolamine (DMEA), N,N-dimethylamino-2-ethylacrylate or 2-(dimethylamino)ethyl acrylate (DMAEA), 1-(Dimethylamino)pyrrole (DMAP), 4,5-Dimethoxy-2-nitrobenzyl alcohol (DMONBA), 3,4-Dimethoxythiophene (DMOT), 1,2-Dimyristoyl-sn-glycero-3-phosphocholine (DMPC), 2-deoxy-2-methacrylamido glucopyranose (DOMAAG), 1,2-Dioleoyl-sn-glycero-3-phosphocholine (DOPC), 1,2-Dioleoyl-sn-glycero-3-phosphoethanolamine (DOPE), 1,4,7,10-Tetraazacyclododecane-1,4,7,10-tetraacetic acid (DOTA), 1,2-Dioleoyl-3-trimethylammonium Propane (DOTAP), 1,2-Diphytanoyl-sn-glycero-3-phosphoethanolamine (DPyPE), 3-Dodecylthiophene (3-DT), N-[2-(2-pyridyldithio)]ethyl methacrylamide (DTEMA), Ethyl acrylic acid (EAA), Ethyl 2-(bromomethyl)acrylate (EBMA), Ethyl 1-cyano-1-cyclopropanecarboxylate (ECCPC), 3,4-Ethylenedioxythiophene (EDOT), Ethylene glycol dimethacrylate (EGDMA), Ethylene glycol phenyl ether acrylate (EGPEA), Ethyl methacrylate (EMA), 3-(Fluorosulfonyl)-5-((trimethylsilyl)ethynyl)benzoic acid (3FTMSEBA), 3-Formyl-5-((trimethylsilyl)ethynyl)benzenesulfonyl fluoride (3FTMSEBS), 4-Formyl-2-((trimethylsilyl)ethynyl)benzenesulfonyl fluoride (4FTMSEBS), 5-Fluoro-2,3-thiophenedicarboxaldehyde (SFTPDCA), N-acetyl-D-galactose (GalNAc), N-acetyl-D-glucose (GlcNAc), Glycidyl methacrylate (GMA), Glycosylphosphatidylinositol (GPI), 5,7-Hexadecadiynoic acid (HDDA), 2-Hydroxyethyl methacrylate (HEMA), 1,1,1,3,3,3-Hexafluoroisopropyl acrylate (HFIPA), 1,1,4,7,10,10-Hexamethyltriethylenetetramine (HMTETA), 4-Hydroxybutyl acrylate (HOBA), 2-(4-Hydroxyphenylazo)benzoic acid (HPABA), 2,2,3,3,4,4,4-Heptafluorobutyl acrylate (HPFBA), N-(2-Hydroxypropyl)-Methacrylamide (HPMA), 2,2,3,4,4,4-Hexafluorobutyl acrylate (HXFBA), Isobornyl acrylate (IBA), 4-Iodobenzoyl chloride (IBC), Isobornyl methacrylate (IBMA), N-(Isobutoxymethyl)acrylamide (IBMAA), Isodecyl acrylate (IDA), Maleic anhydride (MA), [2-(Methacryloyloxy)ethyl] trimethylammonium chloride (MAETMA), Methacryloyl-L-Lysine (MAL), Methacryloxysuccinimide (MAS), Methacrylamidotrehalose (MAT), Methyl heptadecanoate (MHD), 1-Methyl-1H-indole-3-carbaldehyde (MICA), 2-N-Methylmaleimide (MMI), Methyl-5-norbornene-2,3-dicarboxylic anhydride (MNDCA), Methoxyethyl methacrylate (MOEMA), 2-(2-Methoxyethoxy)ethyl methacrylate (MOEOEMA), 3-Methyl-3-oxetanemethanol (MOM), 2-Methacryloyloxyethyl phosphorylcholine (MPC), Methyl 4-vinylbenzoate (MVB), 2-Naphthyl acrylate (NA), N-(Acryloxy)succinimide (NAS), o-Nitrobenzyl methacrylate (NBMA), N-Hydroxysuccinimide (NHS), N-(Methacryloxy)succinimide methacrylate (NHSMA), N-Isopropylacrylamide (NIPAM), 2-Naphthyl methacrylate (NMA), N-(Methacryloyloxy)succinimide (NMS), N-(n-Octadecyl)acrylamide (NODAA), 4-Nitro-N-propylbenzylamine hydrochloride (NPBAHC), Oligoethylene glycol methacrylate (OEGMA), Oligoethylenimine (OEI), 3-Phenylthiophene (3-PTP), Poly(N-methyl 4-vinylpyridine iodide) (P4VPQ), Poly(2-aminoethylmethacrylamide) (PAEMA), N—(N'—{N''—[N'''-(2-aminoethyl)-2-aminoethyl]-2-aminoethyl}-2-aminoethyl)-aspartamide (Asp(TEP)), 4-Pentenoic anhydride (PAN), Pentabromobenzyl acrylate (PBBA), Pentabromobenzyl methacrylate (PBBMA), Pentabromophenyl acrylate (PBPA), Pentabromophenyl methacrylate (PBPMA), Poly (ε-caprolactone) (PCL), trans-2-Phenylcyclopropyl isocyanate (PCPI), 1,5-Pentanediol (PD), 2-Phenyl-1,3-dioxan-5-ol (PDO), Pyridyl disulfide ethyl methacrylate (PDSEMA), Poly(ethylene glycol) (PEG), Poly(ethylene glycol) acrylate (PEGA), Poly(ethylene glycol) methyl ether methacrylate (PEGMEMA, Poly(ethylene glycol) ethyl ether methacrylate (PEGEEMA), Poly(ethylene glycol) methacrylate (PEGMA), Pentaethylenehexamine (PEHA), Poly(ethylenimine) (PEI), Pentaerythritol tetraacrylate (PETA), Pentafluorophenyl (PFP), Pentafluorophenyl acrylate (PFPA), Pentafluorophenyl methacrylate (PFPMA), Poly(glutamic acid) (PGA), Poly-(glycoamidoamine) (PGAA), Poly(glycidylbutylamine) (PGBA), Poly(glycidyl methacrylate) functionalized with ethanolamine (PGEA), Poly(glycidyl methacrylate) (PGMA), Poly(N-(2-Hydroxypropyl)methacrylamide) (PHPMA), Poly(lactic acid) (PLA), Poly(L-glutamate), (PLG), Poly(lactic-co-glycolic acid) (PLGA), Poly(L-lysine) (PLL), Poly(L-lactic acid) (PLLA), Poly (lauryl methacrylate) (PLMA), Poly(methacrylic acid) (PMAA), Poly-(2-deoxy-2-methacrylamido glucopyranose) (PMAG), Poly-(methyl methacrylate) (PMMA), Poly(2-methacryloyloxyethyl phosphorylcholine) (PMPC), Poly[N-(3-(methacryloylamino) propyl)-N,N-dimethyl-N-(3-sulfopropyl) ammonium hydroxide] (PMPD), Poly(n-butyl acrylate) (PnBA), Poly(n-butyl methacrylate) (PnBMA), Poly(N-isopropyl acrylamide) (PNIPAM), Poly(oligoethylene glycol methacrylate) (POEGMA), Poly(propylene glycol) (PPG), Poly(propylenimine) (PPI), 3,4-Propylenedioxythiophene (ProDOT), Poly(styrene) (PS), Poly(sodium 4-styrenesulfonate) (PSS), Poly(tributyl-(4-vinylbenzyl) phosphonium chloride) (PTBP), Poly(triethyl-(4-vinylbenzyl)phosphonium chloride) (PTEP), Poly((2-trimethylamino)ethyl metacrylate chloride) (PTMAEMA), Poly ((vinylbenzyl) trimethylammonium) (PVBTMA), Poly(2-vinyl-4,4-dimethylazlactone) (PVDMA), Poly(N-ethyl-4-vinylpyridinium bromide) (PVP), Quaternized Poly-DMAEMA (QPDMAEMA), Sulfobetaine methacrylate (SBMA), 3-Sulfopropyl methacrylate potassium salt (SP-MAP), Thiocholesterol (TC), Thiophene-2,5-diboronic acid bis(pinacol) ester (TDABP), Triethylene glycol dimethacrylate (TEGDMA), Trifluoroethylene (TFE), 2,2,2-Trifluoroethyl acrylate (TFEA), 2,2,2-Trifluoroethyl methacrylate (TFEMA), Tetrahydrofurfuryl acrylate (THFA), Triallylisocyanurate (TIC), Trimethylene Carbonate (TMC), 4,4'-Trimethylenedipiperidine (TMDP), Trimethylolpropane tris(3-mercaptopropionate) (TMPTMP), (Trimethylsilyl) methacrylate (TMSMA), Triphenylcarbenium pentachlorostannate (TPCPCS), 3-Vinylbenzaldehyde (3VBA), 4-Vinylpyridinium chloride (4VP), Vinyl acrylate (VA), Vinyl acetate (VAT), 4-Vinylbenzoic acid (VBA), (Vinylbenzyl)trimethylammonium chloride (VBTAC), 1-Vinylimidazole (VI), 1-Vinyl-2-pyrrolidone (VP), m-Xylylenediamine (XDA), Zinc stearate (ZS), and the like.

In some embodiments, the monomer units used to make Block 1 and/or Block 2 of RAFT copolymers as described herein are selected from the group consisting of 2-(dimethylamino) ethyl acrylate (DMAEEA), 2-(diethylamino) ethyl methacrylate (DEAEEA), 2-(diisopropylamino) ethyl methacrylate (DIEAMA), butyl methacrylate (BMA), ethyl acrylic acid (EAA), propyl acrylic acid (PAA), (hydroxyethyl)methacrylate, and methyl methacrylate (MMA).

In some embodiments, the RAFT copolymers provided herein can be described by the formula:

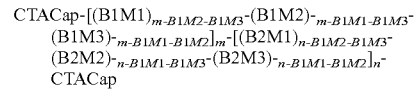

For example, a RAFT copolymer as described herein having a single monomer in Block 1 of 25 units and 3 different monomers in Block 2 having an average monomer unit ratio of 20:10:5 for a total n of 35, can be described by the general formula

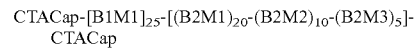

It will be further appreciated that the polymers prepared using a RAFT polymerization are random polymers having a distribution of units and hence molecular weights. Therefore, the cartoon representation of Block 2 in the example above is a random copolymer comprising 35 monomer units of B2M1, B2M2, and B2M3 in the ratio described above.

In another illustrative embodiment, the polymer nanoparticle composition can be coated with one or more polymers to protect the compositions from immune responses or to enhance endosomal escape. In one embodiment, the one or more polymers comprise polyethylene glycol. In another embodiment, the one or more polymers comprise polyethylene glycol poly-L-lysine. In yet another embodiment, the one or more polymers comprise polyethylenimine. In an additional embodiment, the one or more polymers comprise polyethylene glycol poly-L-lysine and polyethylenimine.

It will be appreciated that tuning the parameters and properties of the RAFT copolymers described herein can be advantageous to their use in the compositions and methods as described herein. Accordingly, the methods for preparing RAFT copolymers either in singleton or in library format as described herein are capable of providing particular parameters and properties of the RAFT copolymers.

In some embodiments, a RAFT block polymer as described herein has one or more of an overall molecular weight ($M_n$) (i.e. the total of all blocks) in the range of about 1 kDa to about 1000 kDa, or about 2 kDa to about 500 kDa, or about 2 kDa to about 160 kDa, and overall degree of polymerization in the range of about 10 to about 3500, or about 20 to about 2500, or about 30 to about 900, a size in the range of about of about 10 nm to about 10000 nm, and a maximum corona-to-core ratio (CCR) of about 1 to about 4. In some embodiments, the overall molecular weight ($M_n$) in the range of about 30 kDa to about 120 kDa, about 40 kDa to about 110 kDa about 50 kDa to about 100 kDa, about 60 kDa to about 90 kDa, about 40 kDa to about 80 kDa, and about 40 kDa to about 60 kDa. In some embodiments, the overall degree of polymerization in the range of about 40 to about 850, about 60 to about 800, about 100 to about 700, about 200 to about 600, or about 300 to about 500. In some embodiments, the size is in the range of about of about 10 nm to about 10000 nm, or about 20 nm to about 5000 nm, or about 50 nm to about 3000 nm, or about 20 nm to about 1000 nm, or about 50 nm to about 1000 nm, or about 30 nm to about 500 nm, or about 200 nm to about 2000 nm, or about 100 nm to about 5000 nm, or about 100 nm to about 500 nm, or about 10 nm to about 50 nm, about 15 nm to about 45 nm, about 20 nm to about 40 nm, or about 25 nm to about 35 nm. In some embodiments, the maximum corona-to-core ratio (CCR) is less than 4, or less than 3, about 1 to about 3.8, about 1.2 to about 3.5, about 1.5 to about 3, about 1.5 to about 2.5, or about 1 to about 2.

In some embodiments, a first block can be prepared from one or more monomer units and have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, a first block molecular weight ($M_n$) can be in the range of about 1 kDa to about 500 kDa, or about 2 kDa to about 400 kDa, or about 5 kDa to about 200 kDa, or about 10 kDa to about 160 kDa, or about 15 kDa to about 100 kDa, or about 25 kDa to about 60 kDa, or about 30 kDa to about 55 kDa, about 30 kDa to about 50 kDa, or about 30 kDa to about 40 kDa, and the like. In some embodiments, the first block degree of polymerization is in the range of about 30 to about 350, about 50 to about 300, about 70 to about 250, about 80 to about 240, about 100 to about 200, and the like.

In some embodiments, the second block can be prepared from one or more monomer units, and can have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, the second block molecular weight ($M_n$) is in the range of about 10 kDa to about 70 kDa, about 15 kDa to about 65 kDa, about 20 kDa to about 60 kDa, about 25 kDa to about 55 kDa, about 30 kDa to about 50 kDa, about 35 kDa to about 45 kDa, about 5 kDa to about 15 kDa, and the like. In some embodiments, the second block degree of polymerization is in the range of about 3 to about 2500; or about 20 to about 2000, or about 30 to about 1500, or about 40 to about 1200, or about 10 to about 500, or about 12 to about 450, or about 20 to about 400, or about 25 to about 350, or about 50 to about 300, or about 100 to about 250, or about 150 to about 200, or about 5 to about 50, or about 5 to about 20, and the like.

In some embodiments, a third, fourth, or subsequent block can be prepared from one or more monomer units, and each can have a molecular weight ($M_n$) in the range of about 1 kDa to about 500 kDa, or about 10 kDa to about 200 kDa, or about 10 kDa to about 160 kDa, or about 1 kDa to about 80 kDa, and a degree of polymerization in the range of about 10 to about 3500, or about 10 to about 2500, or about 20 to about 2000, or about 50 to about 1200, or about 50 to about 1000. In some embodiments, the third, fourth, or subsequent block molecular weight ($M_n$) is in the range of about 10 kDa to about 70 kDa, about 15 kDa to about 65 kDa, about 20 kDa to about 60 kDa, about 25 kDa to about 55 kDa, about 30 kDa to about 50 kDa, about 35 kDa to about 45 kDa, about 5 kDa to about 15 kDa, and the like. In some embodiments, the third, fourth, or subsequent block degree of polymerization is in the range of about 3 to about 2500; or about 20 to about 2000, or about 30 to about 1500, or about 40 to about 1200, or about 10 to about 500, or about 12 to about 450, or about 20 to about 400, or about 25 to about 350, or about 50 to about 300, or about 100 to about 250, or about 150 to about 200, or about 5 to about 50, or about 5 to about 20, and the like.

In some embodiments, a single chain transfer agent can be used in the RAFT polymerization process in connection with the present disclosure. In some embodiments, for a block polymer having more than one block, one or more single chain transfer agents can be used in the RAFT polymerization process in connection with the present disclosure. In some embodiments, for a block polymer having two blocks, a first chain transfer agent and a second chain transfer agent (which can be the same or different) can be used at each step of the RAFT polymerization process in connection with the present disclosure. In some embodiments, for a block polymer having three blocks, a first chain transfer agent, a second chain transfer agent, and a third chain transfer agent (which can be the same or different) can be used at each step of the RAFT polymerization process in connection with the present disclosure.

It will be appreciated that a variety of solvents can be used in the RAFT polymerization method steps and purification steps described herein. Suitable solvents include, but are not limited to, 2-Chloroethanol, Acetic Acid (Glacial), Acetone, Acetonitrile, Acetophenone, Aniline, Benzaldehyde, Benzyl Acetate, Carbon disulfide, Cyclohexane, Cyclohexanol, Di(ethylene glycol), Di(propylene glycol), Diacetone alcohol, Diethyl ether, Dimethylsulfoxide, Ethanol, Ethyl acetate, Ethylene glycol, Formaldehyde (37% solution), Formamide, Formic acid, Formic acid (96%), Hexanelsobutanol, Isopropanol, Isopropyl acetate, Isopropyl ether, m-Cresol, Methanol, Methyl acetate, Methyl ethyl ketone, Mineral Oil, N,N-Dimethylformamide, n-Butanol, n-Octane, n-Propanol, Propylene glycol, Pyridine, t-Butanol, Tetrahydrofuran, Trifluoroacetic acid, water, and the like, and combinations thereof.

In some embodiments, the one or more nanoparticle forming polymers are RAFT block copolymers comprising
  a. a first terminus comprising a first capping unit derived from a first chain transfer agent in a RAFT copolymerization process;
  b. a first block prepared from one or more monomer units covalently attached to the first reactive functional unit, and having a molecular weight ($M_n$) in the range of about 1 kDa to about 500 kDa and a degree of polymerization in the range of about 10 to about 2500;
  c. optionally a second block prepared from one or more monomer units covalently attached to the first block, and having a molecular weight ($M_n$) in the range of about 1 kDa to about 500 kDa and a degree of polymerization in the range of about 10 to about 2500;
  d. optionally a third block prepared from one or more monomer units covalently attached to the first and/or second blocks, and having a molecular weight ($M_n$) in the range of about 1 kDa to about 500 kDa and a degree of polymerization in the range of about 10 to about 2500;
  e. optionally a fourth block prepared from one or more monomer units covalently attached to the first, second, and/or third blocks, and having a molecular weight ($M_n$) in the range of about 1 kDa to about 500 kDa and a degree of polymerization in the range of about 10 to about 2500;
  f. optionally a fifth block prepared from one or more monomer units covalently attached to the first, second, third, and/or fourth blocks, and having a molecular weight ($M_n$) in the range of about 1 kDa to about 500 kDa and a degree of polymerization in the range of about 10 to about 2500; and
  g. a second terminus comprising a second capping unit derived from a first, a second, a third, or a fourth chain transfer agent.

Illustrative payloads for the polymer nanoparticle described herein can include any one or a combination of compositions selected from the group comprising: nucleic acids (e.g., DNA or RNA), pDNA, oligodeoxyribonucleic acids (ODNs), dsDNA, ssDNA, antisense oligonucleotides, antisense RNA, siRNA, messenger RNA, guide RNA (e.g., small guide RNA), ribonucleoproteins, donor DNA strands used in the CRISPR/Cas9 system, and enzymes, such as CRISPR-associated enzymes, e.g., Cas9, enzymes used in other gene editing systems, such as ZFNs, custom designed homing endonucleases, TALENS systems, other gene editing endonucleases, and reverse transcriptase.

In another aspect, the present disclosure rapidly identifies top candidates using a machine learning model. In the illustrative embodiment, a graph neural network (GNN) is used for this process. Polymers can be characterized at three scales: monomer, block, and full polymer. Monomers combine to form blocks, and blocks combine to form full polymers. Polymer properties are dependent on characteristics of the polymer at all three scales. The relationships between monomers, blocks, and polymers can be captured with a directed graph. Information can then be shared between nodes in the graph to create a numerical representation of the full polymer at all three scales: monomer, block, and polymer. These numerical representations can then be used in a neural network to prediction properties of the polymer. The use of a GNN for polymer property prediction in the illustrative embodiment provides two primary benefits: first, the graph can model polymer characteristics at all three scales which is important for accurate prediction; second, the graph provides a flexible modeling structure that can accommodate several polymer structures.

Figure 3A:
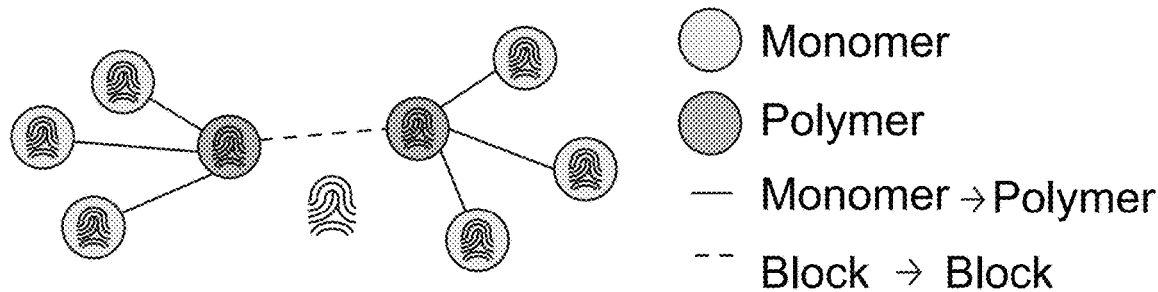
FIG. 3(a)-3(b) are schematic diagrams showing graph neural network architecture (3(a)) and Zeta potential prediction from SMILES input (3(b)).

The machine learning model is first trained on a combination of public data and preliminary testing data, supplemented with the large data sets described above. The illustrative embodiment involves a three-loop deep learning cycle to accelerate high-throughput characterization and screening for PNPs. The three deep learning loops characterize the PNP physical properties, in vitro bioactivity, and in vivo bioactivity, respectively. Each loop utilizes a GNN deep learning model (see FIG. 3a) to characterize the candidate PNPs. The GNN takes the simplified molecular-input line-entry system (SMILES) strings defining the monomers as an input (the nodes of the graph), and the edges of the graph define the relationship between the monomers and how they combine to form the PNP. The edges of the graph also allow additional information about the polymer (e.g., ratios of monomers and degree of polymerization) to be incorporated into the GNN.

Figure 3B:
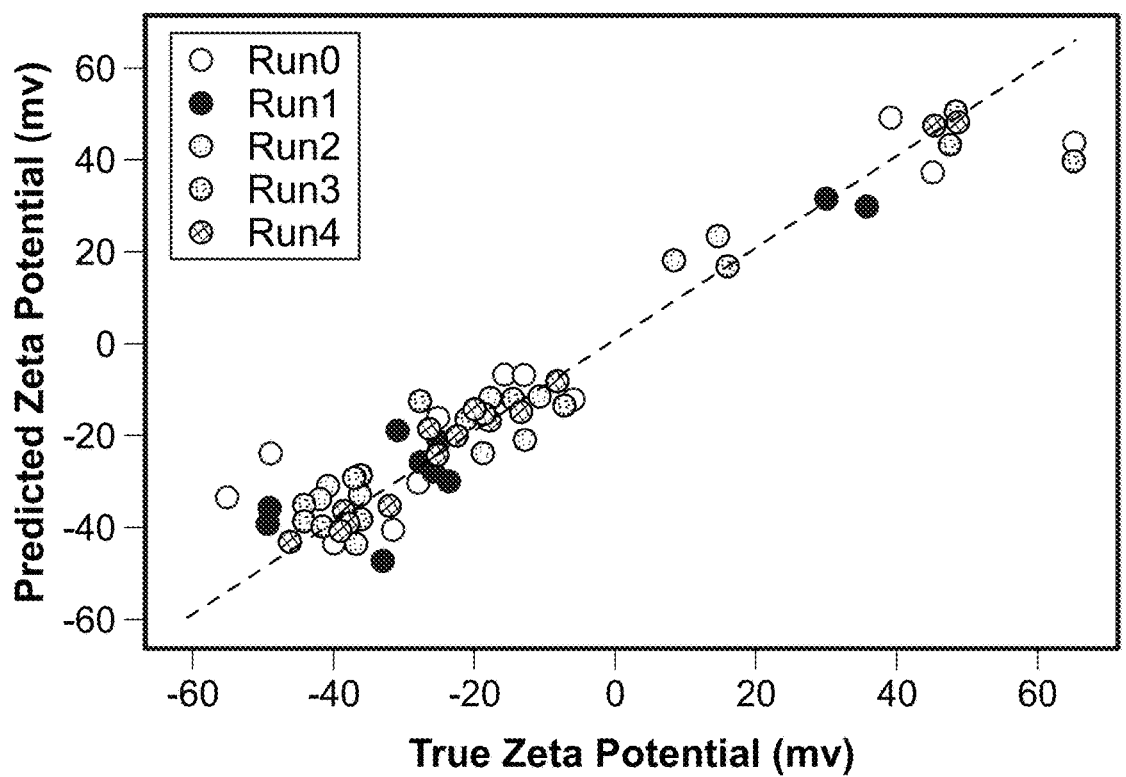

The presently disclosed architecture offers at least three distinct advantages. First, the deep learning model is not dependent on polymer fingerprinting. Rather, the deep learning model will learn an appropriate numerical embedding from the SMILES strings. Second, the graph allows the model the flexibility to represent various families of PNPs with ease. Third, using SMILES strings as inputs allows the limited training dataset to be augmented with enumerated SMILES strings, increasing the amount of training data available and improving the model performance. Testing of this GNN architecture has shown impressive ability to predict zeta potential (see FIG. 3b), a critical characteristic for non-viral gene delivery vehicles. Once trained, these deep learning models will be used to prioritize the synthesis and characterization of candidate PNPs in the high-throughput system to meet the requirements of a bioactivity. Iterative data can be used to fine-tune the models in an active learning cycle to improve future performance.

In some embodiments, data augmentation may be performed to artificially increase the size and variety of the data used to train the machine learning model (and, consequently, increase model performance). Deep learning models require relatively large datasets for training and can over-fit to small datasets. As discussed above, the GNN takes the SMILES strings defining the monomers as an input. A monomer (a building block of a polymer) has a single canonical SMILES string, but it also has multiple alternative SMILES string representations. SMILES enumeration can be performed to generate these alternative forms from the canonical SMILES string and, thus, increase the size of the training data set many times over. The neural network model is then able to leverage this increase in data size and variety of representations to improve performance.

In other embodiments, a modified Transformer model (rather than a GNN) may be used to predict polymer properties (and, thus, rapidly identify top candidates for non-viral carriers for delivering base editing proteins, among other applications). The modified Transformer model exploits relative positional information of inputs to create numerical embeddings for monomer string inputs. These numerical embeddings can then be used in deep learning and statistical models for polymer property prediction. Additionally, the Transformer model is more computationally efficient compared to many other deep learning architectures that can process sequential data. The original Transformer architecture consists of an encoding and decoding architecture. The encoder takes an input sequence of data and outputs a high dimensional embedding, while the decoder takes the high dimensional embedding as an input and tries to predict the original or similar sequence to the one input into the encoder. The present disclosure does not need to predict a sequential output, so it only uses the encoding portion of the Transformer to predict polymer properties, both physical and in-vitro/in-vivo.

In yet another aspect, an illustrative embodiment of the present disclosure allows for the selection the top candidates for PNP-mediated delivery of the SOD1-targeting CBE in a mouse model of ALS. Functional gene editing tests in a microglial cell line stably expressing EGFP or SOD1 can then be performed using these top candidates. Moreover, the efficacy and safety PNP-mediated CBE delivery can be assessed in the G93A-SOD1 mouse model of ALS. Prior success of CBE base editors for slowing ALS progression in mice shows a likelihood that they can also lead to clinical translation of a novel ALS gene editing therapy.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

EXAMPLES

Example 1

Barcode Design

The nucleic acid constructs used in this example comprised a unique portion comprising 8-10 nucleotides in the center of the polynucleotide, the unique portion further constrained by the requirement of a hamming distance of at least 3 bases from any other barcodes to be pooled. Directly on the 3' end of the barcode, 7-10 random bases are included for bioinformatic removal of PCR duplicates. This central sequence is flanked by universal primer annealing sites containing overhangs for the addition of index adapters during sequencing library preparation. FIG. 4 shows a representative illustration of these barcodes. These nucleic acid constructs were designed with either a biotin functional group or an amine functional group on the 5' end.

Example 2

Polymer Nanoparticle Synthesis

A diblock copolymer was synthesized as described in PCTapp349529(21477779.1) using reversible addition-fragmentation chain transfer (RAFT) polymerization with reagents and amounts listed in Table 2. Block 1 reagents were combined in a round bottom flask, purged with argon, and heated to 60° C. for 6 hours using a heating mantle. The reaction product was purified using four 80:20 pentane:ether precipitation washes and centrifugation cycles and dried in vacuo. The Block 1 product was used as the macroRAFT agent for Block 2, and the calculated reagent volumes (as calculated based on theoretical molecular weight information for Block 1) were combined in a round bottom for the Block 2 reaction. The reaction mixture was argon purged before being heated at 60° C. for 24 hours. The reaction product was purified using the same purification process and dried in vacuo. The resulting polymer was dialyzed in deionized water for 4 days with multiple water changes each day. Finally, the dialyzed material was lyophilized for 4 days and stored at room temperature for experimental use.

TABLE 2

Reagents and amounts used to synthesize barcoded PNPs

| Reagent | Purpose | Lot 0001 Amount | Lot 0002 Amount |
| --- | --- | --- | --- |
| Block 1 | | | |
| 2-dimethylaminoethyl acrylate (DMAEMA) | Monomer | 15999.6 mg | 32000.0 mg |
| (4-cyano-4-(((ethylthio)carbonothioyl)thio)pentanoicacid) agent (ECT) | Chain transfer | 76.9 mg | 153.7 mg |
| Azobisisobutyronitrile (AIBN) | Initiator | 9.5 mg | 19.05 mg |
| Dimethylformamide (DMF) | Solvent | 24131.1 mg | 48229.8 mg |
| Block 1 Reaction Yield | % Yield | 31.75% | 39.55% |
| Block 2 | | | |
| 2-dimethylaminoethyl acrylate (DMAEMA) | Monomer | 713.0 mg | 2110.6 mg |
| butyl methacrylate (BMA) | Monomer | 1934.4 mg | 5727.6 mg |
| propyl acrylic acid (PAA) | Monomer | 518.2 mg | 1540.1 mg |
| Block 1 macroRAFT agent, meaning ECT + DMAEMA. The ECT end groups (R & Z) were still present to perform their function, but they were on the end of the p(DMAEMA) polymer synthesized as block 1. For reference, here is ECT R & Z groups oneither side of onyl group. | Macro Chain transfer agent | 1528.4 mg | 4526.2 mg |

TABLE 2-continued

Reagents and amounts used to synthesize barcoded PNPs

| Reagent | Purpose | Lot 0001 Amount | Lot 0002 Amount |
|---|---|---|---|
| ECT (structure shown: Z = ethyl trithiocarbonate group; R = -C(CH₃)(CN)-CH₂CH₂-COOH) | | | |
| Azobisisobutyronitrile (AIBN) | Initiator | 1.7 mg | 4.93 mg |
| Dimethylformamide (DMF) | Solvent | 7045.0 mg | 20828.8 mg |
| Block 2 Reaction Yield | % Yield | 73.33% | 70.99% |

Example 3

Figure 6:
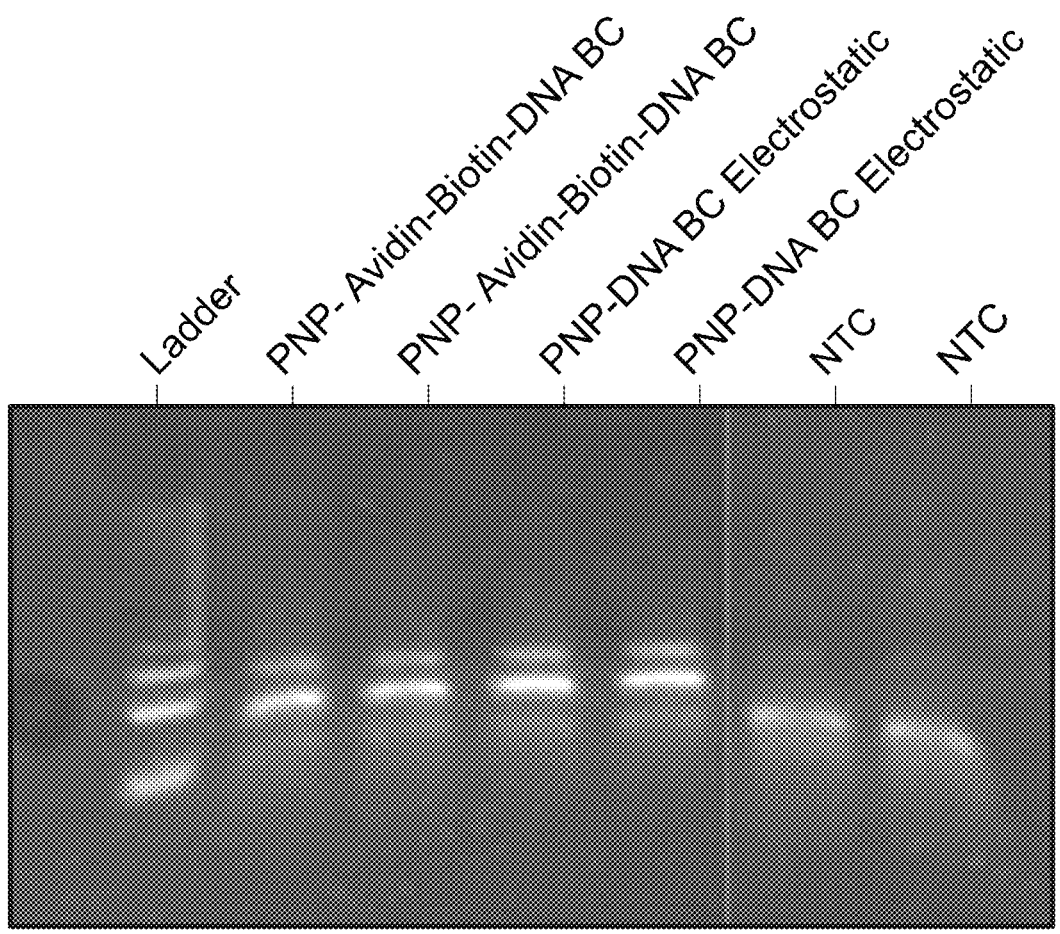
FIG. 6 is an e-gel showing amplification of nucleic acid constructs electrostatically bound to polymer nanoparticles. The presence of the double band in the samples with nucleic acid construct confirms that the barcodes were attached to the PNP. The absence of the double band in the not test control (NTC) validates the positive result.

Composition Example 1 (CE1): Electrostatic Attachment of Nucleic Acid Constructs (Containing DNA Barcodes) to Polymer Nanoparticles RAFT copolymers were synthesized according to the methods above and the reagents listed in Table 2. The polymer was dispersed in phosphate buffered saline at a concentration of ~5 mg/ml. For electrostatic loading (FIG. 5a), nucleic acid constructs (according to the design shown in FIG. 4 including polynucleotide barcodes) were dissolved in tris EDTA buffer at a concentration of ~100 µM (~1.9 mg/mL). These stock solutions were mixed together with PBS to produce a solution with a final concentration of 0.05 mg/mL polymer and 0.00389 mg/mL nucleic acid construct. They were incubated at room temperature for at least 30 minutes to allow the positively charged polymer to associate with the negatively charged nucleic acid constructs. The sample was transferred to an amicon ultra-4 centrifuge tube (MWCO 30 kDa). (Max 3.5 mL/Tube) and centrifuged at 4,000× g for 15 minutes to remove any unbound nucleic acid constructs. The filtrate (containing unbound nucleic acid constructs) was discarded and sterile PBS was added to the retentate to final concentration of 0.05 mg/mL polymer and 0.00389 mg/mL nucleic acid constructs. The electrostatically bound nucleic acid constructs were amplified via PCR, using primers designed to bind to the universal primer binding segments on the nucleic acid constructs. The amplicons were detected via gel electrophoresis on agarose gel. The presence of a double band (FIG. 6) in a lane indicates the presence of amplicons, showing that nucleic acid constructs were bound to the PNPs.

Example 4

Figure 7:
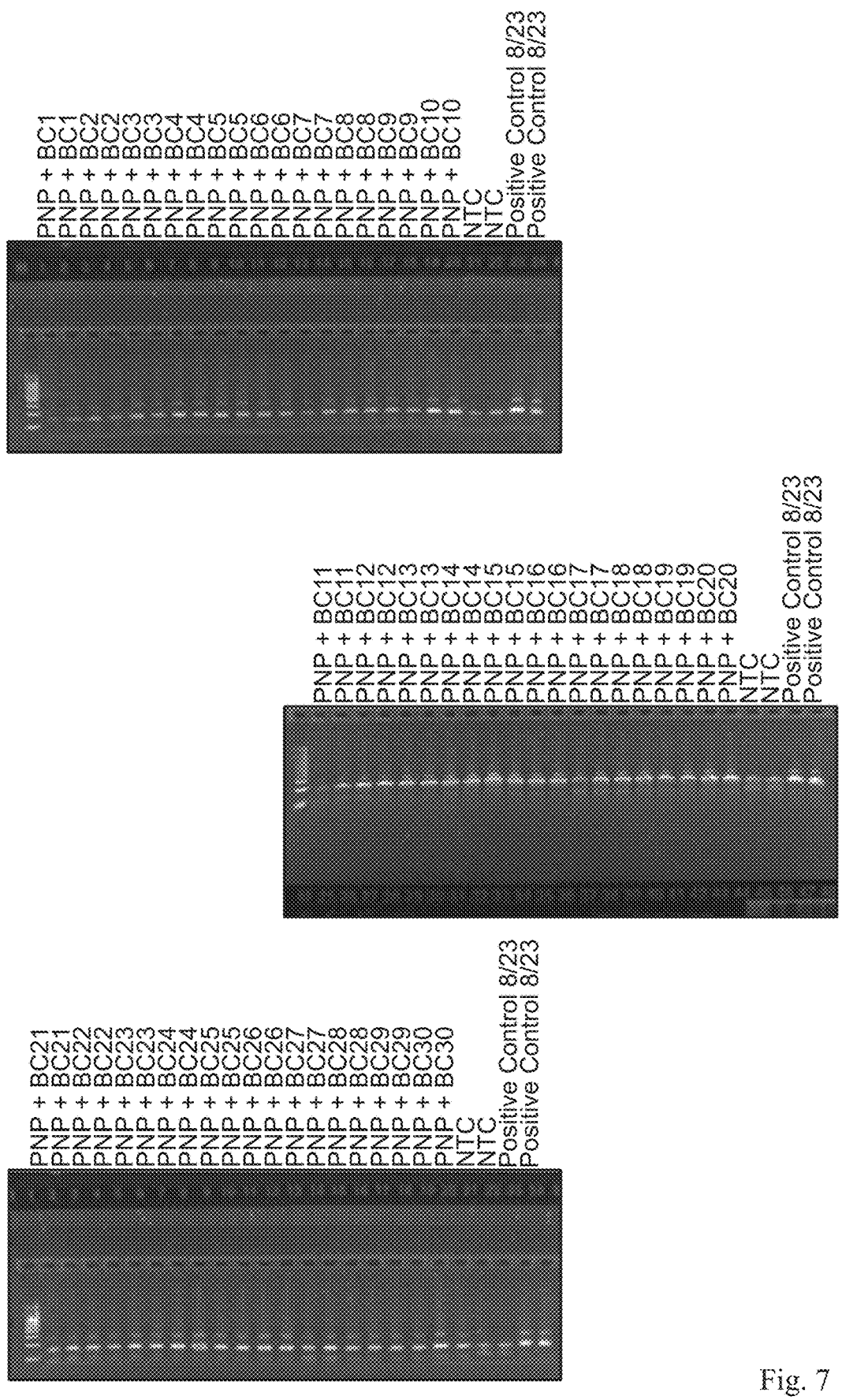
FIG. 7 is a series of e-gels showing DNA barcode amplification from a pooled sample of 96 unique barcodes, each attached to a prototype PNP. Each frame in the figure is one row of a 48 channel gel electrophoresis. The first column of each gel is a DNA latter, the bottom band of which is ~100 bases. The bright band in each column near the 100 bp mark indicates amplicons coming from the barcodes.
Figure 7:
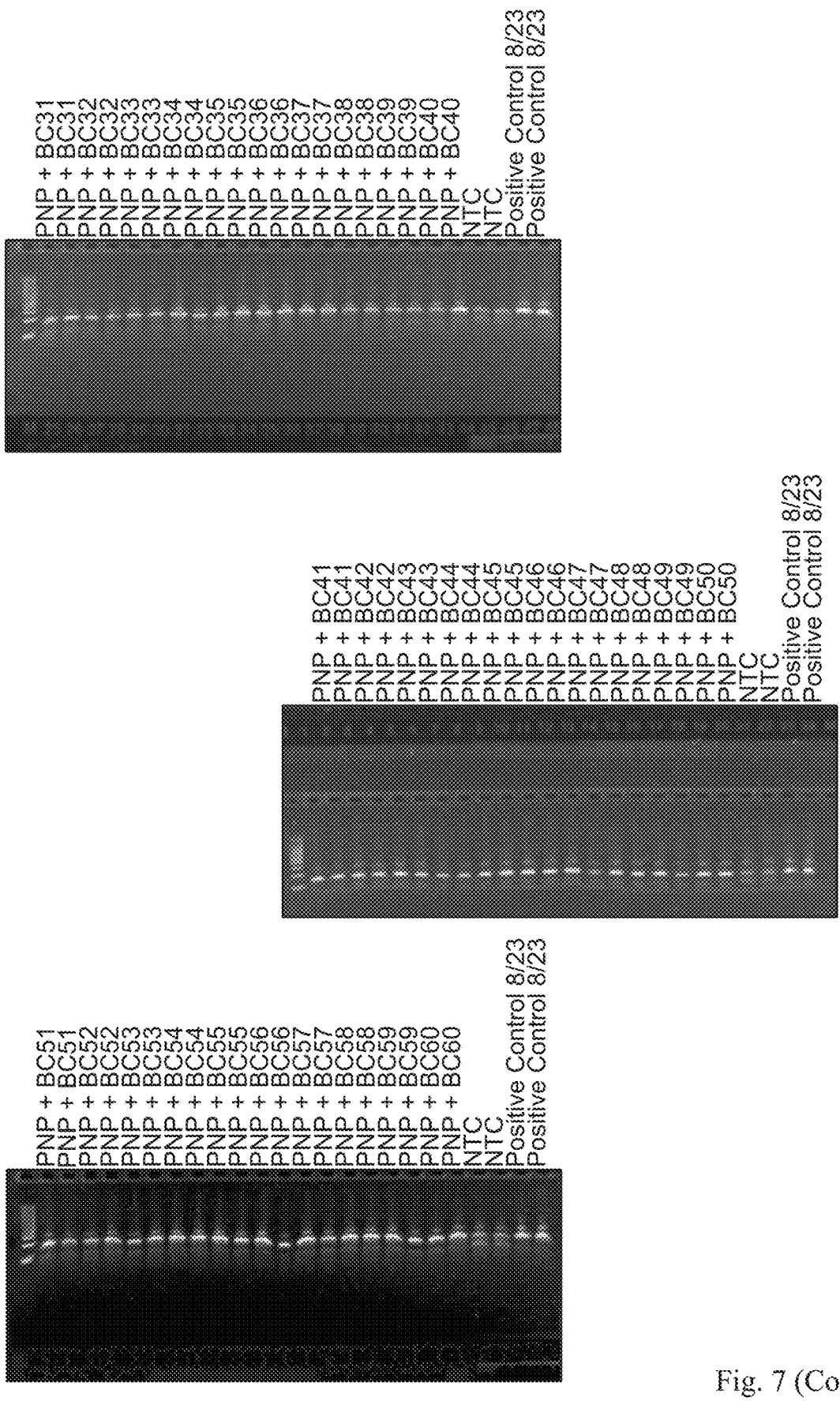
Figure 7:
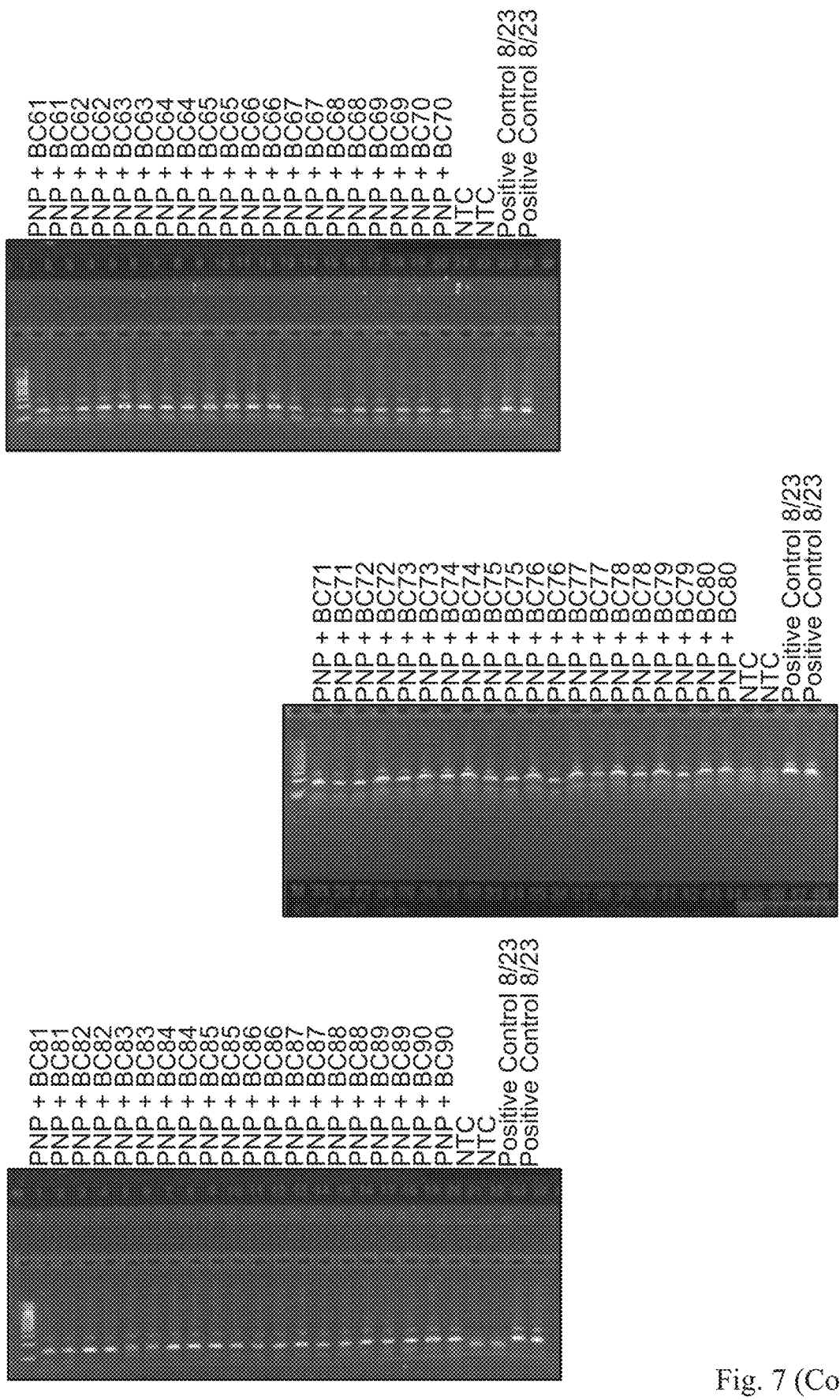
Figure 7:
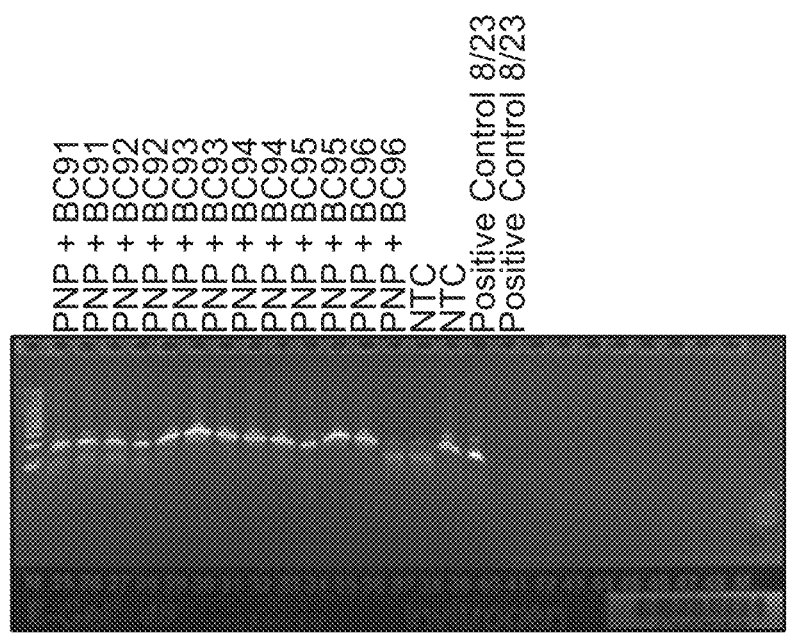

Composition Example 2 (CE2): Nucleic Acid Construct Conjugation to PNPs Via Avidin-Biotin Linkage RAFT copolymers made using CTAs that contain at least one carboxyl terminal group were further functionalized with avidin (FIG. 5b). A RAFT copolymer was transferred into a MES buffer at ~12 mg/mL. The sample was sonicated for 30 minutes. EDC reagent and Sulfo-NHS reagent was added to the polymer at a molar ratio of 10:1 and 25:1 respectively, reagent to PNP. The sample was incubated for at least 10 minutes at room temperature to allow the reaction to occur. The reaction volume was filtered through a membrane with a molecular weight cut off of 30 kDa via centrifuge at ~3000× g for ~15 minutes. The filtrate was discarded, and sterile PBS was added to the retentate to reconstitute to 10 mg/mL polymer. Avidin (36.9 mg) was added to the reaction and incubated for 15 minutes at room temperature. The sample was transferred to an amicon ultra-4 centrifuge tube (MWCO 30 kDa). (Max 3.5 mL/Tube) and centrifuged at 4,000× g for 15 minutes. The filtrate was discarded and sterile PBS was added to the retentate to final concentration of 8 mg/mL polymer. A nucleic acid constructs with biotin attached to the 5' end was added to the avidin functionalized polymer at a molar ratio of 10 moles of polymer to 1 mole of nucleic acid constructs. The sample was incubated for at least 15 minutes. The sample was transferred to an amicon ultra-4 centrifuge tube (MWCO 30 kDa, Max 3.5 mL/Tube) and centrifuged at 4,000× g for 15 minutes to remove any unbound nucleic acid constructs. The filtrate (containing unbound nucleic acid constructs) was discarded and sterile PBS was added to the retentate to final concentration of 8 mg/mL polymer. The conjugated nucleic acid constructs were amplified via PCR, using primers designed to bind to the universal primer binding segments on the nucleic acid constructs. The amplicons were detected via gel electrophoresis on agarose gel. The presence of a double band (FIGS. 6 and 7) in a lane indicates the presence of amplicons, showing that nucleic acid constructs were bound to the PNPs.

Figure 13:
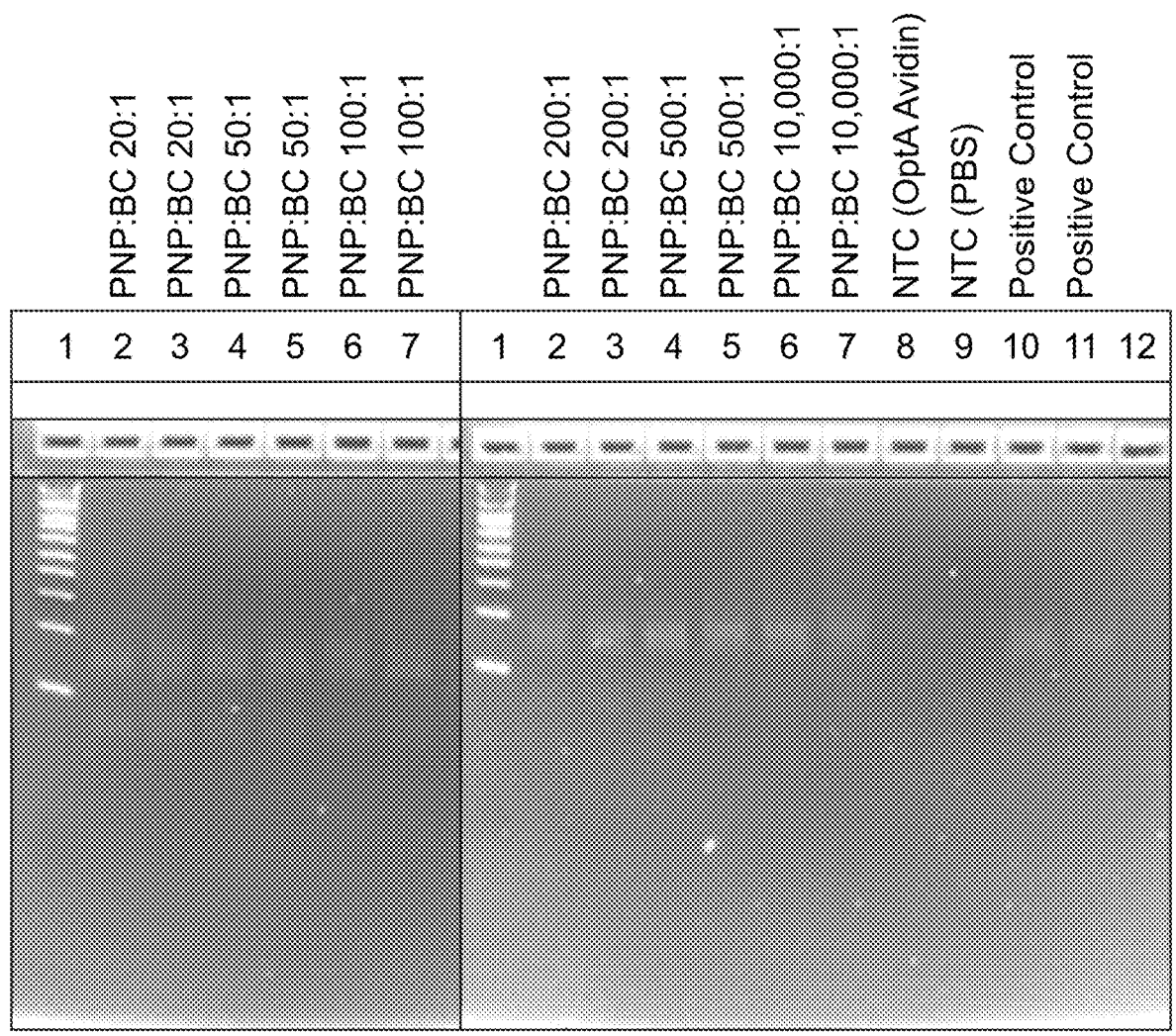
FIG. 13 is an electrophoresis gel showing a band corresponding to barcode (BC) amplicons produced from PCR performed on samples of PNPs with barcodes attached at various molar ratios of PNP to BC (i.e. moles of polymer divided by moles of barcode). The presence of the band for all barcoded PNP samples confirms that the barcode can be detected via PCR on PNPs labeled with barcodes at ratios of anywhere from 20:1 to 10,000:1 (moles PNP:moles BC).

To test the range of PNP to barcode ratios that can be used in the reduction to practice of nucleic acid constructs labeled PNPs, the method above was used to attach the nucleic acid constructs to PNPs using the avidin-biotin linkage (FIG. 5a), varying the PNP to nucleic acid constructs ratio from as low as 20:1 to as high as 10,000 to 1 (moles polymer to moles nucleic acid constructs). FIG. 13 shows a gel electrophoresis graph with bands corresponding to the amplicons from nucleic acid constructs produced from a PCR reaction on the nucleic acid constructs with these various PNP to nucleic acid constructs ratios, indicating that these ratios are in the useable range for the reduction to practice of the nucleic acid constructs PNP composition.

The avidin-biotin conjugation method was used to attach 96 unique barcodes to 96 aliquots of the polymer described in Table 2, yielding 96 aliquots of the same polymer in which the population of nanoparticles in each aliquot has a unique barcode attached. These 96 aliquots were pooled by combining the aliquots in volumetrically equivalent amounts into a single vial, yielding a dispersion of 96 distinct populations of barcoded PNPs, in which all populations comprised a polymer micelle formed from the polymer described in Table 2 and a unique barcode from the population of 96 unique barcodes.

Figure 8:
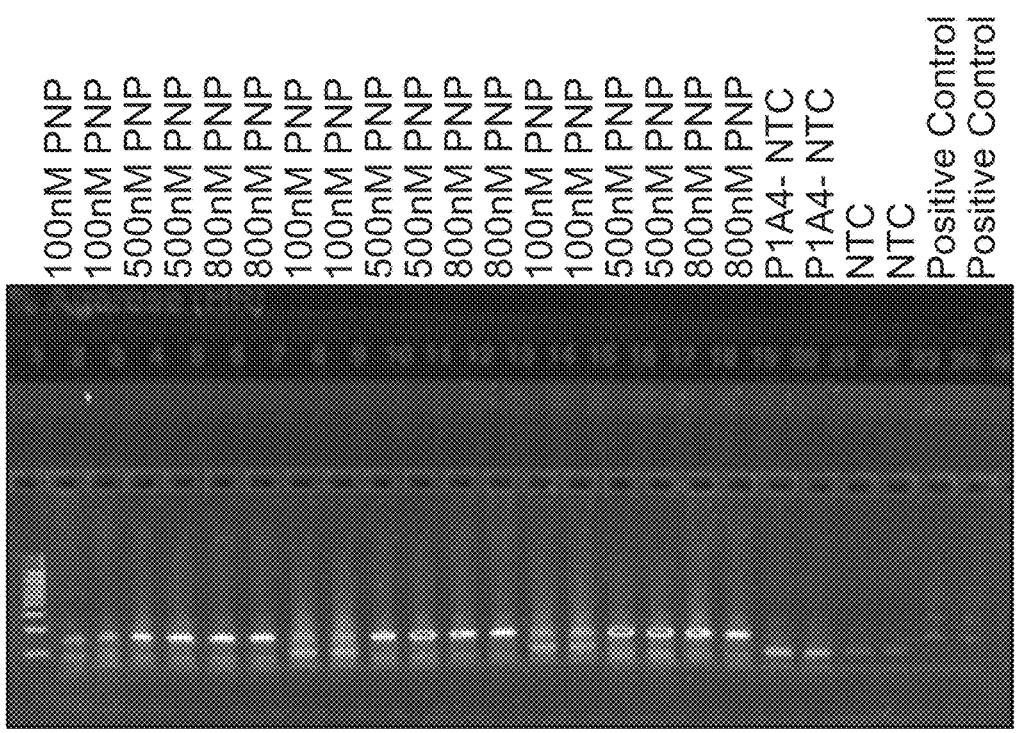
FIG. 8. is an e-gel showing DNA barcode amplification from a pooled sample of 96 unique barcodes, attached to a prototype PNP, extracted after being spiked into a culture of HEK-293 cells. Each frame in the figure is one row of a 48 channel gel electrophoresis. The first column of each gel is a D=NA latter, the bottom band of which is ~100 bases. The bright band in each column near the 100 bp mark indicates amplicons coming from the barcodes.

The pooled sample of avidin-biotin conjugated nucleic acid construct-PNPs were spiked into HEK-293T cells. The cells were seeded in 96 well plates at 20,000 cells per well, in 100 µL of media and left to adhere overnight. Twenty-four hours after seeding, the pooled sample of PNPs with 96 unique barcodes were added at a dose of ~0.024 mg/mL PNP in each well and placed in an incubator at 37° C. overnight. The next day, barcodes extracted from the samples, using the QIAamp 96 DNA extraction kit and a Qiacube HT instrument according to the manufacturer's protocol. The conjugated barcodes were amplified via PCR, using primers designed to bind to the universal primer binding sequences on the barcodes. The amplicons were detected via gel electrophoresis on agarose gel. The presence of a double band (FIG. 8) in a lane indicates the presence of amplicons, showing that nucleic acid constructs were bound to the PNPs.

Figure 12A:
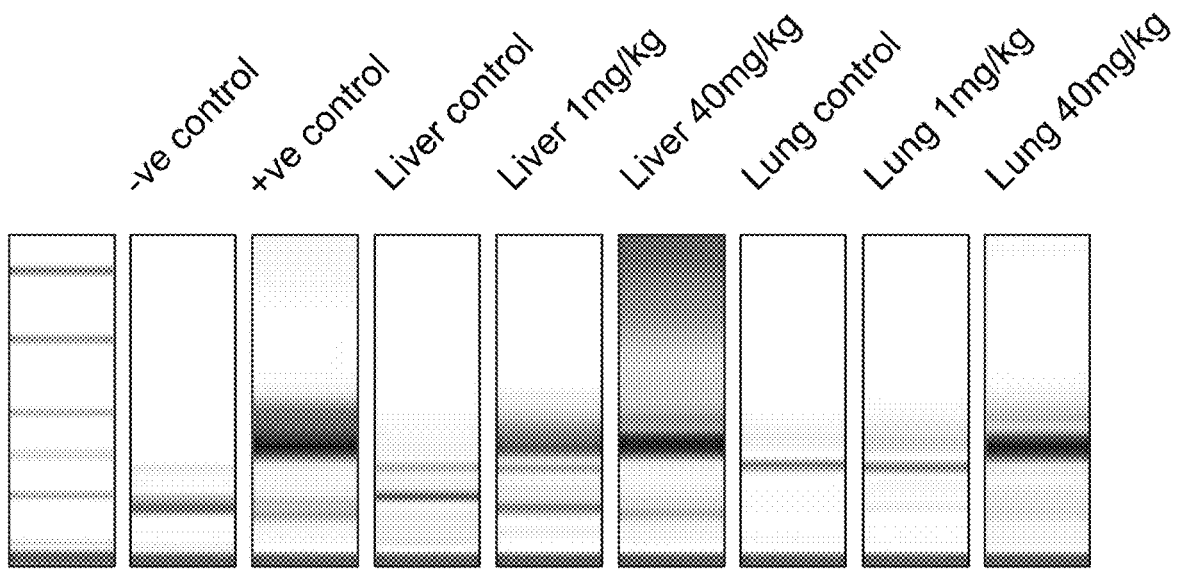
FIGS. 12(a)-12(d) show gel images of PCR amplified barcodes extracted from indicated mouse tissues (FIGS. 12(a) and 12(b)); sequencing data demonstrating the ability to detect all 96 individual barcodes from a single mouse organ, where (a) denotes low dose and (b) denotes high dose (FIG. 12(c)); and a graph depicting relative abundance of each barcode in a single organ (FIG. 12(d)).
Figure 12B:
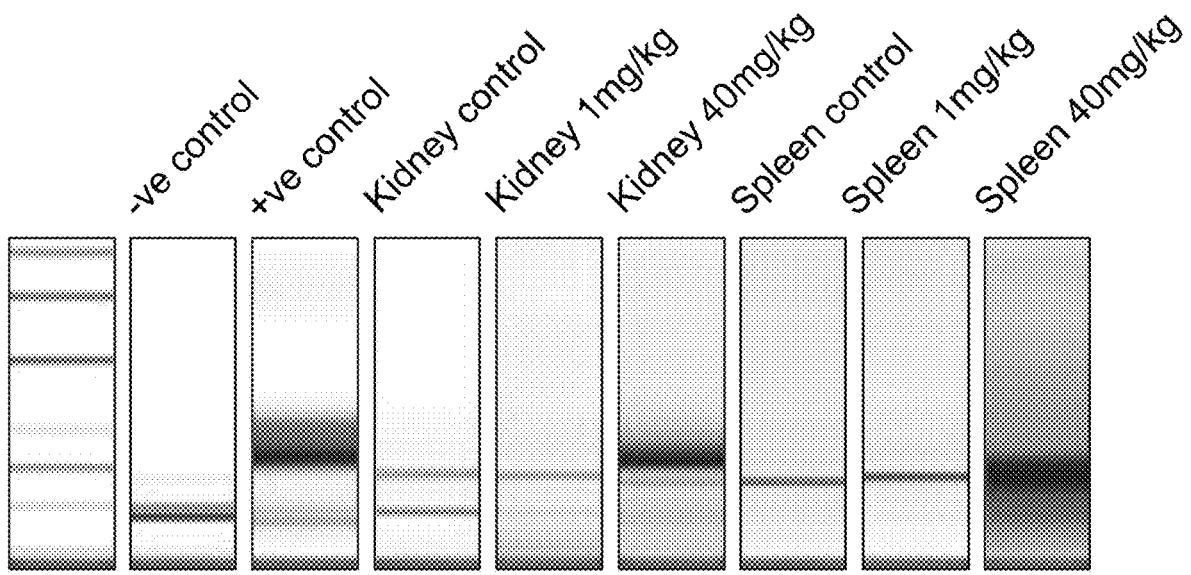
Figure 12C:
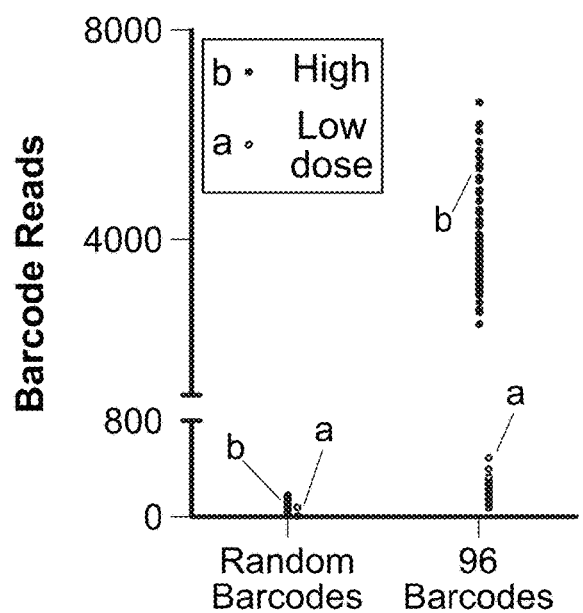
Figure 12D:
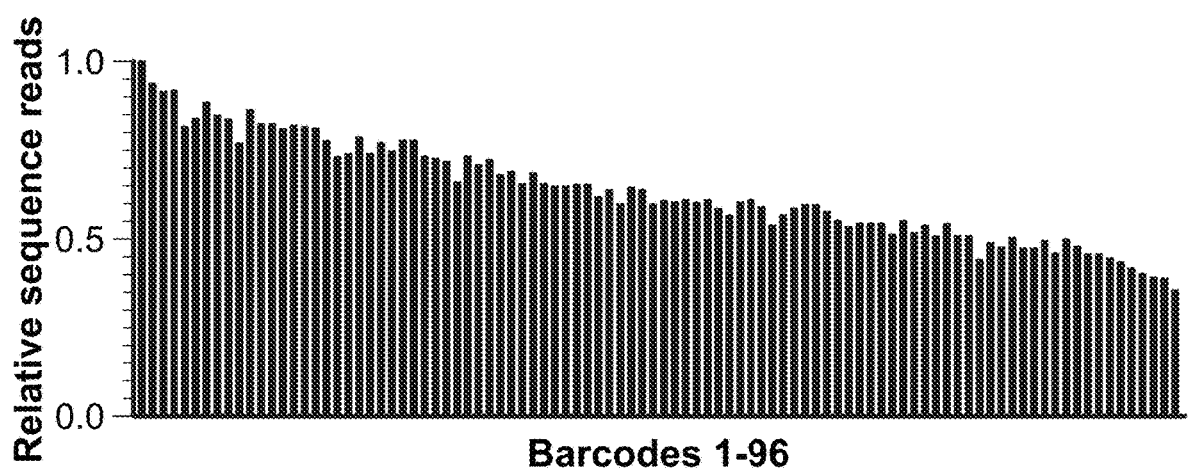

The pooled sample of PNPs with 96 unique barcodes conjugated via avidin-biotin linkage, was administered to mice (using the in vivo screening protocol described below). Twenty-four hours after dosing, the mice were sacrificed and the tissues were analyzed for the presence of the barcoded PNPs. PCR was used to amplify the barcodes from the tissue samples and agilent fragment analysis was used to detect the presence of nucleic acid constructs-PNPs, with a dark band matching the positive control as the indicator of the presence of nucleic acid constructs-PNPs (FIG. 12a). This experiment reduced to practice the ability to label PNPs with unique nucleic acid constructs, administer them to mice, and then detect their biodistribution via PCR. We further used deep sequencing techniques to distinguish all 96 unique barcodes in the liver tissue. Library preparations, sequencing and sequence analysis were performed as described below. All 96 unique barcodes were detected in a way that was countable and distinguishable from the others (FIG. 12c and FIG. 12d). This shows that our compositions allow not only the detection of uniquely barcoded PNPs in mouse tissue 24 hours after dosing, but it also allows us to quantitatively distinguish each uniquely barcoded PNP from all other uniquely barcoded PNPs in the animal tissue.

Example 5

Preparation of RAFT Copolymers for Polymer Nanoparticle Libraries

Briefly, Block 1 reagents (monomer(s), chain transfer agent, initiator, and solvent) were combined in wells of a polypropylene 96-well u-shaped bottom microplate (Greiner Bio-One), in polypropylene 96 well cluster tubes (Corning), in polypropylene Eppendorf microcentrifuge tubes (Sigma-Aldrich), or in polypropylene 50 mL or 15 mL conical tubes (VWR) and placed in a VWR 1400E Sheldon vacuum oven. A 20 mL glass vial was filled with approximately 10-15 mL of solvent (e.g., dimethylformamide), and the vial was placed in the oven to provide a source for atmosphere saturation. The oven was purged with argon at ~3 L/min for approximately 45 minutes and heated to between 60° C. and 75° C. for 6-24 hours. Upon completion of the reaction, acetone was added to the wells or tubes to prevent polymer solidification and the wells or tubes were sealed and left at room temperature overnight. The next day, the reaction product solutions were transferred to 1.5 mL Eppendorf tubes (if necessary) and purified via at least three precipitation washes using an appropriate purification solvent solution (e.g., 80:20 pentane:ether, isopropyl alcohol, methanol, etc.) and centrifugation cycles and dried in vacuo. The Block 1 product was used as the macroRAFT agent for Block 2, and the calculated reagent volumes (as calculated based on theoretical or actual molecular weight information for Block 1) were combined in a polypropylene 96-well u-shaped bottom microplate (Greiner Bio-One), in polypropylene 96 well cluster tubes (Corning), in polypropylene Eppendorf microcentrifuge tubes (Sigma-Aldrich), or in polypropylene 50 mL or 15 mL conical tubes (VWR) for the Block 2 reaction. The reaction mixtures were placed in a VWR 1400E Sheldon vacuum oven, which was argon purged at ~3 L/min for approximately 45 minutes before being heated to between 60° C. and 75° C. for 6-24 hours. The reaction products were purified using the same purification process as used for Block 1 library materials and dried in vacuo. The resulting polymers were resuspended in either acetone or chloroform and aliquoted as needed for experimental use (these transfer solvents evaporated prior to material use), stored in a dry state at room temperature, or dissolved in deionized water, frozen, and lyophilized prior to experimental use. Size was measured using a Wyatt Technology DynaPro Plate Reader III. Molecular weights for Block 1 materials were measured using a DynaPro Plate Reader III. Nanoparticle sizes above the DynaPro Plate Reader III molar mass capability threshold prevented measurement of Block 2 molecular weights for these polymer libraries. All molecular weights for high-throughput polymer libraries are reported as weight average molecular weight ($M_w$).

A summary of the reagents, amounts, and reaction conditions used to synthesize Block 1 and Block 2 of a pilot PNP library of 96 PNPs are shown in Tables 3 and 4, respectively, below. PNPs 22, 61, and 89-96 were used as 10 unique PNPs for HEK cell studies. PNPs 1-88 were used as unique PNPs for flow cytometry studies. Table 3 Abbreviations: ACVA, 4,4'-Azobis(4-cyanovaleric acid); AIBN, Azobisisobutyronitrile; BMA, butyl methacrylate; CTP, 4-Cyano-4-(thiobenzoylthio)pentanoic acid; DMAEMA, dimethylaminoethyl methacrylate; DMF, N,N-Dimethylformamide; ECT, 4-Cyano-4-[(ethylsulfanylthiocarbonyl)sulfanyl]pentanoic acid; MMA, methyl methacrylate. Table 4 Abbreviations: ACVA, 4,4'-Azobis(4-cyanovaleric acid); AIBN, Azobisisobutyronitrile; BMA, butyl methacrylate; CTP, 4-Cyano-4-(thiobenzoylthio)pentanoic acid; DMAEMA, dimethylaminoethyl methacrylate; DMF, N,N-Dimethylformamide; ECT, 4-Cyano-4-[(ethylsulfanylthiocarbonyl)sulfanyl]pentanoic acid; HEMA, 2-Hydroxyethyl methacrylate; MMA, methyl methacrylate. Table 5 Abbreviations: PDI, polydispersity index.

Static Light Scattering (SLS) and Dynamic Light Scattering (DLS) measurements to determine Block 1 molar mass and PNP size (e.g., diameter) were determined using a DynaPro Plate Reader III by Wyatt Technology. Data acquisition and handling were made with DYNAMICS software. SLS and DLS data were obtained under the following conditions:
  SOLVENT: Water
  TEMPERATURE: 25° C.
  SAMPLE VOLUME: 200 µL
  DATA ACQUISITION SETTINGS: 5 acquisitions of 5 seconds per acquisition

TABLE 3

Summary of Block 1 Reagents and Reaction Conditions Used in Pilot PNP Library

Block 1 Reagents, Purpose, Amounts, and Reaction Conditions

| PNP | Monomer and Amount (mol) | | Chain Transfer Agent (CTA) and Amount (mol) | | Initiator and Amount (mol) | | Solvent Amount (mol) | | Time (min) | Temp (C.) | Block 1 Rxn % Yield |
|---|---|---|---|---|---|---|---|---|---|---|---|
| 1  | DMAE MA | 2.49E-04 | CTP | 2.49E-06 | ACVA | 2.49E-06 | DMF | 2.04E-03 | 363 | 75 | 56.4 |
| 2  | DMAE MA | 2.49E-04 | CTP | 1.09E-06 | ACVA | 1.09E-06 | DMF | 2.04E-03 | 363 | 75 | 62.1 |
| 3  | DMAE MA | 2.49E-04 | CTP | 8.54E-07 | ACVA | 8.55E-07 | DMF | 2.04E-03 | 363 | 75 | 59.2 |
| 4  | DMAE MA | 2.49E-04 | CTP | 7.00E-07 | ACVA | 7.01E-07 | DMF | 2.04E-03 | 363 | 75 | 57.9 |
| 5  | DMAE MA | 2.49E-04 | CTP | 5.18E-07 | ACVA | 5.16E-07 | DMF | 2.04E-03 | 363 | 75 | 66.7 |
| 6  | DMAE MA | 2.49E-04 | CTP | 4.61E-07 | ACVA | 4.57E-07 | DMF | 2.04E-03 | 363 | 75 | 66.6 |
| 7  | DMAE MA | 2.49E-04 | CTP | 4.13E-07 | ACVA | 4.08E-07 | DMF | 2.04E-03 | 363 | 75 | 61.5 |
| 8  | DMAE MA | 2.49E-04 | CTP | 3.65E-07 | ACVA | 3.68E-07 | DMF | 2.04E-03 | 363 | 75 | 50.6 |
| 9  | DMAE MA | 2.49E-04 | CTP | 3.36E-07 | ACVA | 3.37E-07 | DMF | 2.04E-03 | 363 | 75 | 57.2 |
| 10 | DMAE MA | 2.49E-04 | CTP | 3.07E-07 | ACVA | 3.12E-07 | DMF | 2.04E-03 | 363 | 75 | 56.7 |
| 11 | DMAE MA | 2.49E-04 | CTP | 1.52E-06 | ACVA | 1.52E-06 | DMF | 2.04E-03 | 363 | 75 | 74.3 |
| 12 | DMAE MA | 2.49E-04 | CTP | 1.09E-06 | ACVA | 1.09E-06 | DMF | 2.04E-03 | 363 | 75 | 73.0 |
| 13 | DMAE MA | 2.49E-04 | CTP | 8.54E-07 | ACVA | 8.55E-07 | DMF | 2.04E-03 | 363 | 75 | 68.1 |
| 14 | DMAE MA | 2.49E-04 | CTP | 7.00E-07 | ACVA | 7.01E-07 | DMF | 2.04E-03 | 363 | 75 | 64.6 |
| 15 | DMAE MA | 2.49E-04 | CTP | 5.18E-07 | ACVA | 5.16E-07 | DMF | 2.04E-03 | 363 | 75 | 69.5 |
| 16 | DMAE MA | 2.49E-04 | CTP | 4.61E-07 | ACVA | 4.57E-07 | DMF | 2.04E-03 | 363 | 75 | 57.0 |
| 17 | DMAE MA | 2.49E-04 | CTP | 4.13E-07 | ACVA | 4.08E-07 | DMF | 2.04E-03 | 363 | 75 | 53.4 |
| 18 | DMAE MA | 2.49E-04 | CTP | 3.65E-07 | ACVA | 3.68E-07 | DMF | 2.04E-03 | 363 | 75 | 66.4 |
| 19 | DMAE MA | 2.49E-04 | CTP | 3.36E-07 | ACVA | 3.37E-07 | DMF | 2.04E-03 | 363 | 75 | 55.0 |
| 20 | DMAE MA | 2.49E-04 | CTP | 2.49E-06 | ACVA | 2.49E-06 | DMF | 2.04E-03 | 363 | 75 | 66.6 |
| 21 | DMAE MA | 2.49E-04 | CTP | 1.52E-06 | ACVA | 1.52E-06 | DMF | 2.04E-03 | 363 | 75 | 75.4 |
| 22 | DMAE MA | 2.49E-04 | CTP | 1.09E-06 | ACVA | 1.09E-06 | DMF | 2.04E-03 | 363 | 75 | 73.6 |
| 23 | DMAE MA | 2.49E-04 | CTP | 8.54E-07 | ACVA | 8.55E-07 | DMF | 2.04E-03 | 363 | 75 | 65.1 |
| 24 | DMAE MA | 2.49E-04 | CTP | 7.00E-07 | ACVA | 7.01E-07 | DMF | 2.04E-03 | 363 | 75 | 71.4 |
| 25 | DMAE MA | 2.49E-04 | CTP | 5.95E-07 | ACVA | 5.94E-07 | DMF | 2.04E-03 | 363 | 75 | 60.7 |
| 26 | DMAE MA | 2.49E-04 | CTP | 5.18E-07 | ACVA | 5.16E-07 | DMF | 2.04E-03 | 363 | 75 | 66.6 |
| 27 | DMAE MA | 2.49E-04 | CTP | 4.61E-07 | ACVA | 4.57E-07 | DMF | 2.04E-03 | 363 | 75 | 55.2 |
| 28 | DMAE MA | 2.49E-04 | CTP | 4.13E-07 | ACVA | 4.08E-07 | DMF | 2.04E-03 | 363 | 75 | 55.7 |
| 29 | DMAE MA | 2.49E-04 | CTP | 3.65E-07 | ACVA | 3.68E-07 | DMF | 2.04E-03 | 363 | 75 | 51.4 |
| 30 | DMAE MA | 2.49E-04 | CTP | 3.36E-07 | ACVA | 3.37E-07 | DMF | 2.04E-03 | 363 | 75 | 53.3 |
| 31 | DMAE MA | 2.49E-04 | CTP | 3.07E-07 | ACVA | 3.12E-07 | DMF | 2.04E-03 | 363 | 75 | 47.2 |
| 32 | DMAE MA | 2.49E-04 | CTP | 1.52E-06 | ACVA | 1.52E-06 | DMF | 2.04E-03 | 363 | 75 | 88.7 |
| 33 | DMAE MA | 2.49E-04 | CTP | 1.09E-06 | ACVA | 1.09E-06 | DMF | 2.04E-03 | 363 | 75 | 72.0 |
| 34 | DMAE MA | 2.49E-04 | CTP | 8.54E-07 | ACVA | 8.55E-07 | DMF | 2.04E-03 | 363 | 75 | 65.0 |
| 35 | DMAE MA | 2.49E-04 | CTP | 5.95E-07 | ACVA | 5.94E-07 | DMF | 2.04E-03 | 363 | 75 | 69.4 |

TABLE 3-continued

Summary of Block 1 Reagents and Reaction Conditions Used in Pilot PNP Library

Block 1 Reagents, Purpose, Amounts, and Reaction Conditions

| PNP | Monomer and Amount (mol) | | Chain Transfer Agent (CTA) and Amount (mol) | | Initiator and Amount (mol) | | Solvent Amount (mol) | | Time (min) | Temp (C.) | Block 1 Rxn % Yield |
|---|---|---|---|---|---|---|---|---|---|---|---|
| 36 | DMAE MA | 2.49E-04 | CTP | 4.61E-07 | ACVA | 4.57E-07 | DMF | 2.04E-03 | 363 | 75 | 46.1 |
| 37 | DMAE MA | 2.49E-04 | CTP | 4.13E-07 | ACVA | 4.08E-07 | DMF | 2.04E-03 | 363 | 75 | 47.5 |
| 38 | DMAE MA | 2.49E-04 | CTP | 3.36E-07 | ACVA | 3.37E-07 | DMF | 2.04E-03 | 363 | 75 | 52.3 |
| 39 | DMAE MA | 2.49E-04 | CTP | 3.07E-07 | ACVA | 3.12E-07 | DMF | 2.04E-03 | 363 | 75 | 55.9 |
| 40 | DMAE MA | 2.49E-04 | CTP | 2.49E-06 | ACVA | 2.49E-06 | DMF | 2.04E-03 | 363 | 75 | 82.3 |
| 41 | DMAE MA | 2.49E-04 | CTP | 8.54E-07 | ACVA | 8.55E-07 | DMF | 2.04E-03 | 363 | 75 | 76.5 |
| 42 | DMAE MA | 2.49E-04 | CTP | 7.00E-07 | ACVA | 7.01E-07 | DMF | 2.04E-03 | 363 | 75 | 71.7 |
| 43 | DMAE MA | 2.49E-04 | CTP | 4.13E-07 | ACVA | 4.08E-07 | DMF | 2.04E-03 | 363 | 75 | 54.9 |
| 44 | DMAE MA | 2.49E-04 | CTP | 3.65E-07 | ACVA | 3.68E-07 | DMF | 2.04E-03 | 363 | 75 | 54.3 |
| 45 | DMAE MA | 2.49E-04 | CTP | 3.36E-07 | ACVA | 3.37E-07 | DMF | 2.04E-03 | 363 | 75 | 54.6 |
| 46 | DMAE MA | 2.49E-04 | CTP | 3.07E-07 | ACVA | 3.12E-07 | DMF | 2.04E-03 | 363 | 75 | 55.0 |
| 47 | DMAE MA | 2.49E-04 | CTP | 1.09E-06 | ACVA | 1.09E-06 | DMF | 2.04E-03 | 363 | 75 | 93.5 |
| 48 | DMAE MA | 2.49E-04 | CTP | 8.54E-07 | ACVA | 8.55E-07 | DMF | 2.04E-03 | 363 | 75 | 79.7 |
| 49 | DMAE MA | 2.49E-04 | CTP | 5.18E-07 | ACVA | 5.16E-07 | DMF | 2.04E-03 | 363 | 75 | 56.9 |
| 50 | DMAE MA | 2.49E-04 | CTP | 4.61E-07 | ACVA | 4.57E-07 | DMF | 2.04E-03 | 363 | 75 | 52.0 |
| 51 | DMAE MA | 2.49E-04 | CTP | 4.13E-07 | ACVA | 4.08E-07 | DMF | 2.04E-03 | 363 | 75 | 55.8 |
| 52 | DMAE MA | 2.49E-04 | CTP | 3.36E-07 | ACVA | 3.37E-07 | DMF | 2.04E-03 | 363 | 75 | 51.8 |
| 53 | DMAE MA | 2.49E-04 | CTP | 3.07E-07 | ACVA | 3.12E-07 | DMF | 2.04E-03 | 363 | 75 | 53.1 |
| 54 | DMAE MA | 2.49E-04 | CTP | 1.52E-06 | ACVA | 1.52E-06 | DMF | 2.04E-03 | 363 | 75 | 86.5 |
| 55 | DMAE MA | 2.49E-04 | CTP | 8.54E-07 | ACVA | 8.55E-07 | DMF | 2.04E-03 | 363 | 75 | 72.9 |
| 56 | DMAE MA | 2.49E-04 | CTP | 7.00E-07 | ACVA | 7.01E-07 | DMF | 2.04E-03 | 363 | 75 | 71.5 |
| 57 | DMAE MA | 2.49E-04 | CTP | 5.95E-07 | ACVA | 5.94E-07 | DMF | 2.04E-03 | 363 | 75 | 59.9 |
| 58 | DMAE MA | 2.49E-04 | CTP | 5.18E-07 | ACVA | 5.16E-07 | DMF | 2.04E-03 | 363 | 75 | 63.7 |
| 59 | DMAE MA | 2.49E-04 | CTP | 4.13E-07 | ACVA | 4.08E-07 | DMF | 2.04E-03 | 363 | 75 | 52.0 |
| 60 | DMAE MA | 2.49E-04 | CTP | 3.65E-07 | ACVA | 3.68E-07 | DMF | 2.04E-03 | 363 | 75 | 54.9 |
| 61 | DMAE MA | 2.49E-04 | CTP | 3.36E-07 | ACVA | 3.37E-07 | DMF | 2.04E-03 | 363 | 75 | 55.3 |
| 62 | DMAE MA | 2.49E-04 | CTP | 3.07E-07 | ACVA | 3.12E-07 | DMF | 2.04E-03 | 363 | 75 | 42.2 |
| 63 | DMAE MA | 2.49E-04 | CTP | 1.52E-06 | ACVA | 1.52E-06 | DMF | 2.04E-03 | 363 | 75 | 82.9 |
| 64 | DMAE MA | 2.49E-04 | CTP | 1.09E-06 | ACVA | 1.09E-06 | DMF | 2.04E-03 | 363 | 75 | 71.2 |
| 65 | DMAE MA | 2.49E-04 | CTP | 5.95E-07 | ACVA | 5.94E-07 | DMF | 2.04E-03 | 363 | 75 | 60.4 |
| 66 | DMAE MA | 2.49E-04 | CTP | 5.18E-07 | ACVA | 5.16E-07 | DMF | 2.04E-03 | 363 | 75 | 64.9 |
| 67 | DMAE MA | 2.49E-04 | CTP | 3.65E-07 | ACVA | 3.68E-07 | DMF | 2.04E-03 | 363 | 75 | 54.0 |
| 68 | DMAE MA | 2.49E-04 | CTP | 3.36E-07 | ACVA | 3.37E-07 | DMF | 2.04E-03 | 363 | 75 | 44.2 |
| 69 | DMAE MA | 2.49E-04 | CTP | 3.07E-07 | ACVA | 3.12E-07 | DMF | 2.04E-03 | 363 | 75 | 52.4 |
| 70 | DMAE MA | 2.49E-04 | CTP | 2.49E-06 | ACVA | 4.97E-07 | DMF | 2.04E-03 | 363 | 75 | 52.5 |

TABLE 3-continued

Summary of Block 1 Reagents and Reaction Conditions Used in Pilot PNP Library

Block 1 Reagents, Purpose, Amounts, and Reaction Conditions

| PNP | Monomer and Amount (mol) | | Chain Transfer Agent (CTA) and Amount (mol) | | Initiator and Amount (mol) | | Solvent Amount (mol) | | Time (min) | Temp (C.) | Block 1 Rxn % Yield |
|---|---|---|---|---|---|---|---|---|---|---|---|
| 71 | DMAE MA | 2.49 E−04 | CTP | 1.52E−06 | ACVA | 3.03 E−07 | DMF | 2.04 E−03 | 363 | 75 | 46.6 |
| 72 | DMAE MA | 2.49 E−04 | CTP | 1.09E−06 | ACVA | 2.19 E−07 | DMF | 2.04 E−03 | 363 | 75 | 40.2 |
| 73 | DMAE MA | 2.49 E−04 | CTP | 8.54E−07 | ACVA | 1.71 E−07 | DMF | 2.04 E−03 | 363 | 75 | 37.7 |
| 74 | DMAE MA | 2.49 E−04 | CTP | 5.18E−07 | ACVA | 1.03 E−07 | DMF | 2.04 E−03 | 363 | 75 | 27.3 |
| 75 | DMAE MA | 2.49 E−04 | CTP | 4.61E−07 | ACVA | 9.05 E−08 | DMF | 2.04 E−03 | 363 | 75 | 26.7 |
| 76 | DMAE MA | 2.49 E−04 | CTP | 4.13E−07 | ACVA | 8.21 E−08 | DMF | 2.04 E−03 | 363 | 75 | 25.1 |
| 77 | DMAE MA | 2.49 E−04 | CTP | 3.65E−07 | ACVA | 7.37 E−08 | DMF | 2.04 E−03 | 363 | 75 | 23.0 |
| 78 | DMAE MA | 2.49 E−04 | CTP | 3.36E−07 | ACVA | 6.74 E−08 | DMF | 2.04 E−03 | 363 | 75 | 22.8 |
| 79 | DMAE MA | 2.49 E−04 | CTP | 2.49E−06 | ACVA | 4.97 E−07 | DMF | 2.04 E−03 | 363 | 75 | 52.7 |
| 80 | DMAE MA | 2.49 E−04 | CTP | 1.52E−06 | ACVA | 3.03 E−07 | DMF | 2.04 E−03 | 363 | 75 | 47.6 |
| 81 | DMAE MA | 2.49 E−04 | CTP | 1.09E−06 | ACVA | 2.19 E−07 | DMF | 2.04 E−03 | 363 | 75 | 39.3 |
| 82 | DMAE MA | 2.49 E−04 | CTP | 8.54E−07 | ACVA | 1.71 E−07 | DMF | 2.04 E−03 | 363 | 75 | 37.1 |
| 83 | DMAE MA | 2.49 E−04 | CTP | 7.00E−07 | ACVA | 1.41 E−07 | DMF | 2.04 E−03 | 363 | 75 | 34.0 |
| 84 | DMAE MA | 2.49 E−04 | CTP | 5.95E−07 | ACVA | 1.18 E−07 | DMF | 2.04 E−03 | 363 | 75 | 31.8 |
| 85 | DMAE MA | 2.49 E−04 | CTP | 5.18E−07 | ACVA | 1.03 E−07 | DMF | 2.04 E−03 | 363 | 75 | 25.1 |
| 86 | DMAE MA | 2.49 E−04 | CTP | 4.61E−07 | ACVA | 9.05 E−08 | DMF | 2.04 E−03 | 363 | 75 | 25.7 |
| 87 | DMAE MA | 2.49 E−04 | CTP | 4.13E−07 | ACVA | 8.21 E−08 | DMF | 2.04 E−03 | 363 | 75 | 23.9 |
| 88 | DMAE MA | 2.49 E−04 | CTP | 7.00E−07 | ACVA | 1.41 E−07 | DMF | 2.04 E−03 | 363 | 75 | 27.7 |
| 89 | DMAE MA | 2.49 E−04 | CTP | 8.54E−07 | ACVA | 1.71 E−07 | DMF | 2.04 E−03 | 363 | 75 | 32.8 |
| 90 | DMAE MA | 2.49 E−04 | CTP | 3.65E−07 | ACVA | 7.37 E−08 | DMF | 2.04 E−03 | 363 | 75 | 21.0 |
| 91 | DMAE MA | 2.53 E−04 | CTP | 8.42E−07 | ACVA | 8.44 E−07 | DMF | 2.03 E−03 | 360 | 70 | 103.4 |
| 92 | MMA | 3.95 E−04 | CTP | 1.32E−06 | AIBN | 2.63 E−07 | DMF | 2.04 E−03 | 360 | 70 | 61.2 |
| 93 | BMA | 2.80 E−04 | ECT | 9.32E−07 | AIBN | 1.86 E−07 | DMF | 2.01 E−03 | 360 | 70 | 32.4 |
| 94 | DMAE MA | 2.53 E−04 | ECT | 8.43E−07 | AIBN | 8.44 E−07 | DMF | 2.03 E−03 | 360 | 65 | 101.0 |
| 95 | MMA | 3.96 E−04 | ECT | 1.32E−06 | ACVA | 1.32 E−07 | DMF | 2.04 E−03 | 360 | 65 | 13.7 |
| 96 | BMA | 2.80 E−04 | CTP | 9.31E−07 | AIBN | 9.32 E−07 | DMF | 2.01 E−03 | 360 | 65 | 32.1 |

TABLE 4

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 1 | HEMA | 2.54 E−05 | p(DMA EMA), (006-A1 Block 1) | 1.27 E−06 | ACVA | 1.27 E−06 | DMF | 8.00 E−04 | 1440 | 64 | 65.3 |
| 2 | HEMA | 2.70 E−05 | p(DMA EMA), (006-A3 Block 1) | 1.33 E−06 | ACVA | 1.33 E−06 | DMF | 8.33 E−04 | 1440 | 64 | 85.7 |
| 3 | HEMA | 2.38 E−05 | p(DMA EMA), (006-A4 Block 1) | 1.19 E−06 | ACVA | 1.19 E−06 | DMF | 7.25 E−04 | 1440 | 64 | 77.4 |
| 4 | HEMA | 1.91 E−05 | p(DMA EMA), (006-A5 Block 1) | 9.60 E−06 | ACVA | 9.60 E−07 | DMF | 5.36 E−04 | 1440 | 64 | 56.6 |
| 5 | HEMA | 2.15 E−05 | p(DMA EMA), (006-A7 Block 1) | 1.08 E−06 | ACVA | 1.08 E−06 | DMF | 5.92 E−04 | 1440 | 64 | 83.8 |
| 6 | HEMA | 2.07 E−05 | p(DMA EMA), (006-A8 Block 1) | 1.03 E−06 | ACVA | 1.03 E−06 | DMF | 5.54 E−04 | 1440 | 64 | 87.4 |
| 7 | HEMA | 1.99 E−05 | p(DMA EMA), (006-A9 Block 1) | 9.78 E−06 | ACVA | 9.78 E−07 | DMF | 5.32 E−04 | 1440 | 64 | 85.5 |
| 8 | HEMA | 1.51 E−05 | p(DMA EMA), (006-A10 Block 1) | 7.57 E−07 | ACVA | 7.56 E−07 | DMF | 3.99 E−04 | 1440 | 64 | 95.6 |
| 9 | HEMA | 1.75 E−05 | p(DMA EMA), (006-A11 Block 1) | 8.71 E−07 | ACVA | 8.71 E−07 | DMF | 4.56 E−04 | 1440 | 64 | 87.4 |
| 10 | HEMA | 1.51 E−05 | p(DMA EMA), (006-A12 Block 1) | 7.48 E−07 | ACVA | 7.49 E−07 | DMF | 3.62 E−04 | 1440 | 64 | 90.2 |
| 11 | HEMA | 7.07 E−05 | p(DMA EMA), (006-B2 Block 1) | 1.55 E−06 | ACVA | 1.56 E−06 | DMF | 2.67 E−03 | 1440 | 64 | 73.3 |
| 12 | HEMA | 4.53 E−05 | p(DMA EMA), (006-B3 Block 1) | 9.93 E−07 | ACVA | 9.95 E−07 | DMF | 1.58 E−03 | 1440 | 64 | 71.6 |
| 13 | HEMA | 5.96 E−05 | p(DMA EMA), (006-B4 Block 1) | 1.31 E−06 | ACVA | 1.31 E−06 | DMF | 2.22 E−03 | 1440 | 64 | 70.3 |
| 14 | HEMA | 5.16 E−05 | p(DMA EMA), (006-B5 Block 1) | 1.12 E−06 | ACVA | 1.12 E−06 | DMF | 1.87 E−03 | 1440 | 64 | 87.8 |
| 15 | HEMA | 5.24 E−05 | p(DMA EMA), (006-B7 Block 1) | 1.15 E−06 | ACVA | 1.15 E−06 | DMF | 1.90 E−03 | 1440 | 64 | 85.3 |
| 16 | HEMA | 3.02 E−05 | p(DMA EMA), (006-B8 Block 1) | 6.62 E−07 | ACVA | 6.60 E−07 | DMF | 1.01 E−03 | 1440 | 64 | 86.3 |
| 17 | HEMA | 2.94 E−05 | p(DMA EMA), (006-B9 Block 1) | 6.35 E−07 | ACVA | 6.35 E−07 | DMF | 9.77 E−04 | 1440 | 64 | 90.9 |

TABLE 4-continued

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 18 | HEMA | 3.18 E−05 | p(DMA EMA), (006-B10 Block 1) | 6.93 E−07 | ACVA | 6.92 E−07 | DMF | 1.02 E−03 | 1440 | 64 | 84.3 |
| 19 | HEMA | 2.94 E−05 | p(DMA EMA), (006-B11 Block 1) | 6.50 E−07 | ACVA | 6.49 E−07 | DMF | 9.96 E−04 | 1440 | 64 | 86.3 |
| 20 | HEMA | 1.45 E−04 | p(DMA EMA), (006-C1 Block 1) | 2.03 E−06 | ACVA | 2.03 E−06 | DMF | 5.86 E−03 | 1440 | 64 | 74.8 |
| 21 | HEMA | 1.12 E−04 | p(DMA EMA), (006-C2 Block 1) | 1.57 E−06 | ACVA | 1.57 E−06 | DMF | 4.41 E−03 | 1440 | 64 | 79.8 |
| 22 | HEMA | 1.02 E−04 | p(DMA EMA), (006-C3 Block 1) | 1.44 E−06 | ACVA | 1.44 E−06 | DMF | 4.03 E−03 | 1440 | 64 | 82.6 |
| 23 | HEMA | 9.06 E−05 | p(DMA EMA), (006-C4 Block 1) | 1.27 E−06 | ACVA | 1.27 E−06 | DMF | 3.55 E−03 | 1440 | 64 | 82.9 |
| 24 | HEMA | 6.83 E−05 | p(DMA EMA), (006-C5 Block 1) | 9.54 E−07 | ACVA | 9.53 E−07 | DMF | 2.56 E−03 | 1440 | 64 | 86.9 |
| 25 | HEMA | 6.52 E−05 | p(DMA EMA), (006-C6 Block 1) | 9.16 E−07 | ACVA | 9.17 E−07 | DMF | 2.50 E−03 | 1440 | 64 | 94.4 |
| 26 | HEMA | 6.91 E−05 | p(DMA EMA), (006-C7 Block 1) | 9.62 E−07 | ACVA | 9.63 E−07 | DMF | 2.61 E−03 | 1440 | 64 | 89.5 |
| 27 | HEMA | 6.36 E−05 | p(DMA EMA), (006-C8 Block 1) | 8.91 E−07 | ACVA | 8.92 E−07 | DMF | 2.44 E−03 | 1440 | 64 | 97.0 |
| 28 | HEMA | 5.01 E−05 | p(DMA EMA), (006-C9 Block 1) | 6.99 E−07 | ACVA | 6.99 E−07 | DMF | 1.86 E−03 | 1440 | 64 | 90.0 |
| 29 | HEMA | 4.93 E−05 | p(DMA EMA), (006-C10 Block 1) | 6.95 E−07 | ACVA | 6.96 E−07 | DMF | 1.86 E−03 | 1440 | 64 | 90.1 |
| 30 | HEMA | 5.40 E−05 | p(DMA EMA), (006-C11 Block 1) | 7.51 E−07 | ACVA | 7.53 E−07 | DMF | 2.02 E−03 | 1440 | 64 | 90.4 |
| 31 | HEMA | 1.99 E−05 | p(DMA EMA), (006-C12 Block 1) | 2.83 E−07 | ACVA | 2.82 E−07 | DMF | 6.23 E−04 | 1440 | 64 | 82.4 |
| 32 | HEMA | 1.87 E−04 | p(DMA EMA), (006-D2 Block 1) | 1.92 E−06 | ACVA | 1.92 E−06 | DMF | 7.52 E−03 | 1440 | 64 | 73.9 |
| 33 | HEMA | 9.69 E−05 | p(DMA EMA), (006-D3 Block 1) | 9.94 E−07 | ACVA | 9.95 E−07 | DMF | 3.77 E−03 | 1440 | 64 | 83.0 |
| 34 | HEMA | 1.12 E−04 | p(DMA EMA), (006-D4 Block 1) | 1.15 E−06 | ACVA | 1.15 E−06 | DMF | 4.45 E−03 | 1440 | 64 | 81.5 |

TABLE 4-continued

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 35 | HEMA | 1.09 E-04 | p(DMA EMA), (006-D6 Block 1) | 1.12 E-06 | ACVA | 1.12 E-06 | DMF | 4.31 E-03 | 1440 | 64 | 85.9 |
| 36 | HEMA | 6.28 E-05 | p(DMA EMA), (006-D8 Block 1) | 6.48 E-07 | ACVA | 6.46 E-07 | DMF | 2.45 E-03 | 1440 | 64 | 94.7 |
| 37 | HEMA | 5.56 E-05 | p(DMA EMA), (006-D9 Block 1) | 5.74 E-07 | ACVA | 5.74 E-07 | DMF | 2.15 E-03 | 1440 | 64 | 96.7 |
| 38 | HEMA | 3.42 E-05 | p(DMA EMA), (006-D11 Block 1) | 3.54 E-07 | ACVA | 3.53 E-07 | DMF | 1.21 E-03 | 1440 | 64 | 90.7 |
| 39 | HEMA | 3.73 E-05 | p(DMA EMA), (006-D12 Block 1) | 3.88 E-07 | ACVA | 3.89 E-07 | DMF | 1.33 E-03 | 1440 | 64 | 76.5 |
| 40 | HEMA | 1.80 E-04 | p(DMA EMA), (006-E1 Block 1) | 1.46 E-06 | ACVA | 1.47 E-06 | DMF | 7.27 E-03 | 1440 | 64 | 81.5 |
| 41 | HEMA | 1.08 E-04 | p(DMA EMA), (006-E4 Block 1) | 8.80 E-07 | ACVA | 8.81 E-07 | DMF | 4.23 E-03 | 1440 | 64 | 80.6 |
| 42 | HEMA | 1.32 E-04 | p(DMA EMA), (006-E5 Block 1) | 1.07 E-06 | ACVA | 1.07 E-06 | DMF | 5.28 E-03 | 1440 | 64 | 81.7 |
| 43 | HEMA | 6.04 E-05 | p(DMA EMA), (006-E9 Block 1) | 4.94 E-07 | ACVA | 4.92 E-07 | DMF | 2.32 E-03 | 1440 | 64 | 92.0 |
| 44 | HEMA | 4.29 E-05 | p(DMA EMA), (006-E10 Block 1) | 3.52 E-07 | ACVA | 3.53 E-07 | DMF | 1.58 E-03 | 1440 | 64 | 82.2 |
| 45 | HEMA | 6.52 E-05 | p(DMA EMA), (006-E11 Block 1) | 5.32 E-07 | ACVA | 5.32 E-07 | DMF | 2.52 E-03 | 1440 | 64 | 81.3 |
| 46 | HEMA | 5.72 E-05 | p(DMA EMA), (006-E12 Block 1) | 4.66 E-07 | ACVA | 4.67 E-07 | DMF | 2.17 E-03 | 1440 | 64 | 70.6 |
| 47 | HEMA | 3.47 E-05 | p(DMA EMA), (006-F3 Block 1) | 2.34 E-06 | ACVA | 2.34 E-06 | DMF | 1.44 E-02 | 1440 | 64 | 76.5 |
| 48 | HEMA | 1.83 E-04 | p(DMA EMA), (006-F4 Block 1) | 1.23 E-06 | ACVA | 1.23 E-06 | DMF | 7.42 E-03 | 1440 | 64 | 77.4 |
| 49 | HEMA | 1.29 E-04 | p(DMA EMA), (006-F7 Block 1) | 8.68 E-07 | ACVA | 8.67 E-07 | DMF | 5.22 E-03 | 1440 | 64 | 80.4 |
| 50 | HEMA | 1.20 E-04 | p(DMA EMA), (006-F8 Block 1) | 8.09 E-07 | ACVA | 8.10 E-07 | DMF | 4.87 E-03 | 1440 | 64 | 81.1 |
| 51 | HEMA | 1.06 E-04 | p(DMA EMA), (006-F9 Block 1) | 7.13 E-07 | ACVA | 7.14 E-07 | DMF | 4.24 E-03 | 1440 | 64 | 75.3 |

TABLE 4-continued

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 52 | HEMA | 2.62 E-05 | p(DMA EMA), (006-F11 Block 1) | 1.79 E-07 | ACVA | 1.78 E-07 | DMF | 8.80 E-04 | 1440 | 64 | 83.2 |
| 53 | HEMA | 9.45 E-05 | p(DMA EMA), (006-F12 Block 1) | 6.36 E-07 | ACVA | 6.35 E-07 | DMF | 3.77 E-03 | 1440 | 64 | 77.4 |
| 54 | HEMA | 3.09 E-04 | p(DMA EMA), (006-G2 Block 1) | 1.77 E-06 | ACVA | 1.77 E-06 | DMF | 1.28 E-02 | 1440 | 64 | 78.8 |
| 55 | HEMA | 2.27 E-04 | p(DMA EMA), (006-G4 Block 1) | 1.30 E-06 | ACVA | 1.30 E-06 | DMF | 9.33 E-03 | 1440 | 64 | 77.3 |
| 56 | HEMA | 2.40 E-04 | p(DMA EMA), (006-G5 Block 1) | 1.38 E-06 | ACVA | 1.38 E-06 | DMF | 9.90 E-03 | 1440 | 64 | 75.0 |
| 57 | HEMA | 1.54 E-04 | p(DMA EMA), (006-G6 Block 1) | 8.86 E-07 | ACVA | 8.85 E-07 | DMF | 6.30 E-03 | 1440 | 64 | 82.7 |
| 58 | HEMA | 1.17 E-04 | p(DMA EMA), (006-G7 Block 1) | 6.72 E-07 | ACVA | 6.71 E-07 | DMF | 4.68 E-03 | 1440 | 64 | 83.9 |
| 59 | HEMA | 9.14 E-05 | p(DMA EMA), (006-G9 Block 1) | 5.26 E-07 | ACVA | 5.24 E-07 | DMF | 3.66 E-03 | 1440 | 64 | 74.6 |
| 60 | HEMA | 9.93 E-05 | p(DMA EMA), (006-G10 Block 1) | 5.70 E-07 | ACVA | 5.71 E-07 | DMF | 3.97 E-03 | 1440 | 64 | N/A |
| 61 | HEMA | 8.66 E-05 | p(DMA EMA), (006-G11 Block 1) | 4.97 E-07 | ACVA | 4.96 E-07 | DMF | 3.43 E-03 | 1440 | 64 | 72.8 |
| 62 | HEMA | 6.36 E-05 | p(DMA EMA), (006-G12 Block 1) | 3.65 E-07 | ACVA | 3.64 E-07 | DMF | 2.51 E-03 | 1440 | 64 | 65.1 |
| 63 | HEMA | 3.78 E-04 | p(DMA EMA), (006-H2 Block 1) | 1.89 E-06 | ACVA | 1.89 E-06 | DMF | 1.57 E-02 | 1440 | 64 | 70.6 |
| 64 | HEMA | 3.50 E-04 | p(DMA EMA), (006-H3 Block 1) | 1.75 E-06 | ACVA | 1.75 E-06 | DMF | 1.46 E-02 | 1440 | 64 | 74.1 |
| 65 | HEMA | 1.87 E-04 | p(DMA EMA), (006-H6 Block 1) | 9.35 E-07 | ACVA | 9.35 E-07 | DMF | 7.69 E-03 | 1440 | 64 | 70.8 |
| 66 | HEMA | 1.78 E-04 | p(DMA EMA), (006-H7 Block 1) | 8.90 E-07 | ACVA | 8.92 E-07 | DMF | 7.28 E-03 | 1440 | 64 | 81.8 |
| 67 | HEMA | 1.16 E-04 | p(DMA EMA), (006-H10 Block 1) | 5.78 E-07 | ACVA | 5.78 E-07 | DMF | 4.67 E-03 | 1440 | 64 | 81.9 |
| 68 | HEMA | 7.23 E-05 | p(DMA EMA), (006-H11 Block 1) | 3.60 E-07 | ACVA | 3.60 E-07 | DMF | 2.86 E-03 | 1440 | 64 | 83.0 |

TABLE 4-continued

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 69 | HEMA | 8.50 E-05 | p(DMA EMA), (006-H12 Block 1) | 4.23 E-07 | ACVA | 4.25 E-07 | DMF | 3.35 E-03 | 1440 | 64 | 70.6 |
| 70 | HEMA | 3.75 E-05 | p(DMA EMA), (007-A1 Block 1) | 1.88 E-06 | ACVA | 3.75 E-07 | DMF | 1.92 E-03 | 1440 | 64 | 55.7 |
| 71 | HEMA | 1.72 E-05 | p(DMA EMA), (007-A2 Block 1) | 8.63 E-07 | ACVA | 1.72 E-07 | DMF | 7.77 E-04 | 1440 | 64 | 71.1 |
| 72 | HEMA | 1.99 E-05 | p(DMA EMA), (007-A3 Block 1) | 9.99 E-07 | ACVA | 2.00 E-07 | DMF | 9.65 E-04 | 1440 | 64 | 76.6 |
| 73 | HEMA | 1.30 E-05 | p(DMA EMA), (007-A4 Block 1) | 6.51 E-07 | ACVA | 1.30 E-07 | DMF | 5.74 E-04 | 1440 | 64 | 80.3 |
| 74 | HEMA | 6.12 E-06 | p(DMA EMA), (007-A7 Block 1) | 3.07 E-07 | ACVA | 6.14 E-08 | DMF | 2.28 E-04 | 1440 | 64 | 73.5 |
| 75 | HEMA | 3.34 E-06 | p(DMA EMA), (007-A8 Block 1) | 1.68 E-07 | ACVA | 3.35 E-08 | DMF | 7.03 E-05 | 1440 | 64 | 72.3 |
| 76 | HEMA | 5.40 E-06 | p(DMA EMA), (007-A9 Block 1) | 2.71 E-07 | ACVA | 5.42 E-08 | DMF | 1.97 E-04 | 1440 | 64 | 66.6 |
| 77 | HEMA | 5.06 E-06 | p(DMA EMA), (007-A10 Block 1) | 2.52 E-07 | ACVA | 5.03 E-08 | DMF | 1.86 E-04 | 1440 | 64 | 73.6 |
| 78 | HEMA | 5.24 E-06 | p(DMA EMA), (007-A11 Block 1) | 2.61 E-07 | ACVA | 5.21 E-08 | DMF | 1.96 E-04 | 1440 | 64 | 77.6 |
| 79 | HEMA | 7.27 E-05 | p(DMA EMA), (006-B1 Block 1) | 1.59 E-06 | ACVA | 3.18 E-07 | DMF | 3.94 E-03 | 1440 | 64 | 45.1 |
| 80 | HEMA | 3.45 E-05 | p(DMA EMA), (007-B2 Block 1) | 7.54 E-07 | ACVA | 1.51 E-07 | DMF | 1.76 E-03 | 1440 | 64 | 67.5 |
| 81 | HEMA | 2.10 E-05 | p(DMA EMA), (007-B3 Block 1) | 4.58 E-07 | ACVA | 9.17 E-08 | DMF | 1.02 E-03 | 1440 | 64 | 66.6 |
| 82 | HEMA | 3.26 E-05 | p(DMA EMA), (007-B4 Block 1) | 7.13 E-07 | ACVA | 1.43 E-07 | DMF | 1.71 E-03 | 1440 | 64 | 52.8 |
| 83 | HEMA | 1.84 E-05 | p(DMA EMA), (007-B5 Block 1) | 4.02 E-07 | ACVA | 8.06 E-08 | DMF | 9.00 E-04 | 1440 | 64 | 76.9 |
| 84 | HEMA | 2.63 E-05 | p(DMA EMA), (007-B6 Block 1) | 5.76 E-07 | ACVA | 1.15 E-07 | DMF | 1.37 E-03 | 1440 | 64 | 60.8 |
| 85 | HEMA | 1.81 E-05 | p(DMA EMA), (007-B7 Block 1) | 3.96 E-07 | ACVA | 7.92 E-08 | DMF | 9.29 E-04 | 1440 | 64 | 70.2 |

TABLE 4-continued

Summary of Block 2 Reagents and Reaction Conditions Used in Pilot PNP Library

Block 2 Reagents, Purpose, Amounts, and Reaction Conditions

| PNP | Monomer and Amount (mol) | | Macro Chain Transfer Agent (mCTA) and Amount (mol) | | Initiator and Amount (mol) | | Solvent and Amount (mol) | | Time (min) | Temp (C.) | Diblock Post-Lyophilization % Yield |
|---|---|---|---|---|---|---|---|---|---|---|---|
| 86 | HEMA | 2.14 E-05 | p(DMAEMA), (007-B8 Block 1) | 4.67 E-07 | ACVA | 9.35 E-08 | DMF | 1.11 E-03 | 1440 | 64 | 69.4 |
| 87 | HEMA | 1.64 E-05 | p(DMAEMA), (007-B9 Block 1) | 3.58 E-07 | ACVA | 7.17 E-08 | DMF | 8.34 E-04 | 1440 | 64 | 79.0 |
| 88 | HEMA | 8.48 E-05 | p(DMAEMA), (007-E5 Block 1) | 6.90 E-07 | ACVA | 1.38 E-07 | DMF | 4.76 E-03 | 1440 | 64 | 62.9 |
| 89 | HEMA | 1.45 E-04 | p(DMAEMA), (007-F4 Block 1) | 9.74 E-07 | ACVA | 1.95 E-07 | DMF | 8.18 E-03 | 1440 | 64 | 49.4 |
| 90 | HEMA | 5.07 E-05 | p(DMAEMA), (007-E10 Block 1) | 4.12 E-07 | ACVA | 8.24 E-08 | DMF | 2.82 E-03 | 1440 | 64 | 46.5 |
| 91 | MMA | 3.17 E-04 | p(DMAEMA), (009-A10 Block 1) | 1.06 E-06 | ACVA | 1.06 E-06 | DMF | 9.27 E-04 | 1440 | 60 | 30.5 |
| 92 | DMAEMA | 8.08 E-04 | p(MMA), (009-E8 Block 1) | 2.69 E-06 | AIBN | 5.39 E-07 | DMF | 1.72 E-03 | 1440 | 60 | 61.9 |
| 93 | DMAEMA | 9.92 E-04 | p(BMA), (009-G2 Block 1) | 3.31 E-06 | AIBN | 6.61 E-07 | DMF | 2.11 E-03 | 1440 | 60 | 74.4 |
| 94 | BMA | 7.75 E-04 | p(DMAEMA), (011-B1 Block 1) | 2.58 E-06 | AIBN | 2.58 E-06 | DMF | 1.74 E-03 | 1440 | 60 | 17.3 |
| 95 | DMAEMA | 1.25 E-04 | p(MMA), (011-E6 Block 1) | 4.16 E-07 | ACVA | 4.17 E-08 | DMF | 2.66 E-04 | 1440 | 60 | 21.2 |
| 96 | DMAEMA | 2.71 E-04 | p(BMA), (011-G7 Block 1) | 9.04 E-07 | AIBN | 9.04 E-07 | DMF | 5.78 E-04 | 1440 | 60 | 53.6 |

TABLE 5

Summary of Pilot PNP Library Characterization Data

| PNP | Block 1 DynaPro Result (molar mass, kDa) | DynaPro DLS Z-Avg Result (size, nm) | Size PDI (goal < 0.3) |
|---|---|---|---|
| 1 | 16.3 | 386.9 | Multimodal |
| 2 | 16.8 | 574.3 | Multimodal |
| 3 | 17.9 | 331.8 | 0.121 |
| 4 | 21.6 | 345.1 | 0.152 |
| 5 | 22.3 | 355.8 | 0.483 |
| 6 | 23.3 | 379.7 | 0.268 |
| 7 | 22.7 | 365.7 | 0.219 |
| 8 | 23.9 | 317.8 | 0.040 |
| 9 | 24.1 | 296.2 | 0.137 |
| 10 | 27.2 | 323.9 | 0.254 |
| 11 | 17.4 | 1017.8 | 0.166 |
| 12 | 26.9 | 1368.9 | Multimodal |
| 13 | 18.7 | 450.2 | 0.087 |
| 14 | 20.9 | 389.2 | 0.152 |
| 15 | 21.9 | 291.5 | 0.111 |
| 16 | 31.2 | 361 | 0.243 |
| 17 | 30.3 | 317.7 | 0.201 |
| 18 | 35.0 | 345.3 | 0.114 |
| 19 | 30.7 | 267.1 | 0.137 |

TABLE 5-continued

Summary of Pilot PNP Library Characterization Data

| PNP | Block 1 DynaPro Result (molar mass, kDa) | DynaPro DLS Z-Avg Result (size, nm) | Size PDI (goal < 0.3) |
|---|---|---|---|
| 20 | 12.1 | 1383 | 0.238 |
| 21 | 17.7 | 459 | 0.301 |
| 22 | 18.8 | 436.7 | 0.314 |
| 23 | 18.6 | 448 | 0.492 |
| 24 | 26.7 | 422.8 | 0.368 |
| 25 | 24.1 | 333 | 0.214 |
| 26 | 25.1 | 275.6 | Multimodal |
| 27 | 22.8 | 318.3 | 0.219 |
| 28 | 28.9 | 342 | 0.557 |
| 29 | 27.0 | 222.5 | Multimodal |
| 30 | 26.5 | 251.3 | 0.48 |
| 31 | 62.1 | 207.3 | 0.548 |
| 32 | 17.0 | 522.5 | 0.435 |
| 33 | 26.4 | 477.6 | Multimodal |
| 34 | 20.8 | 369.9 | 0.237 |
| 35 | 22.9 | 321.4 | 0.276 |
| 36 | 26.4 | 282.4 | 0.229 |
| 37 | 30.4 | 319.1 | 0.351 |
| 38 | 54.2 | 262.3 | 0.202 |
| 39 | 53.1 | 315.5 | 0.171 |
| 40 | 20.8 | 730.2 | Multimodal |
| 41 | 31.9 | 379.8 | 0.332 |
| 42 | 24.3 | 309.2 | 0.237 |
| 43 | 40.9 | 317.8 | 0.338 |
| 44 | 56.5 | 1186.1 | 0.271 |
| 45 | 37.7 | 386.4 | 0.153 |
| 46 | 43.2 | 279.6 | 0.138 |
| 47 | 14.7 | 413.3 | 0.29 |
| 48 | 23.6 | 351 | 0.218 |
| 49 | 24.2 | 266.7 | 0.524 |
| 50 | 24.0 | 249.3 | 0.401 |
| 51 | 29.0 | 269.9 | 0.371 |
| 52 | 105.1 | 271.2 | 0.074 |
| 53 | 30.4 | 302.5 | 0.145 |
| 54 | 18.0 | 375.2 | Multimodal |
| 55 | 20.5 | 440.4 | 0.496 |
| 56 | 19.0 | 296.3 | 0.109 |
| 57 | 24.8 | 277.1 | 0.475 |
| 58 | 34.7 | 299.6 | 0.393 |
| 59 | 36.0 | 269 | 0.351 |
| 60 | 34.9 | 264.8 | 0.181 |
| 61 | 40.5 | 353.1 | 0.138 |
| 62 | 41.3 | 230.5 | 0.151 |
| 63 | 16.2 | 354.5 | Multimodal |
| 64 | 15.0 | 355.5 | 0.334 |
| 65 | 23.7 | 332.6 | 0.231 |
| 66 | 26.6 | 253.4 | 0.217 |
| 67 | 34.6 | 294.3 | 0.151 |
| 68 | 44.3 | 275.2 | 0.207 |
| 69 | 45.6 | 404.8 | 0.287 |
| 70 | 9.4 | 2023.5 | 0.020 |
| 71 | 18.3 | 473.2 | 0.521 |
| 72 | 13.5 | 549.2 | 0.153 |
| 73 | 19.7 | 568 | Multimodal |
| 74 | 30.0 | 262 | 0.353 |
| 75 | 53.7 | 229.4 | Multimodal |
| 76 | 31.3 | 230.7 | 0.444 |
| 77 | 30.3 | 387.4 | Multimodal |
| 78 | 29.5 | 266.7 | Multimodal |
| 79 | 11.4 | 1155.7 | Multimodal |
| 80 | 21.3 | 619.2 | 0.198 |
| 81 | 28.9 | 337.7 | 0.053 |
| 82 | 17.5 | 336 | 0.13 |
| 83 | 28.8 | 90.5 | Multimodal |
| 84 | 19.0 | 251.3 | 0.164 |
| 85 | 21.1 | 360.6 | Multimodal |
| 86 | 18.8 | 225.3 | Multimodal |
| 87 | 22.4 | 168 | Multimodal |
| 88 | 13.1 | 298.6 | 0.217 |
| 89 | 11.0 | 281 | 0.314 |
| 90 | 16.3 | 300 | 0.503 |
| 91 | 29.0 | 214 | 0.293 |
| 92 | 9.1 | 14.2 | 0.412 |
| 93 | 3.9 | 21.2 | Multimodal |
| 94 | 15.6 | 432.8 | Multimodal |

TABLE 5-continued

Summary of Pilot PNP Library Characterization Data

| PNP | Block 1 DynaPro Result (molar mass, kDa) | DynaPro DLS Z-Avg Result (size, nm) | Size PDI (goal < 0.3) |
|---|---|---|---|
| 95 | 13.2 | 268.9 | Multimodal |
| 96 | 14.2 | 657.2 | 0.356 |

Example 6

Figure 9:
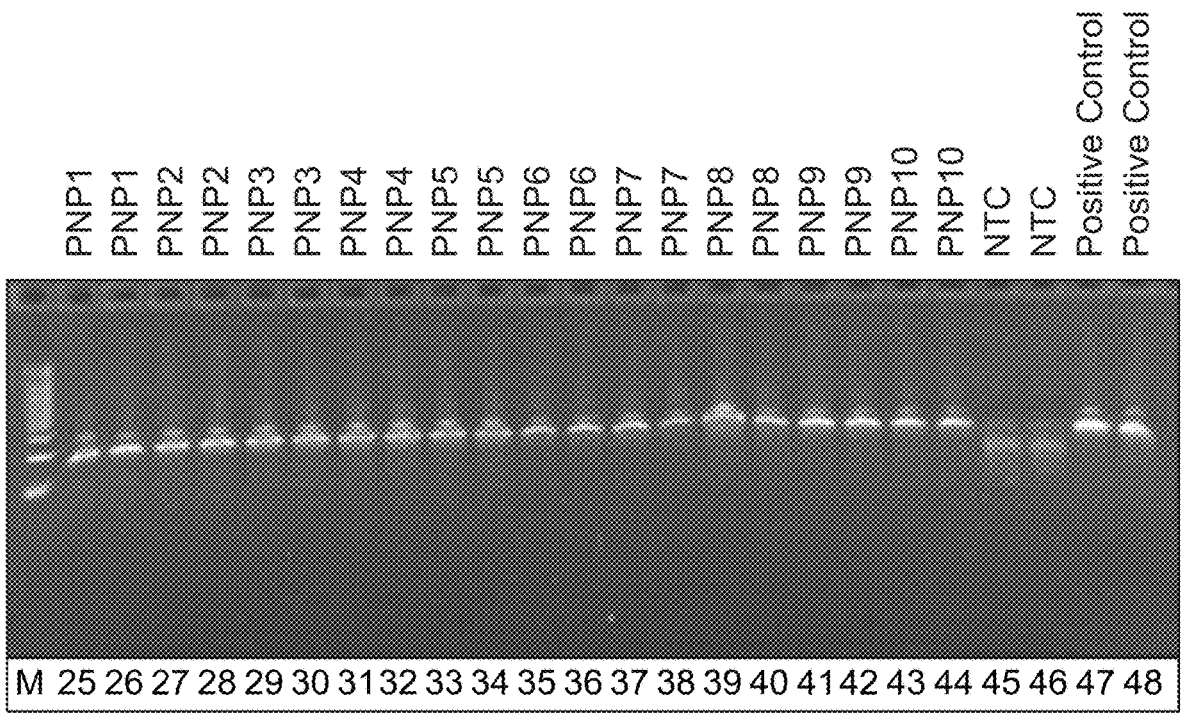
FIG. 9 is an e-gel showing DNA barcode amplification from 10 unique of PNPs with unique barcodes, after being spiked into HEK-293 cells. The presence of the double band is evidence of barcode amplification, present in the positive control sample known to have the barcodes, and not observed in the no test control (NTC) sample, which was phosphate buffered saline only.

Composition Example 3 (CE3): Nucleic Acid Constructs Conjugation to PNPs Direct Amidification With an Amine Terminal Nucleic Acid Construct RAFT copolymers made using CTAs that contain at least one carboxyl terminal group were further functionalized with amine terminal DNA barcodes. A RAFT copolymer was transferred into a MES buffer at ~12 mg/mL. The sample was sonicated for 30 minutes. EDC reagent and Sulfo-NHS reagent was added to the polymer at a molar ratio of 10:1 and 25:1 respectively, reagent to PNP. The sample was incubated for at least 10 minutes at room temperature to allow the reaction to occur. The reaction volume was filtered through a membrane with a molecular weight cut off of 30 kDa via centrifuge at ~3000× g for ~15 minutes. The filtrate was discarded, and sterile PBS was added to the retentate to reconstitute to 10 mg/mL polymer. A nucleic acid constructs with a primary amine group attached to the 5' end was added to polymer and the sample was incubated for at least 15 minutes. The sample was transferred to an amicon ultra-4 centrifuge tube (MWCO 30 kDa, Max 3.5 mL/Tube) and centrifuged at 4,000× g for 15 minutes to remove any unbound nucleic acid constructs. The filtrate (containing unbound nucleic acid constructs) was discarded and sterile PBS was added to the retentate to final concentration of 8 mg/mL polymer. The conjugated barcodes were amplified via PCR, using primers designed to bind to the primer binding segments on the nucleic acid constructs. The amplicons were detected via gel electrophoresis on agarose gel. The presence of a double band (FIG. 9) in a lane indicates the presence of amplicons, showing that nucleic acid constructs were bound to the PNPs.

The direct amidification method was used to attach 10 unique barcodes to 10 unique PNPs. The 10 unique PNPs were prepared according to the reagents shown in EXAMPLE 5.

Figure 10:
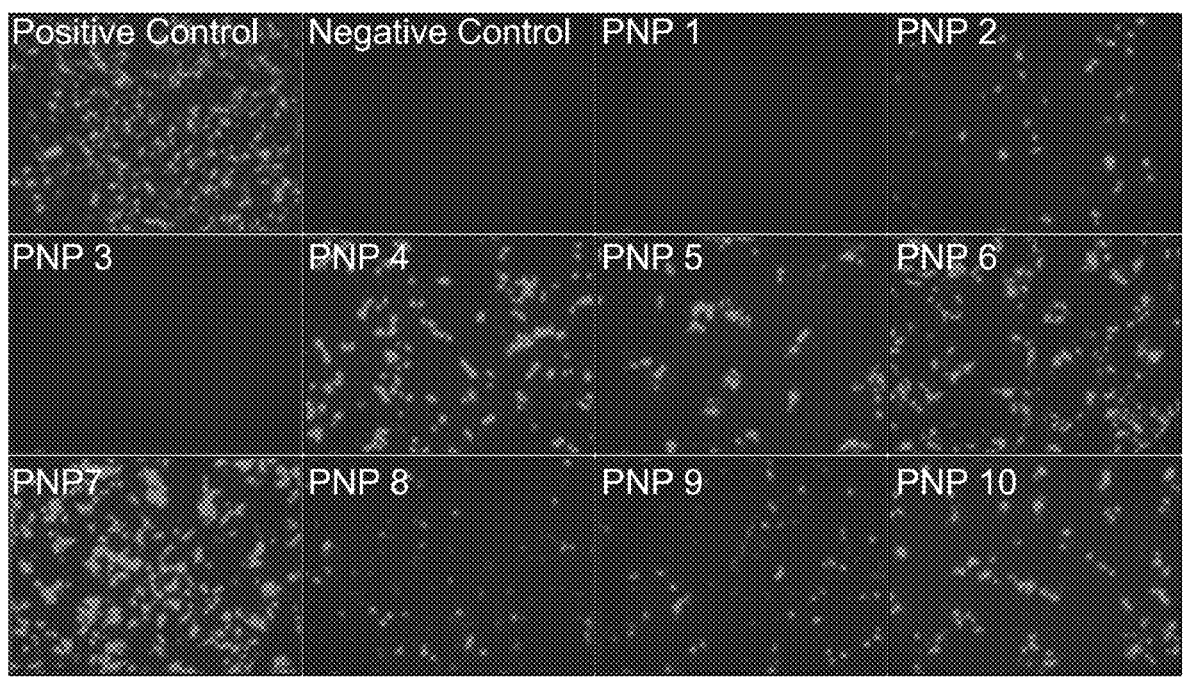
FIG. 10 is a series of images showing each of the 10 unique barcoded PNPs from FIG. 7 were loaded with a plasmid expressing a fluorescent TdTomato protein. The loaded PNPs were each dosed into HEK-293 cells. After 48 hours, the cells were imaged via fluorescent microscopy with a Texas Red filter, and the images are shown above.

Subsequently, the direct amidification method was used to attach 10 unique DNA barcodes to each PNP, giving each a unique label. The nucleic acid construct-PNPs were loaded with a pDNA encoding for the expression of tdTomato red fluorescent protein, and then used to treat HEK-293T cells at ~0.024 mg/mL PNP, 24 hours after seeding in a 96 well plate at 20,000 cells per well. They were left to incubate for another 48 hours, at which time, expression of the payload was observed via fluorescence microscopy using a Texas Red filter set (FIG. 10). This provides evidence that the nucleic acid constructs-PNPs are capable of being taken up by mammalian cells and delivering a payload, as indicated by the red fluorescent images.

Figure 11A:
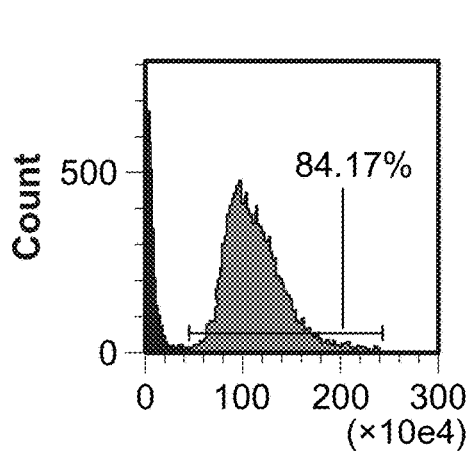
FIG. 11(a)-FIG. 11(e) show flow cytometry scatter plots depicting cell event distribution of HEK293T cells treated with a representative PNP carrying a td-tomato encoding fluorescent cargo plasmid (FIGS. 11(a)-11(c)), and heat maps depicting Transfection efficiency and viability of a library of 88 diverse PNPs (PNP Library Transfection Efficiency (FIG. 11(d)) and PNP Library Viability (FIG. 11(e))).
Figure 11B:
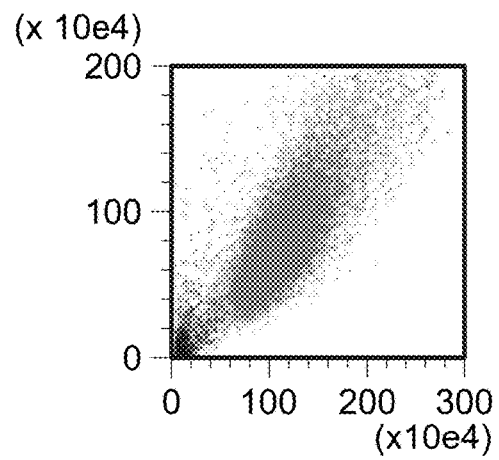
Figure 11C:
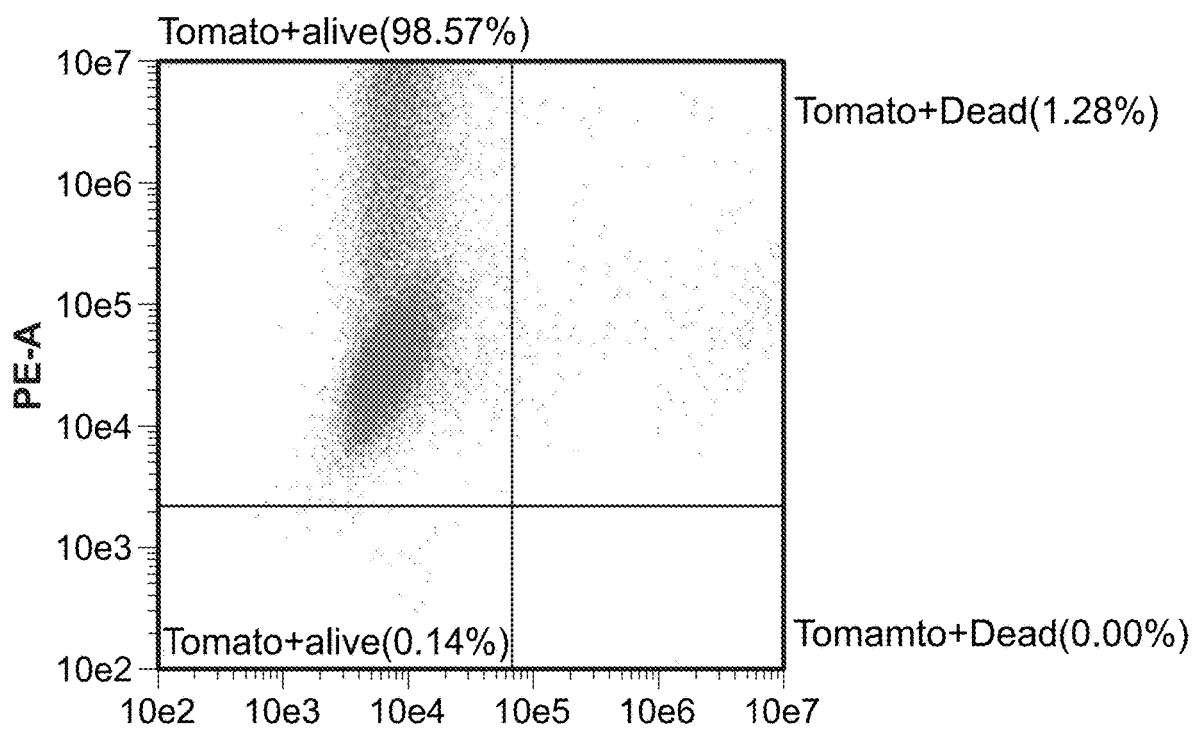
Figure 11D:
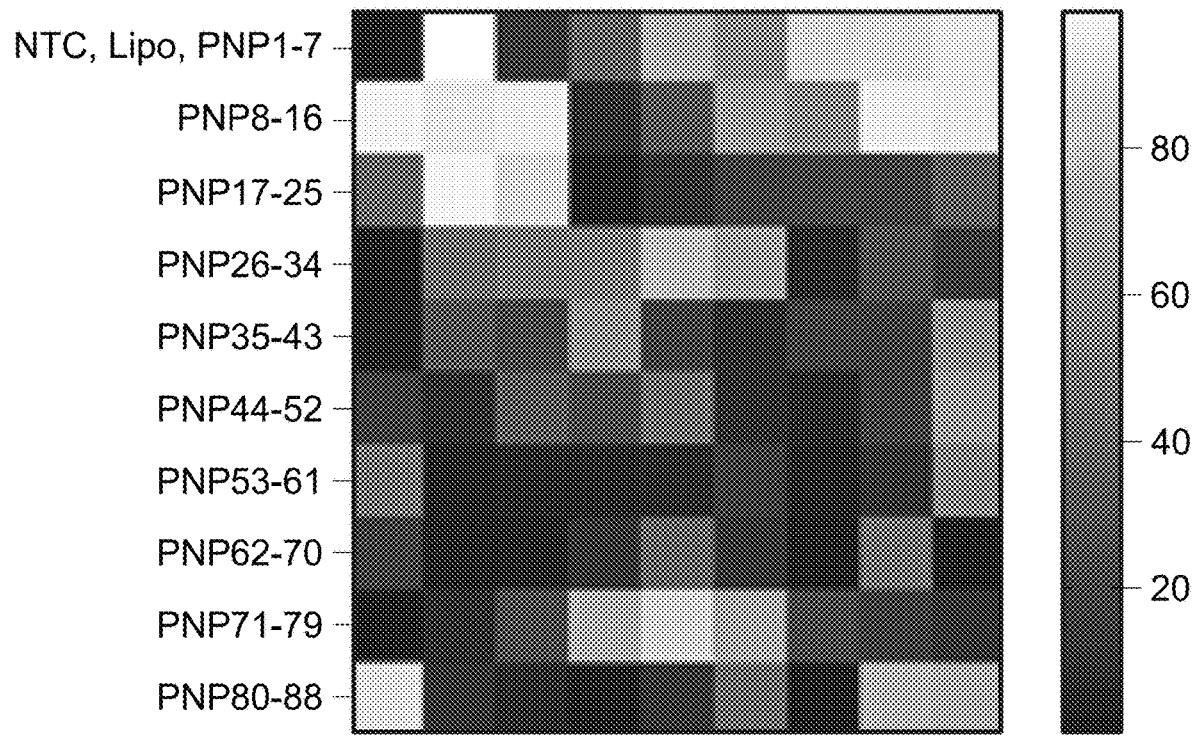
Figure 11E:
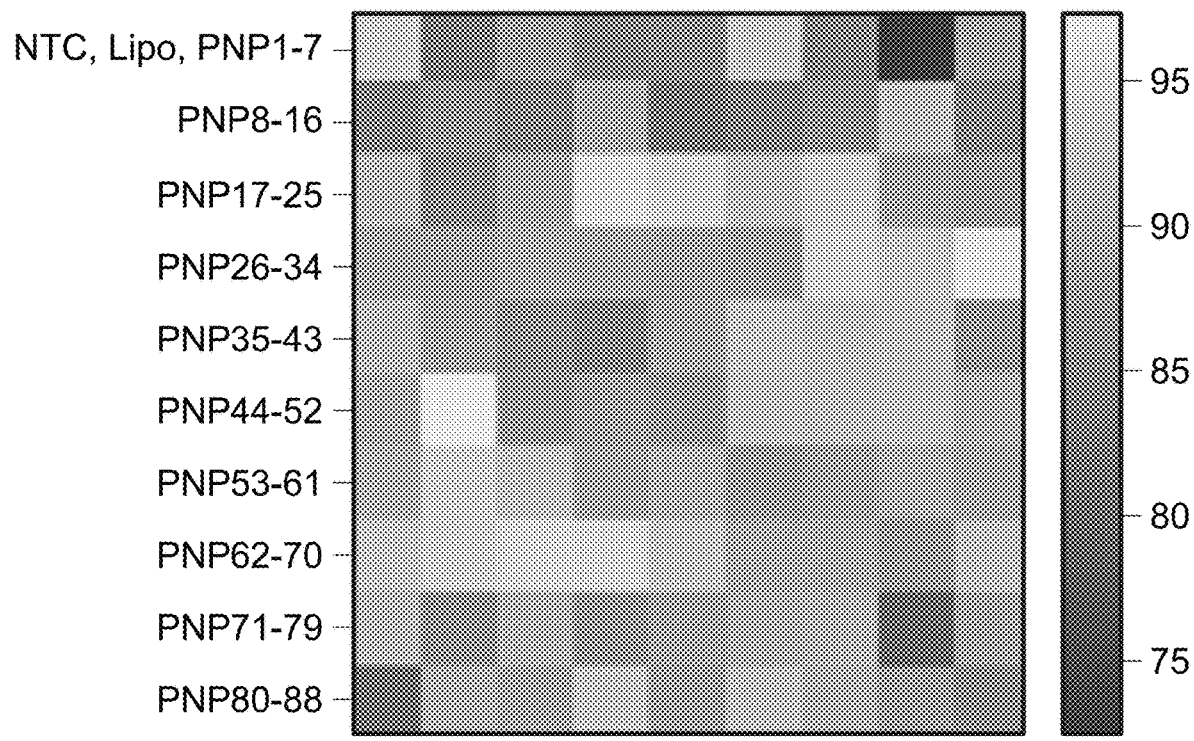

The direct amidification method was then used to attach 88 unique barcodes to 88 unique PNPs. The 88 unique PNPs were prepared according to the reagents shown in EXAMPLE 5. The amidification method was then used to attach 88 unique DAN barcodes to each PNP giving each a unique label. The nucleic acid construct-PNPs were loaded with a pDNA encoding for the expression of tdTomato red fluorescent protein, and then used to treat HEK-293T cells at ~0.024 mg/mL PNP, 24 hours after seeding in a 96 well plate at 20,000 cells per well. They were left to incubate for another 48 hours, at which time, expression of the payload was measured via flow cytometry using a Cytoflex (FIGS. 11(a)-(c)). This provided evidence that some of the nucleic acid construct-PNPs were able to be taken up by mammalian cells. The cells were also given a live/dead stain using zombie dye, and cell viability was measured via flow cytometry (FIGS. 11(d)-(e)) showing that the PNPs were of relatively low cytotoxicity, with cell viability numbers of greater than 75% for the vast majority of PNPs.

Example 7

Methods for Screening Nucleic Acid Construct-PNPs In Vitro and In Vivo

The pooled sample of polymer nanoparticles produced from the recipe in Table 2, with 96 unique barcodes attached via avidin-biotin linkange, was used for measuring cell uptake and cytotoxicity in vitro in HEK293T cells, and for measuring biodistribution in vivo administration in mice. nucleic acid construct-PNPs were formulated in a sterile saline solution and stored at 4° C. for up to 1 month prior to in vivo dosing. Cell uptake efficiency and cytotoxicity are assessed in vitro using HEK293T cells with 0.024 mg/mL PNP at 250 ng or 150 ng/well pDNA treatment concentrations. Cell uptake was demonstrated by fluorescence microscopy. Animals are assigned to dose groups using a stratified randomization program designed to maintain similar group mean body weights by sex. Animals are administered either a control or test article via a single bolus intravenous tail-vein injections. Tested doses ranged from 0-150 mg/kg, with adverse clinical events being observed in 35% of animals at 150 mg/kg. Blood and tissue are collected from all animals and snap frozen in liquid nitrogen.

Example 8

Extraction of Nucleic Acid Construct-PNPs from In Vitro Biological Samples 10-20 mg of tissues are placed in a Tris-EDTA lysis buffer and homogenized using the TissueLyser bead-beating system and a 5 mm stainless steel bead. Homogenization is carried out at 25 Hz in 5-7 minute intervals until solution is homogenous in appearance. Proteinase K is then added to the lysate for protein digestion and incubated in a Thermomixer at 55° C. for 2-4 hours. DNA is extracted from the tissue lysate using the QlAamp 96 DNA extraction kit and a Qiacube HT instrument according to the manufacturer's protocol. Concentration and purity of isolated samples is determined using a NanoDrop.

Example 9

PCR Amplification of Polynucleotide Barcodes in Nucleic Acid Constructs

Polymerase chain reaction is used to produce amplicons from extracted nucleic acid constructs. PCR is performed using a single set of universal primers that anneal to the universal amplification sites on the barcode, thereby amplifying all unique barcodes within a sample in a single reaction. Positive amplification of barcode(s) within a sample is determined using electrophoresis (agarose gel or bioanalyzer) indicated by the presence of a band at ~120 bp.

Example 10

Library Preparation and Sequencing of Nucleic Acid Constructs

Sequencing libraries are prepared from the amplicons generated during first stage PCR amplification. Our universal primers also contain overhang sequences that enable attachment of Index Adapters for sequencing. Illumina Unique Dual Indexes are annealed to the overhangs on the amplicon by PCR. Individual indexed libraries are then pooled in equal amounts and purified using a NucleoSpin Gel and PCR Clean-up kit according the manufacturer's protocols. The molar concentration of the final sequencing library is determined using a Qubit dsDNA High Sensitivity Assay kit and Qubit Fluorometer. The library is spiked with 2% PhiX, diluted to 1.8 pM and loaded onto a High Output 300 cycle NextSeq sequencing cardrige. Paired end sequencing is performed using a NextSeq550 instrument.

Example 11

Sequence Analysis and Bioinformatics

Merged reads from each Sample ID are demultiplexed into PE FASTQ files, and merged into a single file. The merged reads are processed to identify those containing both the 5' and 3' flanking adapters. Trimmed reads are then downselected for sequences containing the correct barcode length. Barcode counts are generated from these downselected sequences and tagged according to whether they are spiked or random. Barcode counts are then normalized to the number of FASTQ reads in the sample.

Hypothetical Example

By way of example, in one illustrative embodiment, the presently disclosed rapid DBTL technologies may be used to develop a gene therapy for forms of amyotrophic lateral sclerosis (ALS) caused by toxic, gain-of-function mutations in superoxide dismutase 1 (SOD1). This gene therapy may involve delivering a CRISPR base-editing protein via a non-viral gene delivery vehicle to inactivate the production of mutant SOD1 protein in microglia, a cell type that modulates the progression of the disease but remains refractory to efficient viral transduction. This will enable safe and efficient therapeutic "hit-and-run" editing for ALS.

An exemplary disease that can be treated with the methods described herein is ALS. ALS is a rapidly progressive, paralytic, and invariably fatal disorder characterized by the selective loss of motor neurons in the spinal cord and brain. Though most cases of ALS are sporadic, dominantly inherited mutations in SOD1 (a ubiquitously expressed metalloenzyme that normally converts superoxide anions into oxygen and hydrogen peroxide) account for up to 20% of all inherited or familial forms of ALS. Base editors are a recently emerged gene-editing modality capable of introducing targeted single-base substitutions in DNA without the requirement for a double-strand break (DSB). Base editors consist of fusions of a catalytically impaired Cas9 nuclease variant, known as a Cas9 nickase, with a nucleobase deaminase enzyme. This example will rely on the ability of base editors, specifically cytidine base editors (CBEs), to catalyze C>T base transitions at CGA, CAG or CAA triplets in a target gene sequence, which creates an in-frame stop codon that triggers the degradation of a target mRNA by nonsense-mediated decay—a surveillance mechanism used by cells to prevent the formation of truncated proteins. Using this method, SOD1 will be inactivated in a manner that does not require a DSB and does not rely on the stochastic and mutagenic NHEJ repair pathway, thus overcoming two of the major limitations facing the clinical implementation of CRISPR-Cas9 for ALS. Thus, while first generation CRISPR is considered the "cut and paste" of gene editing, base editors are considered to be an "eraser and pencil" function, allowing for precise single base edits to a genome, opening new mechanisms for revolutionary ALS treatments. However, innovations in gene delivery have significantly lagged innovations in technologies for gene editing itself. Thus, efficient delivery of base editing systems to the specific cell types involved in driving the progression of ALS represents a key limitation impeding its safe and efficient implementation for treatment of the disorder. Non-viral delivery vehicles will be used to address many of these limitations.

In this illustrative example, the rapid DBTL technologies can iterate through hundreds of diverse polymer nanoparticle candidates, using automated high-throughput synthesis of diverse polymer nanoparticle libraries, parallel in vitro and in vivo screens of barcoded libraries, and a machine learning algorithm to analyze the large data sets and predict new libraries for rapid iteration. FIG. 1 presents a simplified flow diagram illustrating a DBTL cycle for non-viral gene delivery development based on automated synthesis, high throughput testing, and machine learning design.

Hypothetical Example

Figure 2:
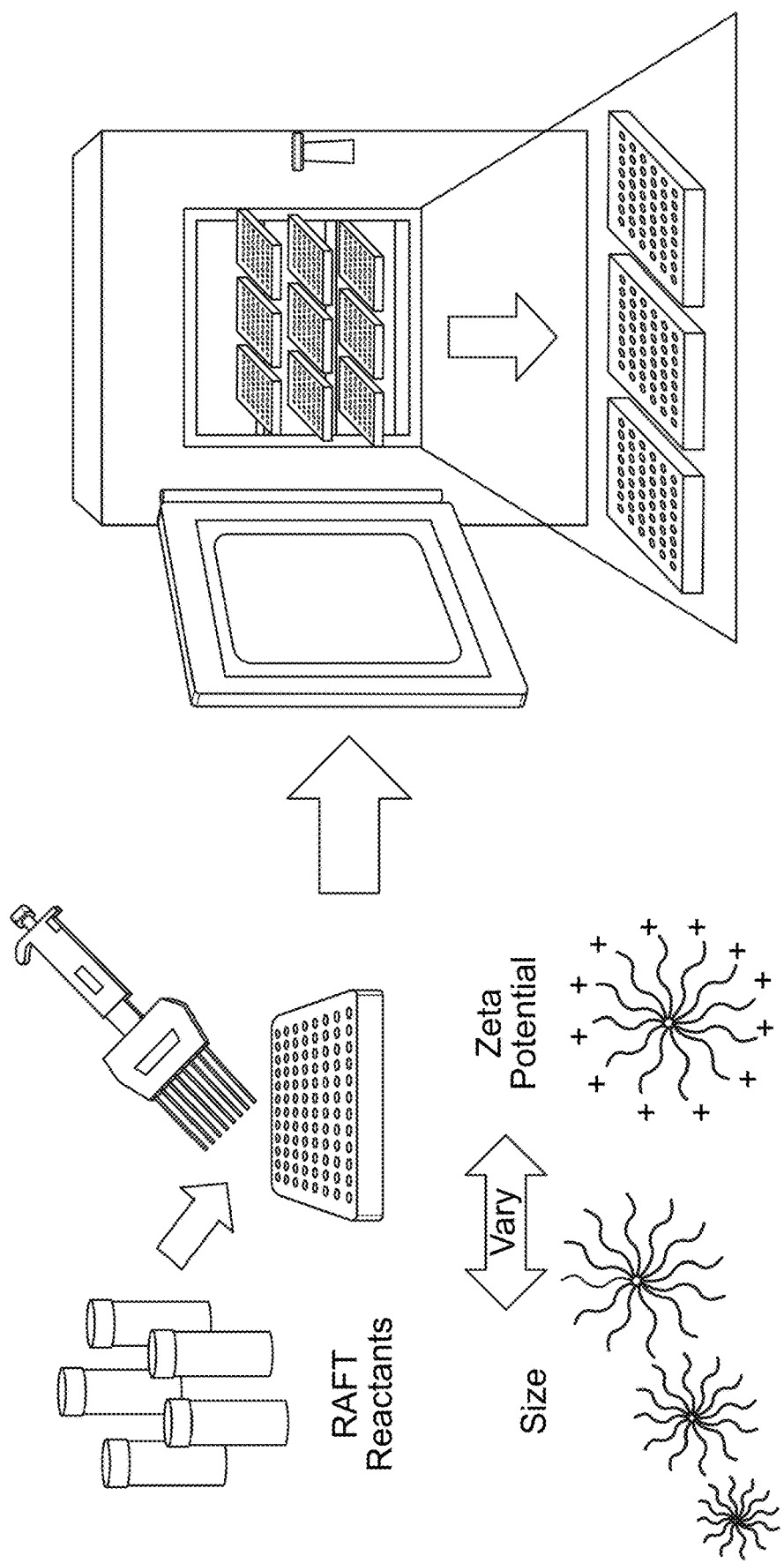
FIG. 2 is a schematic diagram showing an automated multiplexed synthesis of a large, diverse library of PNPs, with various size, charge and hydrophobicity to generate data for gene editing, cytotoxicity, and inflammation.

In one aspect, a library of 100s of polymer nanoparticles (PNPs) encapsulating CBE mRNA can be screened in a high throughput in vitro and in vivo platform. In the illustrative embodiment, over 500 PNPs are synthesized and uniquely labeled and tracked via DNA barcoding. A highly versatile PNP platform based on reversible addition-fragmentation chain transfer (RAFT) polymerization will be used due to its flexibility, reproducibility, and scalability. See K. Sims et al., "Rigor and reproducibility in polymer nanoparticle synthesis and characterization," *Rsc Advances* 2020, 10 (5), 2513-2518 (incorporated herein by reference). As shown in FIG. 2, the RAFT polymerization platform can be used to generate highly monodisperse PNPs with a diverse variety of sizes, charges and chemical make-up. The PNPs can be functionalized to attach cell penetrating peptides to enable higher order functionality and protection to both the vehicle and the cargo. In some embodiments, PNPs may be labeled with quantum dots and other biomarkers via avidin-biotin conjugation. See A. Duong et al., "Scalable, Semicontinuous Production of Micelles Encapsulating Nanoparticles via Electrospray," *Langmuir* 2014, 30 (14), 3939-3948. (incorporated herein by reference). This combination of microglia non-viral delivery vehicles with base editing payloads is highly innovative because it has the potential to lead to a new therapy for ALS. Moreover, the DBTL technologies of the present disclosure are generalizable to enable the creation of advanced non-viral delivery vehicles capable of accessing the other cell types involved in ALS.

After library synthesis, as described above, these PNPs can then be rapidly tested in vitro in a microglial cell line for toxicity, inflammation, and mRNA delivery efficiency via GFP expression. In parallel, the biodistribution and toxicity of the entire library can be assessed using loaded nanoparticles delivered via an intrathecal injection to the cerebrospinal fluid (CSF) of the G93A-SOD1 mouse model of ALS using an mRNA encoding a bioluminescent luciferase that can be tracked via in vitro imaging system (IVIS). This screen should result in three large data sets including particle physical characteristics, in vitro bioactivity, and in vivo biodistribution and toxicity, which, taken together, will provide the basis for an informed design of a novel non-viral delivery vehicle library which will be synthesized in a second iteration. This novel library can then be tested for functional gene editing tests in a microglial cell line modified to express a mutant SOD1 protein. The PNPs can be loaded with mRNA encoding CBE designed to inactivate GFP and SOD1, detected by fluorescence measurement and sequencing.

What is claimed is:

1. A composition comprising:
   a) a non-viral delivery vehicle comprising one or more nanoparticle forming polymers, and
   b) a nucleic acid construct, wherein the one or more nanoparticle forming polymers are RAFT block copolymers comprising
      i) a first terminus comprising a first capping unit derived from a first chain transfer agent in a RAFT copolymerization process, said first chain transfer agent comprising a first reactive functional unit;
      ii). a first block prepared from one or more monomer units covalently attached to the first reactive functional unit, and having a molecular weight ($M_n$) in the range of about 1 kDa to about 200 kDa and a degree of polymerization in the range of about 10 to about 2500;
      iii). optionally a second block prepared from one or more monomer units covalently attached to the first block, and having a molecular weight ($M_n$) in the range of about 1 kDa to about 200 kDa and a degree of polymerization in the range of about 20 to about 2000; and
      iv) a second terminus comprising a second capping unit derived from the first or a second chain transfer agent.

2. The composition of claim 1, wherein the non-viral delivery vehicle has one or more of an overall molecular weight ($M_n$) in the range of about 25 kDa to about 60 kDa, an overall degree of polymerization in the range of about 700 to about 900, a target size in the range of about of about 10 to about 60 nm, and a maximum corona-to-core ratio (CCR) of about 1.5 to about 3.5.

3. The composition of claim 1, wherein the first block is prepared from one or more monomer units selected from the group consisting of 2-dimethylaminoethyl acrylate, 2-(di-ethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

4. The composition of claim 1, wherein the first block is prepared from one of 2-dimethylaminoethyl acrylate, 2-(di-ethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

5. The composition of claim 1, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

6. The composition of claim 1, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

7. The composition of claim 1, wherein the second block is a random copolymer prepared from three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

8. The composition of claim 1, wherein the second block is a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

9. The composition of claim 1, wherein each chain transfer agent is independently selected from the group consisting of bis(carboxymethyl)trithiocarbonate, bis(2-amino-2-oxoethyl) trithiocarbonate, bis[4-(2-hydroxyethoxycarbonyl)benzyl]trithiocarbonate, 4-cyano-4-(ethylsulfanylthiocarbonyl)sulfanylvpentanoic acid, 4-cyano-4-((phenylcarbonothioyl)thio)pentanoic acid, and 4-cyano-4-[(dodecylsulfanylthiocarbonyl)sulfanyl]pentanoic acid.

10. The composition of claim 1, wherein the first capping unit is of the formula

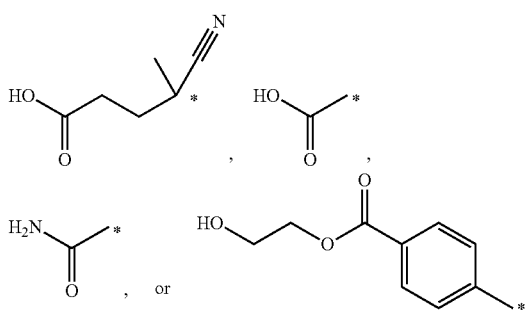

wherein * represents a point of covalent attachment to the first block.

11. The composition of claim 1, wherein the second capping unit is of the formula

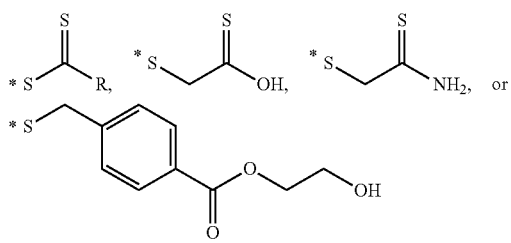

wherein * represents a point of covalent attachment to the second block, and R is —SC$_2$-C$_{12}$ alkyl or C$_6$H$_5$.

12. A composition of claim 1 wherein
said first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate;
said second block comprises a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid; and
each chain transfer agent is independently selected from the group consisting of bis(carboxymethyl)trithiocarbonate, bis(2-amino-2-oxoethyl) trithiocarbonate, bis[4 (2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl)thio) pentanoic acid, and 4-cyano-4-[(dodecylsulfanylthiocarbonyl)sulfanyl] pentanoic acid.

13. The composition of claim 12, wherein the first capping unit is of the formula

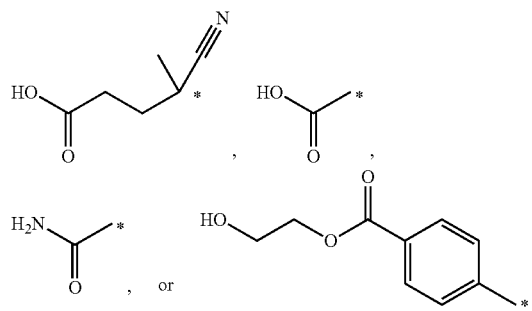

wherein * represents a point of covalent attachment to the first block; and the second capping unit is of the formula

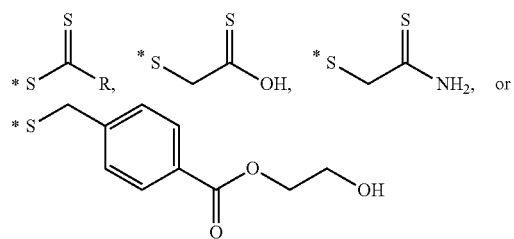

wherein * represents a point of covalent attachment to the second block, and R is —SC$_2$-C$_{12}$ alkyl or C$_6$H$_5$.

* * * * *